(12) United States Patent
Walker et al.

(10) Patent No.: US 7,893,055 B2
(45) Date of Patent: Feb. 22, 2011

(54) HIV INTEGRASE INHIBITORS

(75) Inventors: Michael A. Walker, Durham, CT (US); Chen Li, Storrs, CT (US); Katharine A. Grant-Young, Madison, CT (US); John D. Matiskella, Wallingford, CT (US); B. Narasimhulu Naidu, Durham, CT (US); Jacques Banville, St-Hubert (CA); Francis Beaulieu, Laprairie (CA); Carl Ouellet, Boucherville (CA); Annapurna Pendri, Glastonbury, CT (US); Roger Remillard, Napierville (CA); Yasutsugu Ueda, Clinton, CT (US); Ting T. Yin, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 519 days.

(21) Appl. No.: 11/768,458

(22) Filed: Jun. 26, 2007

(65) Prior Publication Data

US 2008/0004265 A1 Jan. 3, 2008

Related U.S. Application Data

(60) Provisional application No. 60/817,009, filed on Jun. 28, 2006.

(51) Int. Cl.
*A61P 31/00* (2006.01)
*A61K 31/535* (2006.01)
*C07D 498/02* (2006.01)

(52) U.S. Cl. .................... 514/230.5; 544/105
(58) Field of Classification Search .............. 514/230.5; 544/105
See application file for complete search history.

(56) References Cited

U.S. PATENT DOCUMENTS

| | | | |
|---|---|---|---|
| 7,037,908 B2 | 5/2006 | Naidu et al. |
| 7,115,601 B2 | 10/2006 | Naidu et al. |
| 7,135,467 B2 | 11/2006 | Walker et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,273,859 B2 | 9/2007 | Naidu |
| 2006/0046985 A1 | 3/2006 | Crescenzi et al. |

FOREIGN PATENT DOCUMENTS

| | | |
|---|---|---|
| EP | 1698628 A1 | 9/2006 |
| WO | WO 2005/061490 A1 | 7/2005 |
| WO | WO 2005/061501 A2 | 7/2005 |
| WO | WO 2006/103399 A1 | 10/2006 |
| WO | WO 2006/121831 A2 | 11/2006 |

OTHER PUBLICATIONS

U.S. Appl. No. 11/599,580, filed Nov. 14, 2006, B. Narasimhulu Naidu.
U.S. Appl. No. 11/754,462, filed May 29, 2007, B. Narasimhulu Naidu, et al.
U.S. Appl. No. 11/511,751, filed Aug. 29, 2006, Jacques Banville, et al.
U.S. Appl. No. 11/561,039, filed Nov. 17, 2006, B. Narasimhulu Naidu, et al.
U.S. Appl. No. 11/595,429, filed Nov. 10, 2006, B. Narasimhulu Naidu, et al.
U.S. Appl. No. 11/590,637, filed Oct. 31, 2006, B. Narasimhulu Naidu.

*Primary Examiner*—Brenda L Coleman
(74) *Attorney, Agent, or Firm*—James Epperson

(57) ABSTRACT

The invention encompasses a series bicyclic pyrimidinone compounds of Formula I which inhibit HIV integrase and prevent viral integration into human DNA. This action makes the compounds useful for treating HIV infection and AIDS. The invention also encompasses pharmaceutical compositions and methods for treating those infected with HIV.

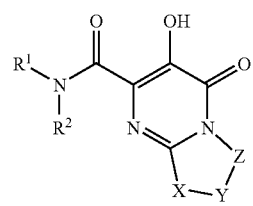

7 Claims, No Drawings

HIV INTEGRASE INHIBITORS

CROSS REFERENCE TO RELATED APPLICATIONS

This application claims the benefit of U.S. Provisional Application Ser. No. 60/817,009, filed Jun. 28, 2006.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. N. Engl. J. Med. 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. JAMA 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. Science 2000, 287, 646). And recently, HIV integrase inhibitors have been accepted into clinical trials for treating AIDS and HIV infection (Neamati Expert. Opin. Ther. Patents 2002, 12, 709, Pais and Burke Drugs Fut. 2002, 27, 1101).

DESCRIPTION OF THE INVENTION

The invention encompasses compounds of Formula I, pharmaceutically acceptable salts thereof, pharmaceutical compositions, and methods for inhibiting HIV integrase and treating those infected with HIV or AIDS.

One aspect of the invention is a compound of Formula I

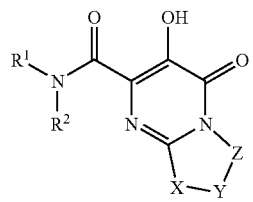

where:

$R^1$ is $(Ar^1)$alkyl;

$R^2$ is $(Ar^1)$alkyl, hydrogen, alkyl, hydroxy, or alkoxy;

$R^3$ is hydrogen or alkyl;

$R^4$ is alkyl or cycloalkyl;

$R^5$ is hydrogen or alkyl;

$R^6$ is hydrogen or alkyl;

or $R^5$ and $R^6$ taken together is $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, $OCH_2CH_2$, $CH_2OCH_2$, $OCH_2CH_2CH_2$, $CH_2OCH_2CH_2$, $OCH_2CH_2CH_2$, $CH_2OCH_2CH_2CH_2$, $CH_2CH_2OCH_2CH_2$, $OCH_2CH_2CH_2CH_2$, $CH_2OCH_2CH_2CH_2$, $CH_2CH_2OCH_2CH_2CH_2$, $N(R^3)CH_2CH_2$, $CH_2N(R^3)CH_2$, $N(R^3)CH_2CH_2CH_2$, $CH_2N(R^3)CH_2CH_2$, $N(R^3)CH_2CH_2CH_2CH_2$, $CH_2N(R^3)CH_2CH_2CH_2$, $CH_2CH_2N(R^3)CH_2CH_2$, $N(R^3)CH_2CH_2CH_2CH_2CH_2$, $CH_2N(R^3)CH_2CH_2CH_2CH_2$, or $CH_2CH_2N(R^3)CH_2CH_2CH_2$;

$Ar^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, indazolyl, benzoisoxazolyl, benzoisothiazolyl, benzimidazolyl, benzoxazolyl, benzothiazolyl,

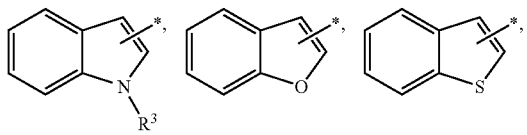

-continued

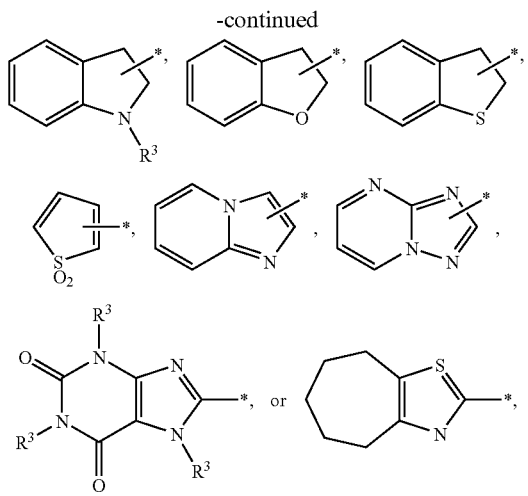

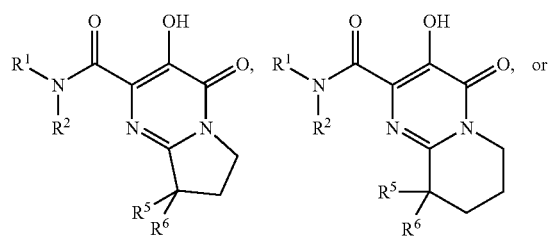

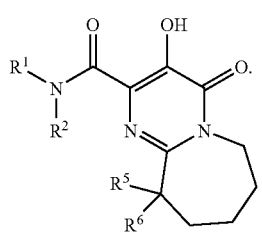

and is substituted with 0-3 substituents selected from the group consisting of oxo, amino, cyano, halo, alkyl, haloalkyl, hydroxy, alkoxy, haloalkoxy, $COR^3$, $CO_2R^3$, $CON(R^3)(R^3)$, $(COR^3)$alkyl, $(CO_2R^3)$alkyl, $(CON(R^3)(R^3))$alkyl, alkylthio, (alkyl)SO, $SO_2R^4$, $Ar^2$ and $(Ar^2)$alkyl;

$Ar^2$ is phenyl substituted with 0-2 substituents selected from the group consisting of cyano, halo, alkyl, haloalkyl, alkoxy, and haloalkoxy; and X—Y—Z is $C(R^5)(R^6)CH_2CH_2$, $C(R^5)(R^6)CH_2CH_2CH_2$, $C(R^5)(R^6)CH_2CH_2CH_2CH_2$, $C(R^5)(R^6)OCH_2$, $C(R^5)(R^6)OCH_2CH_2$, $C(R^5)(R^6)OCH_2CH_2CH_2$, $C(R^5)(R^6)CH_2OCH_2CH_2$, $C(R^5)(R^6)N(R^3)CH_2$, $C(R^5)(R^6)N(R^3)CH_2CH_2$, $C(R^5)(R^6)N(R^3)CH_2CH_2CH_2$, or $C(R^5)(R^6)CH_2N(R^3)CH_2CH_2$;

or a pharmaceutically acceptable salt thereof.

Another aspect of the invention is a compound of Formula I according one of the following structures:

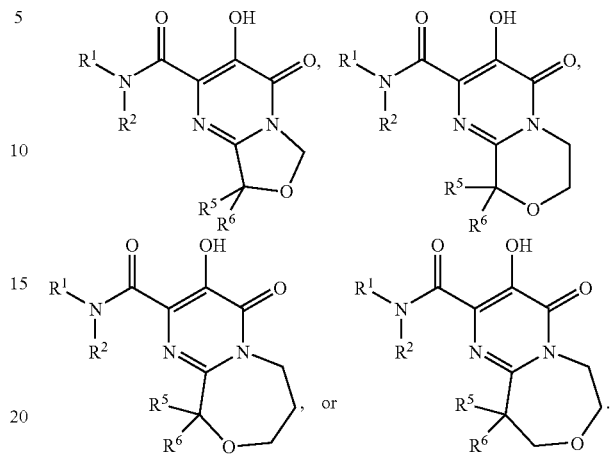

Another aspect of the invention is a compound of Formula I according one of the following structures:

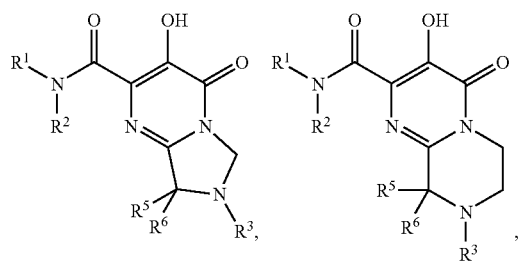

Another aspect of the invention is a compound of Formula I according one of the following structures:

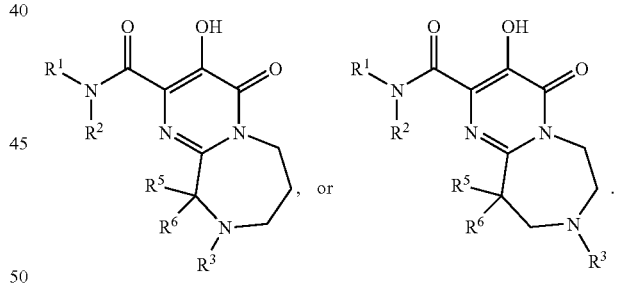

Another aspect of the invention is a compound of Formula I where $R^1$ is $(Ar^1)$methyl.

Another aspect of the invention is a compound of Formula I where $Ar^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, or tetrazolyl, and is substituted with 0-3 substituents selected from the group consisting of oxo, amino, cyano, halo, alkyl, haloalkyl, hydroxy, alkoxy, haloalkoxy, $COR^3$, $CO_2R^3$, $CON(R^3)(R^3)$, $(COR^3)$alkyl, $(CO_2R^3)$alkyl, $(CON(R^3)(R^3))$alkyl, alkylthio, (alkyl)SO, $SO_2R^4$, $Ar^2$ and $(Ar^2)$alkyl.

Another aspect of the invention is a compound of Formula I where $Ar^1$ is indazolyl, benzoisoxazolyl, benzoisothiazolyl, benzimidazolyl, benzoxazolyl, benzothiazolyl,

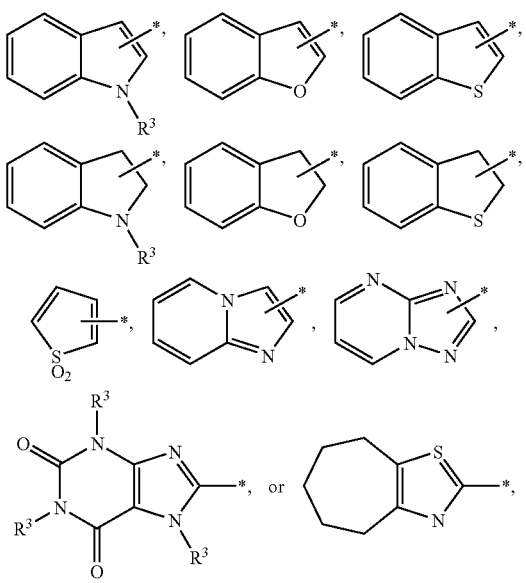

and is substituted with 0-3 substituents selected from the group consisting of oxo, amino, cyano, halo, alkyl, haloalkyl, hydroxy, alkoxy, haloalkoxy, COR³, CO₂R³, CON(R³)(R³), (COR³)alkyl, (CO₂R³)alkyl, (CON(R³)(R³))alkyl, alkylthio, (alkyl)SO, SO₂R⁴, Ar² and (Ar²)alkyl.

Another aspect of the invention is a compound of Formula I where R² is hydrogen.

For a compound of Formula I, any scope of R¹, R², R³, R⁴, R⁵, R⁶, Ar¹, Ar², and X—Y—Z can be used independently with any scope of any other substituent.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with an alkyl moiety include straight and branched isomers composed of 1 to 6 carbon atoms for the alkyl portion. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R. Some substituents are divalent and should be construed to attach in either of the two configurations.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

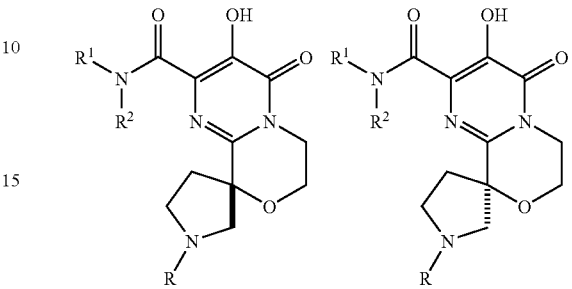

The invention includes all tautomeric forms of the compounds. An example of a tautomeric pair is shown below.

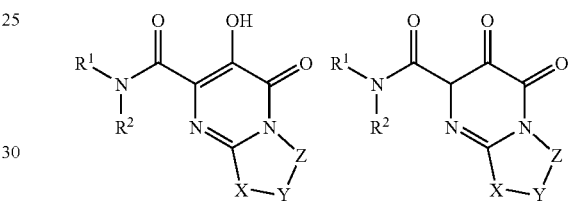

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

Some compounds can be synthesized from an appropriately substituted heterocycle I-1 according to Scheme I, where $R_a$ and P can serve as protecting groups (see Greene, T. W. and Wutz, P. G. M. Protective Groups in Organic Synthesis, Second Edition, 1991, John Wiley and Sons, New York). When P is benzyl or substituted benzyl it can be removed by hydrogenolysis (H₂—Pd/C) or acid hydrolysis (trifluoroacetic acid) to yield intermediate I-2. I-2 can be transaminated to I-4 by reaction with amine I-3. In a number of cases this reaction can be carried out by heating I-3 and I-2 together in the presence of base. Alternatively, standard amide coupling reagents can be used to effect the formation of the amide bond. When $R_a$ is a lower alkyl group, $R_a$ can be removed under ester hydrolysis conditions, such as treatment with NaOH, LiOH, or KOH to deliver the corresponding carboxylic acid I-5. Alternatively, $R_a$ can be removed by nucleophilic displacement using NaI. When $R_a$ is benzyl and substituted benzyl, $R_a$ can be removed by hydrogenolysis. Intermediate I-5 can be coupled using amide bond forming reagents such as BOP, DCC, EDCI, PyBrop, PyBop or other reagents (see March, J. Advanced Organic Chemistry, Fourth Edition 1992 John Wiley & Sons, New York). The resulting intermediate I-6 can be deprotected as described for intermediate I-1.

Scheme I.

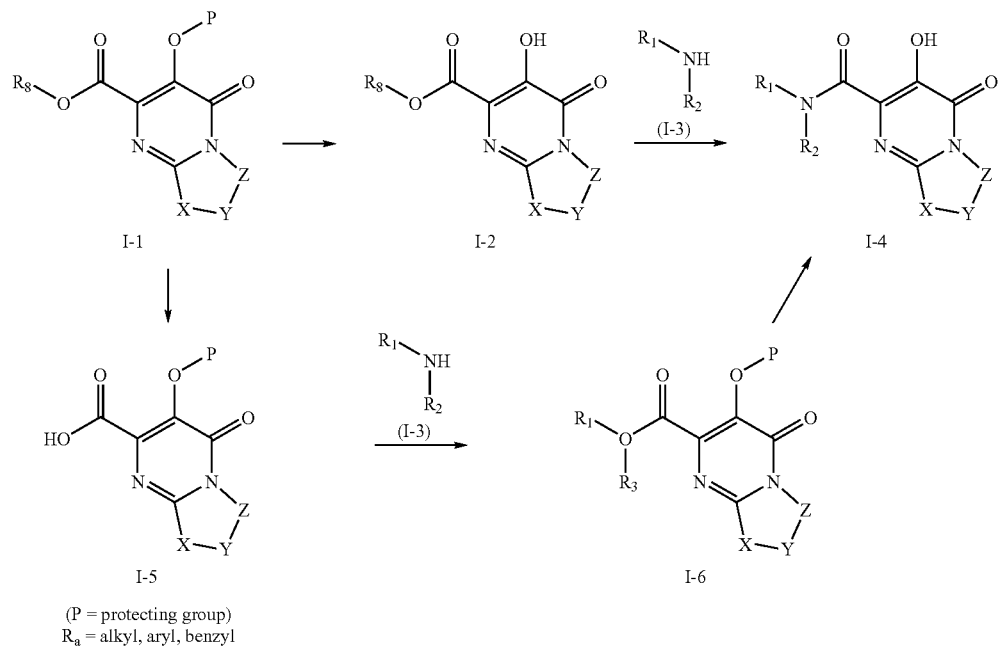

(P = protecting group)
$R_a$ = alkyl, aryl, benzyl

In Scheme II, intermediate II-3 can be prepared using methods similar to those described in Sunderland, J. S.; Botta, M.; Aime, S.; Raymond, K. N. Inorg. Chem. (2001), 40, 6756-6756, where II-1 and II-2 are condensed, to provide intermediate I-3. This reaction is usually conducted in the presence of a base such as sodium hydride (NaH), sodium ethoxide (EtONa) or lithium hexamethyldisilazide (LiH-MDS). Using the methods described in the reference, II-3 can be condensed with an appropriately substituted amidine II-4 to form II-5. Substituent B can be a leaving group, such as -halo (Cl, Br or I) or can be converted to a leaving group under appropriate conditions such as by forming the corresponding methylsulfonate ester. When substituent B is a methyl sulphide group it can be treated with iodomethane to form a dimethylsulfonium intermediate which is activated towards nucleophilic attack to effect ring closure.

Scheme II.

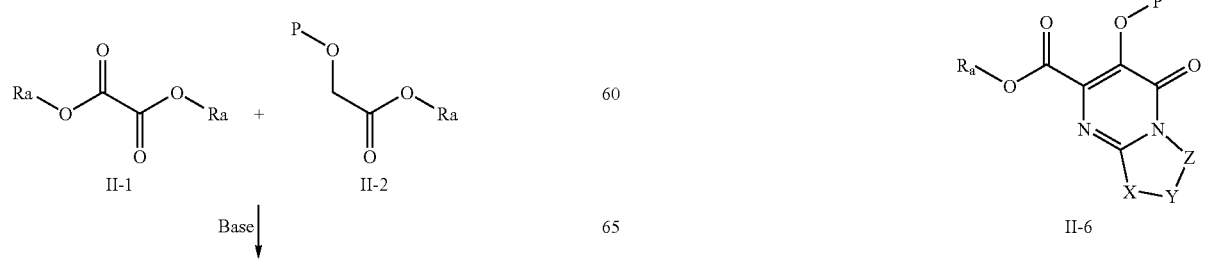

-continued

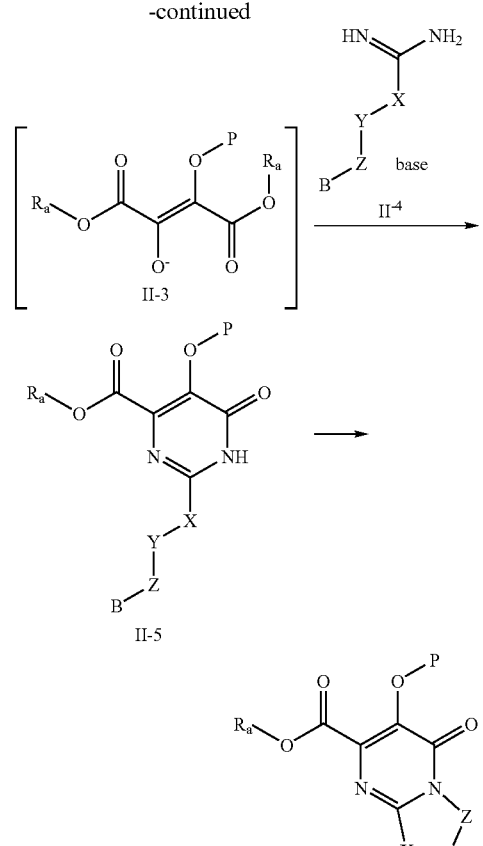

In Scheme III, intermediate II-3 can be condensed with a cyclic-amidine to yield intermediate I-1. Intermediate III-1 can be prepared using known methods (see Patai, S. and Rappoport, Z. The Chemistry of Amidines and Imidates, Volume 2, 1991, John Wiley & Sons, New York).

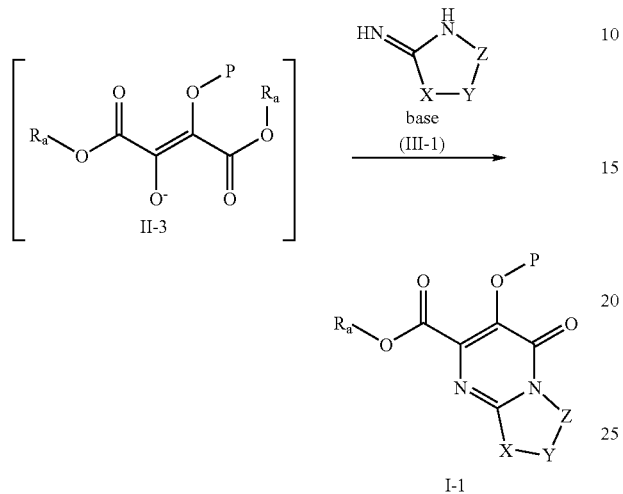

In Scheme IV, nitrile IV-1, possessing a potential leaving group B, can be reacted with hydroxylamine to form intermediate IV-2. This intermediate can be reacted with a suitably protected alkyne to form IV-3 which can rearrange to from intermediate IV-4 according to literature methods (Culbertson, T. P. *Journal of Heterocyclic Chemistry*, 1979, 16, 1423-1424).

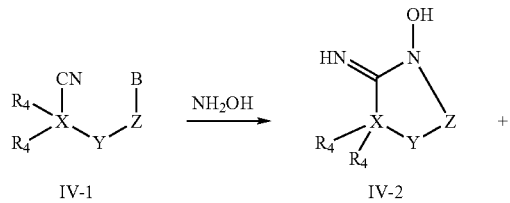

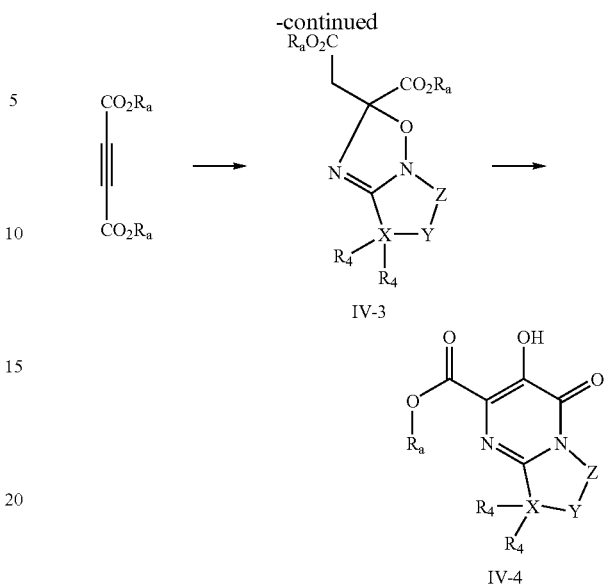

Scheme V illustrates the syntheses of some heterocycle substituted methyl-amines (V-3) suitable for coupling to the pyrimidinone templates described in the previous schemes. Intermediate alcohol V-2 can be purchased or synthesized from the corresponding carboxylic acid or carboxylic acid ester, V-1. According to this method V-1 is subjected to a reducing agent such as lithium aluminum hydride (LAH) to effect the reduction of the carboxylic acid functional group to the corresponding alcohol. This is a well known synthetic transformation which can be accomplished by any one of a variety of reducing agents. In the next step, the hydroxyl group of V-2 is converted to a leaving group, for example the corresponding mesylate ester, which is then subjected to nucleophilic substitution by sodium azide. Intermediate V-3 is produced following reduction of the azide formed in this step. Alternatively, reduction appropriately substituted nitrile containing compounds such as V-4, is also useful for the synthesis of V-3. In yet another method amide V-5 can be reduced, using any one of the many methods known in the art to provide V-3. Coupling of V-3 to form the final product can be accomplished according to the methods described above.

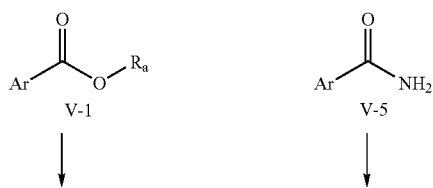

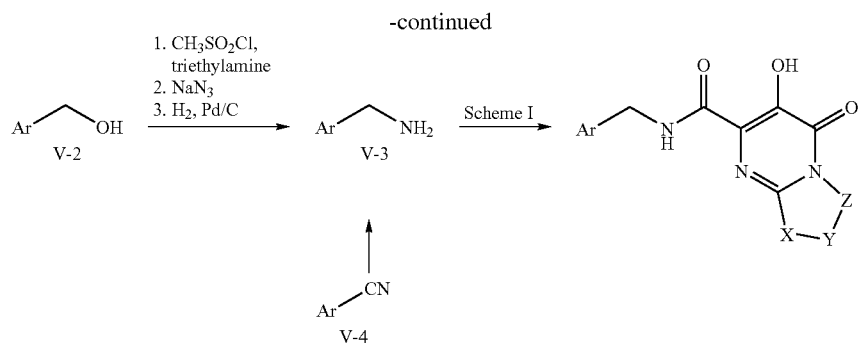

In Scheme VI, aldehyde VI-1 is treated with hydroxyl amine to form the corresponding oxime, VI-2. This intermediate can be reduced with LAH, or other reducing agents known in the art, to provide amine VI-3, which can be carried forward as before.

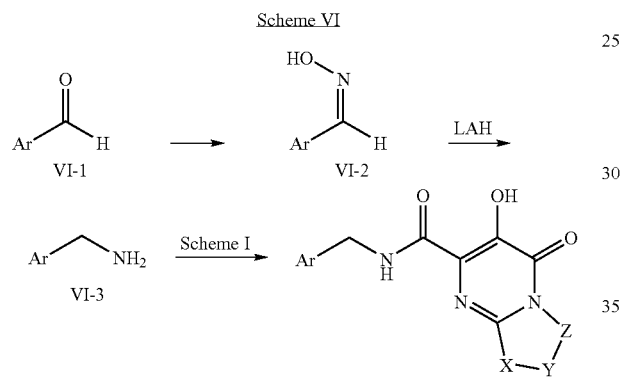

Biological Methods

HIV-Integrase InhibitionActivity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908-5911 (1995). The sequences of substrate and target DNA were described in *Nucleic Acid Research* 22, 1121-1122 (1994). Results are shown in the Table 1. Activity equal to A refers to a compound having $IC_{50}$=0.002 to 0.10 μM while B and C denote compounds having $IC_{50}$=0.1 to 1.0 μM and $IC_{50} \geq 1.0$ μM respectively.

TABLE 1

| Example | Activity |
|---------|----------|
| 1 | A |
| 2 | B |

TABLE 1-continued

| Example | Activity |
|---------|----------|
| 3 | B |
| 4 | B |
| 5 | C |
| 6 | C |
| 7 | B |
| 8 | B |
| 9 | A |
| 10 | A |
| 11 | A |
| 12 | A |
| 13 | A |
| 14 | A |
| 15 | A |
| 16 | B |
| 17 | C |
| 18 | A |
| 19 | A |
| 20 | A |
| 21 | C |
| 22 | C |
| 23 | C |
| 24 | A |
| 25 | C |
| 26 | C |
| 27 | A |
| 28 | A |
| 29 | A |
| 30 | A |
| 31 | A |
| 32 | A |
| 33 | A |
| 34 | A |
| 35 | C |
| 36 | A |
| 37 | A |
| 38 | A |
| 39 | B |
| 40 | A |
| 41 | A |
| 42 | A |
| 43 | C |
| 44 | A |
| 45 | C |
| 46 | B |
| 47 | B |
| 48 | C |
| 49 | C |
| 50 | C |
| 51 | C |
| 52 | C |
| 53 | B |
| 54 | B |
| 55 | B |
| 56 | A |
| 57 | B |
| 58 | B |

TABLE 1-continued

| Example | Activity |
|---|---|
| 59 | A |
| 60 | C |
| 61 | B |
| 62 | B |
| 63 | B |
| 64 | B |
| 65 | B |
| 66 | B |
| 67 | A |
| 68 | C |
| 69 | B |
| 70 | A |
| 71 | B |
| 72 | A |
| 73 | C |
| 74 | C |
| 75 | C |
| 76 | A |
| 77 | A |
| 78 | A |
| 79 | A |
| 80 | A |
| 81 | A |
| 82 | A |
| 83 | A |
| 84 | A |
| 85 | A |
| 86 | C |
| 87 | A |
| 88 | B |
| 89 | C |
| 90 | A |
| 91 | C |
| 92 | A |
| 93 | B |

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC, 18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In Techniques in HIV Research. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $EC_{50}$=0.003 to 0.10 μM while B and C denote compounds with $EC_{50}$=0.1 to 1.0 μM and $EC_{50} \geq 1.0$ μM respectively.

TABLE 2

| Example | Activity |
|---|---|
| 1 | A |
| 2 | A |
| 3 | B |
| 4 | B |
| 5 | C |
| 7 | B |
| 8 | B |
| 9 | B |
| 10 | A |
| 11 | A |
| 12 | B |
| 13 | A |
| 14 | C |
| 15 | A |
| 18 | C |
| 19 | A |
| 20 | A |
| 21 | B |
| 22 | C |
| 24 | B |
| 27 | B |
| 28 | B |
| 29 | A |
| 30 | A |
| 31 | A |
| 32 | B |
| 33 | A |
| 34 | A |
| 36 | B |
| 37 | A |
| 38 | B |
| 40 | B |
| 41 | B |
| 42 | B |
| 44 | A |
| 56 | A |
| 59 | B |
| 67 | B |
| 70 | C |
| 72 | B |
| 76 | B |
| 77 | A |
| 78 | B |
| 79 | A |
| 80 | A |
| 81 | A |
| 82 | A |
| 83 | A |
| 84 | A |
| 85 | B |
| 87 | B |
| 90 | A |
| 92 | A |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable salt thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 3 lists some agents useful in treating AIDS and HIV infection which are suitable for this invention.

TABLE 3

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, |
| AL-721 | Ethigen (Los Angeles, CA) | PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (-)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptaseinhibitor) | Hoechst Marion Roussel | HIV infection, AIDS, ARC |

TABLE 3-continued

| DRUG NAME | MANUFACTURER | INDICATION |
|---|---|---|
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. Amgen | Kaposi's sarcoma AIDS, in combination w/AZT |
| Granulocyte Colony Stimulating Factor | | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |

TABLE 3-continued

| DRUG NAME | MANUFACTURER | INDICATION |
|---|---|---|
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Intermediate 1

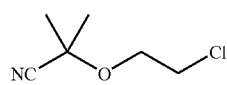

2-(2-Chloroethoxy)-2-methylpropanenitrile. (Navalokina, R. Et al J. Org. Chem. USSR (Engl. Trans.), 1980, 16, 1382-1386. 2) Ramalingam, K. U.S. Pat. No. 4,864,051, 1989.). A 250 mL round bottom flask was charged with ZnCl$_2$ (68.14 g, 0.5 mole) which was then fused by heating under vacuum. After returning to room temperature the material was placed under an atmosphere of N$_2$. To this was added acetone cyanohydrin (45.66 mL, 0.5 mole) followed by 2-chloroethanol (50.24 mL, 0.75 mole) and the mixture placed in a preheated oil bath (60° C.). After stirring for 18-20 h at 60° C., the reaction mixture was cooled, diluted with water (300 mL) and washed with CH$_2$Cl$_2$ (5×100 mL). The combined CH$_2$Cl$_2$ extracts were dried (Na$_2$SO$_4$), filtered and concentrated under vacuum to afford the crude product as a yellow liquid. Purification was accomplished by vacuum distillation (10 mm Hg) using a vigreux column. The fraction boiling between 65-75° C. was collected to afford the desired product as a colorless oil (47.1 g, 63.8% yield). $^1$H NMR (500 MHz, CDCl$_3$) δ ppm: 3.85 (2H, t, J=5.8 Hz), 3.64 (2H, t, J=5.8 Hz), 1.60 (6H, s).

Additional procedure. ZnCl$_2$ (352.3 g 2.59 moles) was added to a 2 L round bottom flask equipped with a mechanical stirrer, nitrogen inlet-outlet, temperature probe, and condenser. Acetone cyanohydrin (110.0 g 1.29 moles) was slowly added to the stirred solid over 30 minutes keeping the temperature below 32° C. with external cooling. To the slurry, 2-chloroethanol (124.9 g 1.55 moles) was slowly added over 20 minutes keeping the temperature below 32° C. with external cooling. Acetone (3.75 g, 64.6 mmoles) was added and the mixture was heated to 60° C. After stirring for 4 h at 60° C., the reaction mixture was cooled to 30-35° C., diluted with water (1.10 L) and extracted with CH$_2$Cl$_2$ (1×440 mL and 1×220 mL). The combined CH$_2$Cl$_2$ extracts were washed with 0.5M sodium bicarbonate (330 mL), followed by water (3×330 mL). The dichloromethane solution was concentrated under vacuum to afford crude product (109 g). The crude product was purified by vacuum distillation (10 mm Hg) using a Vigreux column. The fraction boiling at 60-80° C. was collected to afford 2-(2-chloroethoxy)-2-methylpropanenitrile as colorless oil (88.7 g).

Intermediatte 2

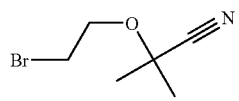

2-(2-Bromoethoxy)-2-methylpropanenitrile. Dichloromethane (42 mL) and tin tetrachloride (64.9 g, 249 mmol) were added to a 250 mL round bottom flask equipped with a magnetic stirrer, temperature probe, condenser and Argon inlet-outlet. The mixture was cooled to 0-5° C. Acetone cyanohydrin (21.2 g, 249 mmol) was added over 15 min, followed by slow addition of 2-bromoethanol (46.69 g, 373.6 mmol). The reaction mixture was stirred at 20-25° C. for 22 h. The mixture was cooled to 0-5° C., diluted with water (148 mL), and extracted with dichloromethane (3×64 mL). The combined CH$_2$Cl$_2$ extracts were dried (MgSO$_4$), filtered and concentrated under vacuum to afford the crude product as a yellow liquid. The material was purified by vacuum distillation (10 mm Hg) using a Vigreux column. The fraction boiling between 75-85° C. was collected to afford 2-(2-Bromoethoxy)-2-methylpropanenitrile as a colorless oil (15.09 g).

Intermediate 3

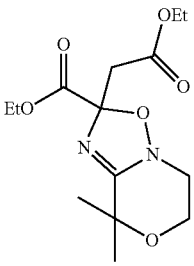

Ethyl 2-(2-ethoxy-2-oxoethyl)-8,8-dimethyl-2,5,6,8-tetrahydro-[1,2,4]oxadiazolo[3,2-c][1,4]oxazine-2-carboxylate. To a stirred solution of 2-(2-chloroethoxy)-2-methylpropanenitrile (14.7 g, 0.10 mole) and NaI (1.5 g, 10 mmol) in ethanol (50 mL) was added an aqueous solution (50%) of hydroxylamine (18.4 g, 0.30 mole) resulting in an exothermic reaction. Following this the reaction mixture was heated at 80° C. for 2 h. Upon cooling to room temperature the solvent was removed. The resulting residue was dissolved in 1:1 ethanol/H$_2$O (100 mL) and cooled in an ice bath. To this was added diethyl acetylenedicarboxylate (17.6 mL, 0.110 mole) over 10 min. The reaction mixture was allowed to warm to room temperature and stirred for 1 h. Following this, it was diluted with ethyl acetate (250 mL), washed with H$_2$O (2×100 mL), brine (50 mL), dried over Na$_2$SO$_4$, filtered and concentrated to give the crude product as a yellow oil. Flash chromatography on a silica gel column, eluting with 20-40% ethyl acetate/Hexanes, provided the title compound as a viscous pale yellow oil (15.29 g, 48.6% yield). $^1$H NMR (500 MHz, CDCl$_3$) δ ppm: 4.35-4.28 (2H, m), 4.18-4.12 (2H, m), 3.60-3.56 (1H, m), 3.51-3.47 (1H, m), 3.30 (1H, d, J=16.2 Hz), 2.94 (1H, d, J=16.2 Hz), 1.52 (3H, s), 1.51 (3H, s), 1.29 (3H, t, J=7.0 Hz), 1.24 (3H, t, J=7.0 Hz). LCMS (M+H) calcd for C$_{14}$H$_{23}$N$_2$O$_7$: 315.16; found: 315.33.

Additional procedures. A solution of 2-(2-chloroethoxy)-2-methylpropanenitrile (5.0 g, 33.87 mmol) in anhydrous methanol (33 mL) was added to a 3-necked flask equipped with a reflux condenser and argon inlet-outlet. Hydroxylamine hydrochloride (2.82 g, 40.58 mmol, 1.20 eq) was added, followed by powdered sodium carbonate (3.95 g, 37.26 mmol, 1.10 eq). The resulting suspension was allowed to stir at room temperature under argon for 18 hrs. The reaction mixture was then heated at 70° C. in an oil bath for 3 h. The resulting suspension was allowed to cool to room temperature. The mixture was filtered though celite and the filter cake was washed with additional methanol. The filtrate was concentrated at reduced pressure to give a semi-solid material which was suspended in chloroform (~80 mL). After stirring for 1 hour, the resulting suspension was filtered through celite and the filter cake was washed with additional chloroform. The filtrate was concentrated at reduced pressure to give very pale amber oil which crystallized upon standing to crude cyclic amine oxide (5.79 g).

The above crude intermediate (3.0 g) was dissolved in hot methanol (3 mL). The resulting solution was diluted with ethyl acetate (30 mL). The solution was heated at reflux to distill out the bulk of the methanol. Heating was stopped when the distillate reached 75° C. The resulting solution was allowed to stand 30 min at room temperature and 2.5 h at 5° C. The crystalline solid was collected by filtration, washed with ethyl acetate, and dried in vacuo over night at 45-50° C. to give an anhydrous form of the cyclic amine oxide as a colorless crystalline solid, 1.94 g.

The crude intermediate above (43.9 g) prepared from a similar experiment described above was dissolved in hot methanol (45 mL). The resulting solution was diluted with ethyl acetate (400 mL) and water (11.5 mL). The solution was heated at reflux to distill out the bulk of the methanol. Heating was stopped when the distillate reached 71.5° C. The resulting solution was diluted with 100 mL of ethyl acetate and 1 mL of methanol (needed to prevent oiling), seeded with a sample of crystalline monohydrate and let slowly cool to room temperature over night. The solid was collected by filtration, washed with ethyl acetate (100 mL), dried first under nitrogen and in vacuo at room temperature to give the monohydrate form the intermediate cyclic amine oxide as a colorless crystalline solid, 27.93 g.

Ethyl 3-hydroxy-9,9-dimethyl-4-oxo-4,6,7,9-tetrahydro-pyrimido[2,1-c][1,4]oxazine-2-carboxylate. $ZnCl_2$ (544.5 g 4.0 moles) was added to a 3 L round bottom flask equipped with a mechanical stirrer, nitrogen inlet-outlet, temperature probe, and condenser. Acetone cyanohydrin (170.0 g, 2.00 mol) was slowly added to the stirred solid over 30 minutes keeping the temperature below 32° C. with external cooling. To the slurry, 2-chloroethanol (193.0 g, 2.40 mol) was slowly added over 20 minutes keeping the temperature below 32° C. with external cooling. Acetone (5.80 g, 99.8 mmol) was added and the mixture was heated to 60° C. After stirring for 4 h at 60° C., the reaction mixture was cooled to 30-35° C., diluted with water (1.70 L) and extracted with $CH_2Cl_2$ (1×680 mL and 1×340 mL). The combined $CH_2Cl_2$ extracts were washed with 0.5M sodium bicarbonate (510 mL), followed by water (3×510 mL). The dichloromethane solution (1210 mL) contained 152 g of 2-(2-chloroethoxy)-2-methylpropanenitrile by GC quantification, GC purity: 94.7%.

The above dichloromethane solution of 2-(2-chloroethoxy)-2-methylpropanenitrile (600 mL, 76 g, 0.515 moles) was added to a 1 L round bottom flask equipped with a mechanical stirrer, nitrogen inlet, temperature probe, and condenser. The solution was concentrated at atmospheric pressure and $CH_2Cl_2$ was replaced by methanol (450 mL). The methanol solution was cooled to 20-25° C. and sodium carbonate (21.83 g, 0.206 mmol) was added. An aqueous solution (50%) of hydroxylamine (33.65 mL, 0.617 mol) was added, followed by water (76 mL). The thin slurry was stirred at 20-25° C. for 18 h. Then the reaction mixture was heated to reflux (temperature about 65° C.) for 3 h. HPLC analysis showed the solution contained 61.5 g of 2,2-dimethyl-4-oxy-5,6-dihydro-2H-1,4-oxazin-3-ylamine; with HPLC purity of 97.2.

The above solution of cyclic amine oxide was cooled to 20-25° C. and the pH (7.0) was adjusted to 7.5 with 0.5M sodium carbonate (20 mL). The mixture was cooled to 0 to –5° C. Diethyl acetylenedicarboxylate (78.85 g, 0.463 moles) was added over 1 h keeping the temperature below 5° C. The mixture was stirred for 30 min. Ethyl acetate (760 mL) and water (380 mL) were added. The phases were separated and the aqueous phase was extracted with ethyl acetate (380 mL). The two ethyl acetate solutions were combined, washed twice with 50% brine (each 380 mL). The ethyl acetate solution contained ethyl 2-(2-ethoxy-2-oxoethyl)-8,8-dimethyl-2,5,6,8-tetrahydro-[1,2,4]oxadiazolo[3,2-c][1,4]oxazine-2-carboxylate. Estimated amount of the titled intermediate in the solution by HPLC was 130 g, HPLC AP 79.0. A sample was purified by reverse-phase chromatography giving an oil of 99% purity by HPLC.

Alternate procedure. To a solution of 2-(2-chloroethoxy)-2-methylpropanenitrile (5.00 g, 33.87 mmol) in methanol (30 mL) was added at 20-22° C. a 50% aqueous solution of hydroxylamine (2.21 mL, 40.58 mmol). Sodium carbonate (1.44 g, 13.59 mmol) and finally water (5 mL) were added. The suspension was stirred at 20-25° C. for 18 h. The reaction mixture was heated at reflux (65-66° C.) for 3 h. The resulting solution was cooled to 20-25° C. The pH (7.5) required no adjustment. The mixture was cooled to –5° C. and dimethyl acetylenedicarboxylate (3.75 mL, 30.56 mmoles) was added slowly over about 18 min keeping the temperature between –5° C. to 0° C. The mixture was stirred for 60 min. Additional dimethyl acetylenedicarboxylate (0.4 mL, 3.26 mmoles) was added and mixture was stirred another 10 min at 0° C. to complete the reaction as confirmed by HPLC. Ethyl acetate (50 mL) and water (25 mL) were added to the reaction mixture. The phases were separated and the aqueous phase was extracted again with ethyl acetate (25 mL). The combined ethyl acetate extracts were washed with about 14% aq. NaCl (2×25 mL). The solvent was removed under vacuum to afford methyl 2-(2-methoxy-2-oxoethyl)-8,8-dimethyl-2,5,6,8-tetrahydro-[1,2,4]oxadiazolo[3,2-c][1,4]oxazine-2-carboxylate as a crude oil (9.4 g, 96.9% yield) with a purity of 71% by HPLC. A sample (0.80 g) was purified by reverse-phase chromatography giving an oil (0.48 g) of 97% purity by HPLC, which crystallized on standing; mp 68-69° C.

Intermediate 4

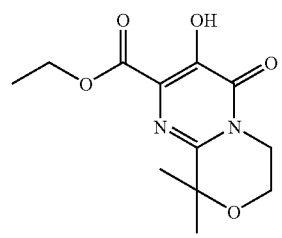

Ethyl 3-hydroxy-9,9-dimethyl-4-oxo-4,6,7,9-tetrahydro-pyrimido[2,1-c][1,4]oxazine-2-carboxylate. A solution of ethyl 2-(2-ethoxy-2-oxoethyl)-8,8-dimethyl-2,5,6,8-tetrahydro-[1,2,4]oxadiazolo[3,2-c][1,4]oxazine-2-carboxylate (31.16 g) in 1,2,4-trimethylbenzene (200 mL) was heated at 180° C. for 5 h. The resulting dark reaction solution was cooled then concentrated to give a dark brown paste which was taken up into ethyl acetate (250 mL) and extracted with 0.5 M aq Na$_2$CO$_3$ (4×50 mL). The organic layer was discarded and the aqueous layer acidified by carefully adding conc. HCl (20 mL) before being extracted with CH$_2$Cl$_2$ (4×50 mL). The combined CH$_2$Cl$_2$ layers were dried (Na$_2$SO$_4$), filtered and concentrated to give a dark paste which was dissolved in ether (100 mL) and allowed to stand at room temperature in a open flask. The brown/light yellow solid that formed was filtered to afford the title compound. The mother liquor that contained product was re-processed to afford additional material (combined yield ~18-20% over two steps). $^1$H NMR (500 MHz, CDCl$_3$) δ: 10.55 (1H, s), 4.45 (2H, q, J=7.0 Hz), 4.02 (4H, s), 1.61 (6H, s), 1.43 (3H, t, J=7.0 Hz). HRMS (M+H) calcd for C$_{12}$H$_{17}$N$_2$O$_5$: 269.1138; found: 269.1149. Anal calcd for C$_{12}$H$_{16}$N$_2$O$_5$: C, 53.72; H, 6.01; N, 10.44. Found: C, 53.71; H, 6.04; N, 10.30.

An ethyl acetate solution of the ethyl 2-(2-ethoxy-2-oxoethyl)-8,8-dimethyl-2,5,6,8-tetrahydro-[1,2,4]oxadiazolo[3,2-c][1,4]oxazine-2-carboxylate was placed in a 3 L 3-necked flask equipped with a Dean Stark water separator, stirrer, and temperature probe. Ethyl acetate was removed by distillation and replaced with 1,2,4-trimethylbenzene (1.14 L). The resulting solution was heated at 155° C. for 9 h. The dark reaction mixture was cooled to 20-25° C., diluted with water (760 mL) and extracted twice with 0.5M Na$_2$CO$_3$ (each 760 mL) the organic layer was discarded. The aqueous phases were combined and washed with CH$_2$Cl$_2$ (610 mL), phases were separated and the organic layer was discarded. To the resulting aqueous solution was added CH$_2$Cl$_2$ (300 mL), and acidified to pH 2.0 with 6M sulfuric acid (130 mL). Phases were separated, and the aqueous phase was extracted with CH$_2$Cl$_2$ (300 mL). The combined CH$_2$Cl$_2$ layers were separated in two equal portions A and B.

Portion A isolation without charcoal treatment. The CH$_2$Cl$_2$ solution (315 mL) was concentrated to 80 mL at atmospheric pressure. Isopropanol (160 mL) was added and the solution was concentrated to 140 mL at atmospheric pressure. The solution was cooled slowly with stirring to 20-25° C. The resulting slurry was further cooled to 0-5° C. and stirred for 2 h. The solid was filtered, washed with cold isopropanol (70 mL), dried in vacuo at 40-45° C. to afford ethyl 3-hydroxy-9,9-dimethyl-4-oxo-4,6,7,9-tetrahydropyrimido[2,1-c][1,4]oxazine-2-carboxylate as off-white flakes (34.8 g).

Portion B isolation with charcoal treatment. The CH$_2$Cl$_2$ solution (315 mL) was concentrated to 80 mL at atmospheric pressure. Isopropanol (160 mL) was added and the solution was concentrated to 160 mL at atmospheric pressure. Another portion of isopropanol (160 mL) was added followed by charcoal (10 g). The mixture was stirred at reflux temperature (about 82° C.) for 15 min. Charcoal was removed by filtration, the charcoal cake washed with hot (about 80° C.) isopropanol (120 mL) and combined with the filtrate. The combined isopropanol solution was concentrated to 140 mL at atmospheric pressure. The solution was cooled slowly with stirring to 20-25° C. The resulting slurry was further cooled to 0-5° C. and stirred for 2 h. The solid was filtered, washed with cold isopropanol (50 mL), dried in vacuo at 40-45° C. to afford ethyl 3-hydroxy-9,9-dimethyl-4-oxo-4,6,7,9-tetrahydropyrimido[2,1-c][1,4]oxazine-2-carboxylate as off-white flakes (31.3 g).

Alternate procedure. 2-(2-Bromoethoxy)-2-methylpropanenitrile (3.0 g, 15.62 mmol) and methanol (21 mL) was added to a 50 mL round bottom flask equipped with a magnetic stirrer, nitrogen inlet-outlet, temperature probe, and condenser. The methanol solution was cooled to 0-5° C. An aqueous solution (50%) of hydroxylamine (2.13 mL, 39.05 mmol) was added. The reaction mixture was allowed to warm to room temperature and stirred for 2 h, and then heated at 75° C. for 1.5 h.

The reaction mixture was cooled to 0-5° C. and the pH (7.0) was adjusted to pH (8) with 1M sodium carbonate (3.0 mL). Diethyl acetylenedicarboxylate (2.92 g, 17.18 mmoles) was added over 25 min keeping the temperature below 10° C. The reaction mixture was allowed to warm to room temperature and stirred for 2 h. Ethyl acetate (45 mL) and water (15 mL) were added. The phases were separated, the ethyl acetate solution was washed with water (15 mL), dried (MgSO$_4$) filtered and concentrated under vacuum to afford a mixture containing ethyl 2-(2-ethoxy-2-oxoethyl)-8,8-dimethyl-2,5,6,8-tetrahydro-[1,2,4]oxadiazolo[3,2-c][1,4]oxazine-2-carboxylate as the major component an oil (4.6 g).

The above intermediate (4.6 g) and 1,2,4-trimethylbenzene (23 mL) were added to a 100 mL 3-necked round bottom flask equipped with a stirrer, and temperature probe. The resulting solution was heated at 155° C. for 8 h. The dark reaction mixture was cooled to 20-25° C., and extracted five times with 0.5M Na$_2$CO$_3$ (each 4.6 mL) the organic layer was discarded. The aqueous phases were combined and acidified with conc. HCl (2.3 mL), and then extracted with CH$_2$Cl$_2$ (5×4.6 mL). The combined CH$_2$Cl$_2$ layers were dried (MgSO$_4$) filtered and concentrated under vacuum to give a dark paste (1.6 g) which was crystallized from methyl-t-butyl ether (3 mL). The light brown solid was filtered to afford ethyl 3-hydroxy-9,9-dimethyl-4-oxo-4,6,7,9-tetrahydropyrimido[2,1-c][1,4]oxazine-2-carboxylate (351 mg).

Intermediate 5

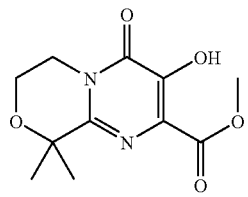

Methyl 3-hydroxy-9,9-dimethyl-4-oxo-4,6,7,9-tetrahydropyrimido[2,1-c][1,4]oxazine-2-carboxylate. A solution of the above crude methyl 2-(2-methoxy-2-oxoethyl)-8,8-dimethyl-2,5,6,8-tetrahydro-[1,2,4]oxadiazolo[3,2-c][1,4]oxazine-2-carboxylate (8.34 g) in 1,2,4-trimethylbenzene (80 mL) was heated at 155° C. for 9 h. The resulting dark mixture was cooled to 20-25° C. and diluted with water (50 mL). The product was extracted into 0.5M Na$_2$CO$_3$ (2×50 mL). The organic layer was discarded. The aqueous phases were combined and washed with CH$_2$Cl$_2$ (40 mL). The organic wash was discarded. The aqueous solution was acidified to pH 2.0 with 6M sulfuric acid (9.0 mL) and the product extracted into CH$_2$Cl$_2$ (2×20 mL). The combined CH$_2$Cl$_2$ layers were evaporated in vacuo. The residue was redissolved in isopropanol (75 mL) at 75° C. and the solution was treated with activated charcoal (0.85 g) at 75-80° C. for 20 min. The charcoal was removed by filtration and washed with hot isopropanol. The combined filtrate and wash was concentrated in vacuo to 40 mL. The resulting slurry was cooled slowly with stirring to 10° C. and stirred for 1 h. The solid was filtered, washed with cold isopropanol (10 mL) and dried in vacuo at 40-45° C. to afford methyl 3-hydroxy-9,9-dimethyl- 4-oxo-4,6,7,9-tetrahydropyrimido[2,1-c][1,4]oxazine-2-carboxylate as an off-white crystalline solid (3.68 g).

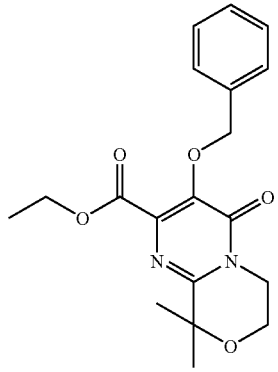

Intermediate 6

Ethyl 3-(benzyloxy)-9,9-dimethyl-4-oxo-4,6,7,9-tetrahydropyrimido[2,1-c][1,4]oxazine-2-carboxylate. To a stirred solution of ethyl 3-hydroxy-9,9-dimethyl-4-oxo-4,6,7,9-tetrahydropyrimido[2,1-c][1,4]oxazine-2-carboxylate, (2.68 g, 10 mmol) and benzyl bromide (1.43 mL, 12 mmol) in DMF (40 mL) was added $K_2CO_3$ (2.07 g, 20 mmol). After stirring 48 h at ambient temperature, the reaction mixture was diluted with ether (100 mL), then washed with water (3×30 mL) and brine (20 mL). The organic layer was dried ($Na_2SO_4$/activated carbon), filtered and concentrated to give a yellow solid. Trituration with hexanes/ether (9:1) afforded the title compound as an off-white solid (2.79 g, 78% yield). $^1$H NMR (500 MHz, $CDCl_3$) δ ppm: 7.48-7.45 (2H, m), 7.37-7.30 (3H, m), 5.25 (2H, s), 4.33 (2H, q, J=7.3 Hz), 4.05-3.99 (4H, m), 1.62 (6H, s), 1.29 (3H, t, J=7.3 Hz). HRMS (M+H) calcd for $C_{19}H_{23}N_2O_5$: 359.1607; found: 359.1611. Anal calcd for $C_{19}H_{22}N_2O_5$: C, 63.67; H, 6.18; N, 7.81; found: C, 63.63; H, 6.16; N, 7.78.

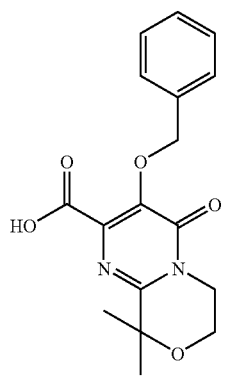

Intermediate 7

3-(Benzyloxy)-9,9-dimethyl-4-oxo-4,6,7,9-tetrahydropyrimido[2,1-c][1,4]oxazine-2-carboxylic acid. A mixture of ethyl 3-(benzyloxy)-9,9-dimethyl-4-oxo-4,6,7,9-tetrahydropyrimido[2,1-c][1,4]oxazine-2-carboxylate, (2.93 g, 8.2 mmol) and LiOH.$H_2O$ (0.84 g, 20 mmol) in 4:1 ethanol/tetrahydrofuran (50 mL) was stirred for 2 h at ambient temperature then concentrated under vacuum. The resulting yellow residue was treated with 1N HCl (25 mL) providing a precipitate that was filtered and dried under vacuum to yield the title compound as a white powder (2.68 g, 99% yield). $^1$H NMR (500 MHz, $CDCl_3$) δ ppm: 7.54-7.48 (2H, m), 7.37- 7.27 (3H, m), 5.44 (2H, s), 4.05-3.93 (4H, m), 1.60 (6H, s).). HRMS (M+H) calcd for $C_{17}H_{19}N_2O_5$: 331.1294; found: 331.1308. Anal calcd for $C_{17}H_{18}N_2O_5$: C, 61.81; H, 5.49; N, 8.48; found: C, 61.84; H, 5.36; N, 8.25.

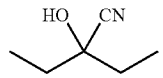

Intermediate 8

2-Ethyl-2-hydroxybutanenitrile. To a solution of potassium phosphate monobasic (140 g, 1.11 mole) in water (250 mL) was added 3-pentanone (75.8 g, 0.88 mole), followed by a solution of sodium cyanide (54 g, 1.10 mole) in water (250 mL), and the resulting mixture stirred for 3 hours. The mixture was extracted with diethyl ether (1×250 mL, then 2×100 mL) and the combined ether layers washed with 1.0 N HCl (200 mL). The ether solution was dried ($Na_2SO_4$), filtered, and concentrated in-vacuo. The crude product was purified by vacuum distillation (bp 87° C., 10 mmHg) to give the title compound (72.4 g, 3% yield) as a clear oil. $^1$H NMR (500 MHz, $CDCl_3$) δ ppm: 2.71 (1H, s), 1.82 (2H, q, J=7.5 Hz), 1.76 (2H, q, J=7.5 Hz), 1.10 (6H, t, J=7.5 Hz). $^{13}$C NMR (500 MHz, $CDCl_3$) δ ppm: 121.21, 73.53, 32.81, 8.27.

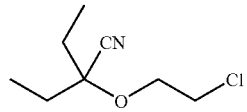

Intermediate 9

2-(2-Chloroethoxy)-2-ethylbutanenitrile. Zinc chloride (68.1 g, 0.5 mol) was fused under vacuum as described in the procedure for the synthesis of intermediate 1. The molten zinc was cooled and the evacuated flask was flushed with nitrogen. The flask was loaded with 2-ethyl-2-hydroxybutanenitrile, (40.3 g, 0.5 mol) and 2-chloroethanol (50.5 mL, 0.75 mmol) then stirred at 60° C. for 20 hours. The reaction mixture was diluted with water (250 mL) and extracted with dichloromethane (1×250 mL, 4×100 mL). The combined organic layers were dried (sodium sulfate), filtered, and concentrated in-vacuo. The crude product was purified by vacuum distillation (bp 83° C., 10 mmHg) to give the title compound (52 g). $^1$H NMR (500 MHz, $CDCl_3$) δ ppm: 3.82 (2H, t, J=5.8 Hz), 3.64 (2H, t, J=5.8 Hz), 1.83 (4H, J=7.3 Hz), 1.03 (6H, t, J=7.6 Hz).

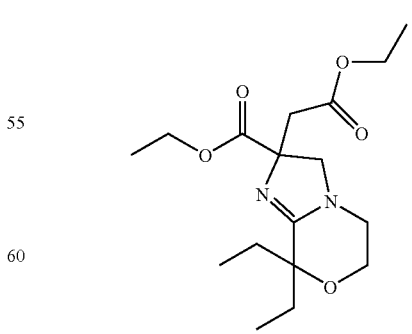

Intermediate 10

Diethyl 2-(2,2-diethyl-3-iminomorpholinooxy)but-2-enedioate. A solution of the product mixture obtained in the synthesis of 2-(2-chloroethoxy)-2-ethylbutanenitrile, (0.171 mol) in absolute ethanol (150 mL) was added dropwise to a solution of hydroxylamine (50% aqueous solution, 33.8 mL, 0.51 mol), sodium carbonate (9.1 g, 0.086 mol) and sodium iodide (2.55 g, 0.017 mol) over 15 minutes. The mixture was heated at 80° C. for 3 hours. The reaction was then concentrated to a thick paste and azeotroped under vacuum with ethanol/water (1:1, 100 mL), water (100 mL) and finally ethanol (100 mL). The residue was taken up in ethanol/water (1:1, 160 mL), cooled (0° C.), and treated with diethyl acetylenedicarboxylate (30.1 mL, 0.188 mol). The reaction was stirred at room temperature for 2 hours, then diluted with water (200 mL) and ethyl acetate (200 mL). The organic layer was separated, washed with water (200 mL) and brine (100 mL), then dried (sodium sulfate), filtered and concentrated in-vacuo. The crude product was purified by column chromatography over silica gel, eluting with 10% to 40% ethyl acetate in hexanes to afford the title compound (25.7 g) as a yellow oil.

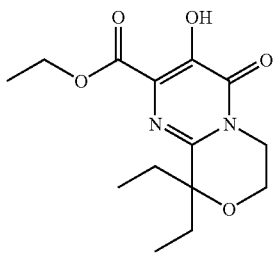

Intermediate 11

Ethyl 9,9-diethyl-3-hydroxy-4-oxo-4,6,7,9-tetrahydropyrimido[2,1-c][1,4]oxazine-2-carboxylate. A solution of diethyl 2-(2,2-diethyl-3-iminomorpholinooxy)but-2-enedioate, (25.7 g) in 1,2,4-trimethylbenzene (100 mL) was heated at reflux (180° C.) for 16 hours. The solvent was then removed in vacuo and the resulting oil placed in a freezer until crystal formation began. The oil-crystal mixture was triturated with diethyl ether (50 mL) and the solid was collected by filtration, washing with a small volume of ether to provide the title compound (9.02 g). A second crop (1.62 g) was obtained from the filtrate. $^1$H NMR (500 MHz, CDCl$_3$) δ ppm: 10.54 (1H, s), 4.44 (2H, q, J=7.0 Hz), 4.00 (4H, m), 2.00 (2H, m), 1.92 (2H, m), 1.42 (3H, t, J=7.0 Hz), 0.85 (6H, t, J=7.3 Hz). $^{13}$C NMR (500 CDCl$_3$) δ ppm: 169.53, 157.82, 151.40, 147.58, 125.35, 87.27, 62.62, 58.35, 43.24, 31.06, 14.17, 7.79. HRMS [M+H]$^+$ calcd for C$_{14}$H$_{21}$N$_2$O$_5$: 297.14506; found: 297.1464.

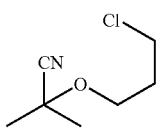

Intermediate 12

2-(3-Chloropropoxy)-2-methylpropanenitrile. Zinc chloride (68.1 g, 0.5 mol) was fused using the procedure described for the synthesis of 2-(2-chloroethoxy)-2-methylpropanenitrile. The molten zinc was cooled and the flask flushed with nitrogen. The flask was loaded with acetone cyanohydrin (46 mL, 0.5 mol) and 3-chloropropanol (64 mL, 0.75 mmol) and the reaction mixture stirred at 60° C. for 30 hours. The mixture was then diluted with water (200 mL) and extracted with dichloromethane (1×200 mL and 3×100 mL). The combined organic layers were dried (sodium sulfate), filtered, and concentrated in-vacuo. The crude product was purified by vacuum distillation (bp 78-84° C., 10 mmHg) to give the title compound (41 g) as a 2:1 mixture with residual 3-chloropropanol. $^1$H NMR (500 MHz, CDCl$_3$) δ ppm: 3.72 (2H, t, J=5.8 Hz), 3.63 (2H, t, J=6.4 Hz), 2.04 (2H, m), 1.57 (6H, br s).

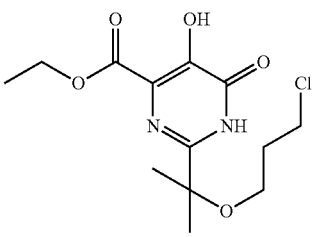

Intermediate 13

Ethyl 2-(2-(3-chloropropoxy)propan-2-yl)-5-hydroxy-6-oxo-1,6-dihydropyrimidine-4-carboxylate. A solution of 2-(3-chloropropoxy)-2-methylpropanenitrle (0.186 mol) in absolute ethanol (40 mL) was added dropwise to a cold (0° C.) solution of hydroxylamine (50% aqueous solution, 17 mL, 0.278 mol), 20 mL H$_2$O, sodium carbonate (9.91 g, 0.093 mol) and sodium iodide (2.80 g, 0.019 mol) over 15 minutes. (In an alternative procedure, sodium carbonate was omitted from the mixture). The mixture was stirred at room temperature for 30 min, then additional hydroxylamine (17 mL, 0.278 mol) was added. The reaction was then heated at 80° C. for 16 hours. The mixture was concentrated to a thick paste which was azeotroped under vacuum with ethanol/water (1:1, 100 mL). The resulting residue was taken up in ethanol/water (1:1, 200 mL), cooled (0° C.), and treated with diethyl acetylenedicarboxylate (30.1 mL, 0.188 mol) by dropwise addition over 10 min. The reaction was allowed to stir at room temperature for 2.5 hours, then diluted with water (300 mL) and ethyl acetate (300 mL). The separated organic layer was washed with water (100 mL) and brine (100 mL), then dried (sodium sulfate), filtered and concentrated in-vacuo. The crude product was purified by silica gel column chromatography, eluting with 10% to 40% ethyl acetate in hexanes, to give 21.2 g of a yellow oil. A solution of this oil (15.6 g) in 1,2,4-trimethylbenzene (300 mL) was heated at reflux (180° C.) for 2.5 hours after which the solvent was removed in-vacuo. The resulting oil was taken up in ethyl acetate (300 mL) and extracted with saturated aqueous sodium bicarbonate (1×200 mL, then 4×100 mL). The combined aqueous layers were acidified to pH 1-2 using 6 N HCl then extracted with ethyl acetate (3×150 mL). The organic extracts were dried (sodium sulfate), filtered, then concentrated in vacuo. The resulting oil was triturated with diethyl ether (50 mL) and the resulting solid collected by filtration and washed with a small volume of ether to afford the title compound (2.05 g). A second crop (0.70 g) was obtained from the filtrate. $^1$H NMR (500 MHz, CDCl$_3$) δ ppm: 10.83 (1H, br), 10.02 (1H, br), 4.46 (2H, q, J=7.0 Hz), 3.66 (2H, t, J=6.1 Hz), 3.58 (2H, t, J=5.8 Hz), 2.06 (2H, m), 1.55 (6H, s), 1.44 (3H, t, J=7.0 Hz).

Intermediate 14

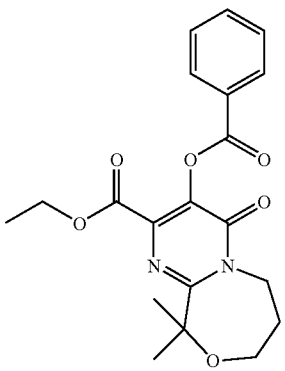

Ethyl 3-(benzoyloxy)-10,10-dimethyl-4-oxo-6,7,8,10-tetrahydro-4H-pyrimido[2,1-c][1,4]oxazepine-2-carboxylate. A solution of ethyl 2-(2-(3-chloropropoxy)propan-2-yl)-5-hydroxy-6-oxo-1,6-dihydropyrimidine-4-carboxylate, (0.064 g, 0.2 mmol) in pyridine (1 mL) was treated with benzoic anhydride (0.047 g, 0.2 mmol) and stirred for 1 hr at 60° C. The solvent was removed and the residue taken up in N,N-dimethylformamide (1 mL) and treated with potassium carbonate (0.036 g, 0.2 mmol). The mixture was stirred for 1 hr at 80° C., and solvent was removed to give the title compound.

Intermediate 15

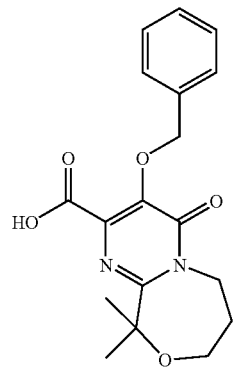

3-(Benzyloxy)-10,10-dimethyl-4-oxo-6,7,8,10-tetrahydro-4H-pyrimido[2,1-c][1,4]oxazepine-2-carboxylic acid. A suspension of ethyl 2-(2-(3-chloropropoxy)propan-2-yl)-5-hydroxy-6-oxo-1,6-dihydropyrimidine-4-carboxylate, (0.205 g, 0.64 mmol) and anhydrous potassium carbonate (0.361 g, 2.6 mmol) in anhydrous dimethylformamide (4 mL) was stirred at 60° C. for 5 hours. The reaction mixture was treated with benzyl bromide (0.122 g, 0.71 mmol) and stirred for 16 hours. Following this, 2 mL of $H_2O$ was added and the mixture stirred for an additional 24 hours. Solvent was removed by rotary evaporator and the resulting residue suspended in 0.5 N hydrochloric acid (16 mL). The crude product was extracted with ethyl acetate (2×15 mL), then dried (sodium sulfate), filtered, and concentrated to dryness by rotary evaporator to give 0.299 g (Yield>100%) of the title compound as a solid. LC/MS [M+H]$^+$=345.21.

Intermediate 16

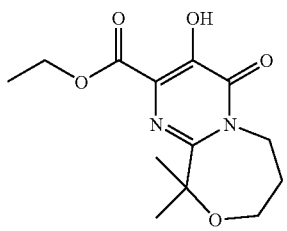

3-Hydroxy-10,10-dimethyl-4-oxo-6,7,8,10-tetrahydro-4H-pyrimido[2,1-c][1,4]oxazepine-2-carboxylate. A solution of ethyl 2-(2-(3-chloropropoxy)propan-2-yl)-5-hydroxy-6-oxo-1,6-dihydropyrimidine-4-carboxylate, (7.01 g, 22 mmol) and anhydrous potassium carbonate (9.12 g, 66 mmol) in anhydrous dimethylformamide (50 mL) was stirred at 80° C. for 20 hours. Solvent was removed by rotary evaporator and the residue, dissolved in water (50 mL), was brought to pH 1 using 6.0 N HCl. The solution was extracted with ethyl acetate (4×25 mL). The combined organic layers were dried (sodium sulfate) and filtered. The solvent was removed by rotary evaporator to give the title compound (5.53 g, Yield 89%) as a brown solid: $^1$H NMR (500 MHz, CDCl$_3$) δ ppm 10.49 (1H, s), 4.56 (2H, br), 4.43 (2H, q, J=7.2 Hz), 3.69 (2H, t, J=6.4 Hz), 1.93-1.99 (2H, m), 1.61 (6H, s), 1.42 (3H, t, J=7.2 Hz); $^{13}$C NMR (126 MHz, CDCl$_3$) δ ppm 169.33, 158.30, 153.39, 148.73, 124.45, 82.85, 62.60, 60.71, 38.79, 27.67, 27.35, 14.15; HRMS (ESI) calcd for $C_{13}H_{19}N_2O_5$ (M+H) 283.1294, found 283.1305.

Intermediate 17

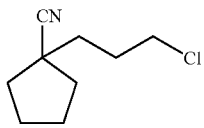

1-(3-Chloropropyl)cyclopentanecarbonitrile. To a stirred solution of cyclopentanecarbonitrile (1.04 mL, 10 mmol) in THF (20 mL) at −78° C. was added LiHMDS (1M in THF, 11 mL) via syringe. After 30 min, 1-chloro-3-iodopropane (1.6 mL, 15 mmol) was added at once and slowly warmed to room temperature. After 20 h, the reaction mixture was quenched with saturated ammonium chloride (1 mL), diluted with EtOAc (100 mL), dried (MgSO$_4$), filtered and concentrated to give the title compound as a yellow oil which was used in the next step without further purification.

Intermediate 18

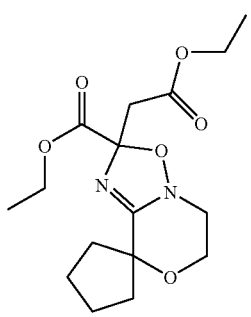

Ethyl 2-(2-ethoxy-2-oxoethyl)-2,5,6,7-tetrahydrospiro[[1,2,4]oxadiazolo[2,3-a]pyridine-8,1'-cyclopentane]-2-carboxylate. To a stirred mixture of 1-(3-chloropropyl) hydroxylamine hydrochloride (1.39 g, 20 mmol) in 1:1 EtOH/water (30 mL) was added sodium carbonate (1.6 g, 15 mmol) over 5 min. Then, the reaction mixture was stirred to 80° C. for 15 h and concentrated to dryness. The resulting white residue was re-dissolved into 1:1 EtOH/water (30 mL) and diethyl acetylenedicarboxylate (2.4 mL, 15 mmol) was added. After 1 h, the reaction mixture was diluted with water (50 mL) and extracted with EtOAc (3×50 mL). The combined EtOAc extracts dried (Na$_2$SO$_4$), filtered and concentrated to give brown oil. Flash chromatography using 9:1, 4:1 and 7:1 Hexanes/EtOAc mixtures afforded the title compound as a pale yellow oil (1.03 g, 30%). $^1$H NMR (500 MHz, CDCl$_3$) δ: 4.34-4.11 (4H, m), 3.50-3.46 (1H, m), 3.38-3.34 (1H, m), 3.31 (1H, d, J=16.2 Hz), 2.91 (1H, d, J=16.2 Hz), 2.23-2.13 (2H, m), 1.95-1.89 (2H, m), 1.74-1.69 (2H, m), 1.62 (2H, t, J=5.9 Hz), 1.54-1.48 (2H, m), 1.34-1.23 (8H, m). HRMS (M+H) calcd for C$_{17}$H$_{27}$N$_2$O$_5$: 339.1920; found: 339.1923.

Intermediate 19

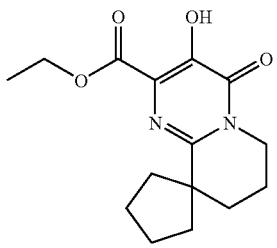

Ethyl 3'-hydroxy-4'-oxo-4',6',7',8'-tetrahydrospiro[cyclopentane-1,9'-pyrido[1,2-a]pyrimidine]-2'-carboxylate. A solution of ethyl 2-(2-ethoxy-2-oxoethyl)-2,5,6,7-tetrahydrospiro[[1,2,4]oxadiazolo[2,3-a]pyridine-8,1'-cyclopentane]-2-carboxylate (1.0 g, 2.955 mmol) in 3,4-dichlorotoluene (10 mL) was heated at 210° C. for 15 h. Then, the reaction mixture was concentrated under vacuum and the residue was purified by preparative HPLC using MeOH/water containing 0.1% TFA (gradient elution). The fractions containing the product were combined and concentrated to afford the title compound as a dark paste (0.8639 g, 28.6%). $^1$H NMR (500 MHz, CDCl$_3$) δ: 10.75 (1H, br s), 4.43 (2H, q, J=7.0 Hz), 4.03 (2H, t, J=5.8 Hz), 2.25-2.20 (2H, m), 1.99-1.93 (4H, m), 1.79-1.64 (6H, m), 1.42 (3H, t, J=7.0 Hz), HRMS (M+H) calcd for C$_{15}$H$_{21}$N$_2$O$_4$: 293.1501; found: 293.1513.

Intermediate 20

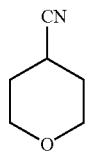

Tetrahydro-2H-pyran-4-carbonitrile. A solution of tetrahydro-4H-pyran-4-one (25 g, 250 mmol) and toluenesulfonylmethyl cyanide (53.7 g, 275 mmol) dissolved in ethylene glycol dimethylether (1 L) was cooled to 0° C. Added dropwise over 30 min was a solution of potassium t-butoxide (56 g, 500 mmol) dissolved in t-butanol (350 mL) and ethylene glycol dimethylether (150 mL). After stirring the resulting mixture for 3 h at room temp, diethyl ether (1 L) was added and the organic phase was washed with saturated aqueous NaHCO$_3$. The organic phase was dried (Na$_2$SO$_4$) and concentrated. The residue was distilled at 39° C. 1.7 mm Hg to give the title compound as a colorless oil (10.87 g, 39% yield). $^1$H NMR (300 MHz, CDCl$_3$) δ: 3.91-3.83 (2H, m), 3.61-3.54 (2H, m), 2.89-2.80 (1H, m), 1.97-1.78 (4H, m).

Intermediate 21

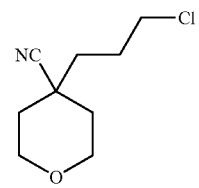

4-(3-Chloropropyl)-tetrahydro-2H-pyran-4-carbonitrile. To a stirred solution of 1 M LiHMDS (25 mL, 25 mmol) in THF (10 mL) at −78° C. was added dropwise a solution of tetrahydro-2H-pyran-4-carbonitrile (2.23 g, 20 mmol) in THF (15 mL) over 10 minutes. After 40 min, 1-chloro-3-iodopropane (2.7 mL, 25 mmol) was added at once, stirred at −78° C. for 1 h and 4 h room temperature. Then the reaction mixture was diluted with ether (100 mL), washed with water (20 mL) and brine (20 mL), dried (Na$_2$SO$_4$), filtered and concentrated to give yellow oil which was purified by flash column chromatography using 10-30% EtOAc/Hexanes to afford the title compound as a colorless liquid (3.74 g, 99%). $^1$H NMR (500 MHz, CDCl$_3$) δ: 3.97 (2H, dd, J=11.3, 3.7 Hz), 3.71 (2H, td, J=12.2, 1.8 Hz), 3.61 (2H, t, J=6.3 Hz), 2.05-1.98 (2H, m), 1.88 (2H, dd, J=13.4, 1.8 Hz), 1.77-1.74 (2H, m), 1.65-1.59 (2H, m).

Intermediate 22

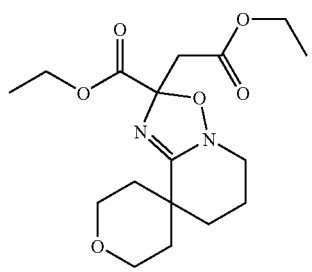

Ethyl 2-(2-ethoxy-2-oxoethyl)-2,2',3',5,5',6,6',7-octahydrospiro[[1,2,4]oxadiazolo[2,3-a]pyridine-8,4'-pyran]-2-carboxylate. A mixture of 4-(3-chloropropyl)-tetrahydro-2H-pyran-4-carbonitrile (1.83 g, 9.75 mmol) and NaI (3.0 g, 20 mmol) was stirred at ambient temperature for 1 h. To this reaction mixture was added 50% aqueous hydroxylamine (1 mL, 10.87 mmol) and stirred for three-days at ambient temperature. To this was added diethyl acetylenedicarboxylate (1.6 mL, 10 mmol) and stirred for 1 h. Then, the reaction mixture was diluted with EtOAc (100 mL) washed with water (50 mL), brine (10 mL), dried (Na$_2$SO$_4$), filtered and concentrated to give yellow oil. Flash chromatography using 10-50% EtOAc/Hexanes afforded the title compound as pale yellow oil (0.627 g, 18%). $^1$H NMR (500 MHz, CDCl$_3$) δ: HRMS (M+H) calcd for C$_{17}$H$_{27}$N$_2$O$_5$; found. $^1$H NMR (500 MHz, CDCl$_3$) δ: 4.32-4.20 (2H, m), 4.14 (2H, q, J=7.0 Hz), 3.86 (1H, td, J=11.0, 2.7 Hz), 3.79-3.70 (3H, m), 3.52-3.46 (1H, m), 3.38-3.34 (1H, m), 3.26 (1H, d, J$_{AB}$=16.2 Hz), 2.97 (1H, d, J$_{AB}$=16.2 Hz), 2.06-1.89 (4H, m), 1.66-1.66 (2H, m), 1.60-1.53 (2H, m), 1.30 (3H, t, J=7.0 Hz), 1.24 (3H, t, J=7.0 Hz).

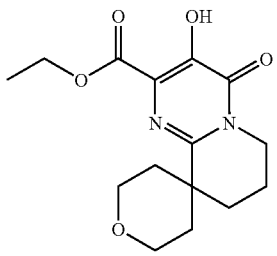

Intermediate 23

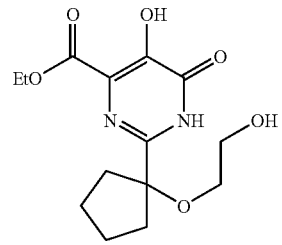

Intermediate 25

Ethyl 3'-hydroxy-4'-oxo-2,3,4',5,6,6',7',8'-octahydrospiro[pyran-4,9'-pyrido[1,2-a]pyrimidine]-2'-carboxylate A solution of ethyl 2-(2-ethoxy-2-oxoethyl)-2,2',3',5,5',6,6',7-octahydrospiro[[1,2,4]oxadiazolo[2,3-a]pyridine-8,4'-pyran]-2-carboxylate (1.0 g, 2.955 mmol) in cyclohexylbenzene (25 mL) was heated at 200° C. for 15 h. Then, the reaction mixture was concentrated under vacuum and the residue was purified by preparative HPLC using MeOH/water containing 0.1% TFA (gradient elution). The fractions containing the product were combined and concentrated to afford the title compound as an off-white solid (0.126 g, 23%). $^1$H NMR (500 MHz, CDCl$_3$) δ: 10.35 (1H, br s), 4.45 (2H, q, J=7.0 Hz), 4.09-4.05 (2H, m), 4.01-3.99 (2H, m), 3.74-3.69 (2H, m), 2.35-2.29 (2H, m), 2.02-1.93 (4H, m), 1.59-1.54 (2H, m), 1.44 (3H, t, J=7.0 Hz). HRMS (M+H) calcd for C$_{15}$H$_{21}$N$_2$O$_4$: 309.1451; found: 309.1463.

5-Hydroxy-2-[3-(2-hydroxy-ethoxy)tetrahydrofuran-3-yl]-6-oxo-1,6-dihydropyrimidine-4-carboxylic acid ethyl ester. A xylenes (200 ml) solution of (E)-2-{[1-(2-hydroxyethoxy)cyclopentanecarboximidoyl]-aminooxy}but-2-enedioic acid diethyl ester (100 mmol) was heated at reflux for 24 h, cooled and concentrated. The resulting dark-residue was stirred with 0.5 M Na$_2$CO$_3$ (150 mL) for 30 min and extracted with EtOAc (3×50 mL). The combined organic phases were re-extracted with 0.5 M Na$_2$CO$_3$ (50 mL) and EtOAc extracts discarded. The combined aqueous layers were carefully acidified with conc. HCl (20 mL) and extracted with CH$_2$Cl$_2$ (4×50 mL). The combined CH$_2$Cl$_2$ layers dried (Na$_2$SO$_4$/activated charcoal), filtered and concentrated to give brown solid which triturated with ether and filtered to afford the title as a light brown powder (11.81 g, 38%). This material is contaminated with about 15% of an identified impurity whose M+1=295. LRMS (M+H) calcd for C$_{14}$H$_{21}$N$_2$O$_6$: 313.32; found: 313.27.

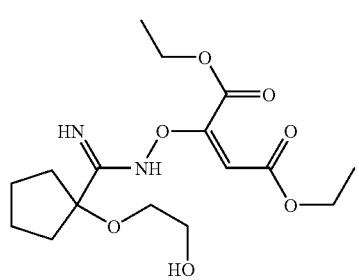

Intermediate 24

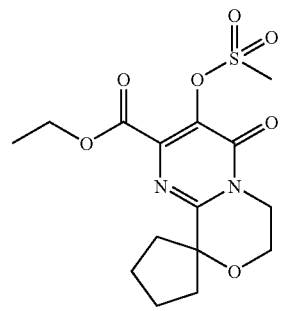

Intermediate 26

(E)-2-{[1-(2-Hydroxyethoxy)cyclopentanecarboximidoyl]-aminooxy}but-2-enedioic acid diethyl ester. A stirred mixture of cyclopentanone ethylene ketal (12.82 g, 100 mmol) and ZnI$_2$ (45 mg, catalytic) was placed in water bath and to this was added trimethylsilyl cyanide (13.35 mL, 100 mmol) via syringe over 10 min. After 16 h, EtOH (100 mL) followed by 50% aqueous hydroxylamine (6.43 mL, 100 mmol) was added and stirred at 80° C. for 2 h. Then, the reaction mixture was cooled in ice-water bath and diethyl acetylenedicarboxylate (16 mL, 100 mmol) was added over 5 min. The cooling bath was removed and the reaction stirred for 4 h at room temperature then concentrated to give the title compound as a dark-brown oil LRMS (M+H) calcd for C$_{16}$H$_{27}$N$_2$O$_7$: 359.2; found: 359.2.

Ethyl 3'-(methylsulfonyloxy)-4'-oxo-6',7'-dihydro-4'H-spiro[cyclopentane-1,9'-pyrimido[2,1-c][1,4]oxazine]-2'-carboxylate. To a stirred solution of 5-hydroxy-2-[3-(2-hydroxy-ethoxy)tetrahydrofuran-3-yl]-6-oxo-1,6-dihydropyrimidine-4-carboxylic acid ethyl ester (11.67 g) in THF (100 mL) at 5° C. was added MsCl (8.7 mL, 112.4 mmol) followed by Et$_3$N (15.8 mL, 112.5 mmol). The resulting turbid reaction mixture was stirred for 4 h while allowing it to warm to room temperature. Then diluted with EtOAc (200 mL), washed with water (2×50 mL), brine (50 mL), dried (Na$_2$SO$_4$), filtered and concentrated to give viscous yellow oil. This oil was re-dissolved in anhydrous EtOH (100 mL) and stirred with K$_2$CO$_3$ (4.15 g, 30 mmol). After 4 h, the viscous slurry was diluted with EtOAc (150 mL) and continued stirring for additional 1 h. Then, the reaction mixture was filtered and concentrated to give white solid which was triturated with ether, and filtered to afford the title compound as a white fluffy solid (8.28 g, 64%). $^1$H NMR (500 MHz, CDCl$_3$) δ: 4.43 (2H, q, J=7.0 Hz), 3.99 (4H, s), 3.53 (3H, s), 2.33-2.28

(2H, m), 2.09-2.05 (2H, m), 1.93-1.82 (4H, m), 1.40 (3H, t, J=7.0 Hz). HRMS (M+H) calcd for $C_{15}H_{21}N_2O_7S$: 373.1069; found: 373.1053.

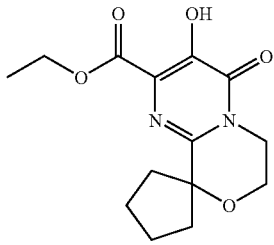

Intermediate 27

Ethyl 3'-hydroxy-4'-oxo-6',7'-dihydro-4'H-spiro[cyclopentane-1,9'-pyrimido[2,1-c][1,4]oxazine]-2'-carboxylate. To a stirred suspension of ethyl 3'-(methylsulfonyloxy)-4'-oxo-6',7'-dihydro-4'H-spiro[cyclopentane-1,9'-pyrimido[2,1-c][1,4]oxazine]-2'-carboxylate (0.6861 g, 1.84 mmol) in THF (50 mL) was added 1M EtONa/EtOH (10 mL). After 1 h, the resulting yellow solution was concentrated, acidified with 1 M aq. HCl (20 mL), extracted with $CH_2Cl_2$ (3×35 mL). The combined organic layers dried (Na2SO4), filtered and concentrated to give the title compound as a brown solid (0.4668 g, 86%). $^1$H NMR (500 MHz, $CDCl_3$) δ: 10.49 (1H, s), 4.44 (2H, q, J=7.0 Hz), 4.03-3.97 (4H, m), 2.28-2.22 (2H, m), 2.06-2.01 (2H, m), 1.93-1.81 (4H, m), 1.42 (3H, t, J=7.0 Hz). HRMS (M+H) calcd for $C_{14}H_{19}N_2O_5$: 295.1294; found: 295.1293.

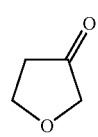

Intermediate 28

Dihydrofuran-3(2H)-one. A mixture of 3-hydroxyfuran (24 g, 272 mmol) and TEMPO (0.86 g, 5.5 mmol) in $CH_2Cl_2$ (175 mL) and KBr (7.141 g, 60 mmol) in water was vigorously stirred and cooled in an ice-water bath. The pH of NaOCl (commercial grade bleach, 600 mL, 806 mmol) was adjusted to 9.5 by dissolving $NaHCO_3$ (8.632 g, 102.75 mmol) immediately before use. This NaOCl solution was added over 40 min while keeping the internal temperature of the reaction mixture between 0° C. and 5° C. After 2 h, the greenish-yellow organic phase was separated and aqueous phase was saturated with NaCl and extracted with $CH_2Cl_2$ (4×100 mL). The combined organic phases were washed with 10% HCl aq. (1×300 mL) containing KI (12 g) and 10% aq. $Na_2CO_3$ (2×150 mL). The organic layer dried (Na2SO4), filtered and concentrated to give the title compound as a pale yellow liquid (15.79 g, 67). $^1$H NMR (500 MHz, $CDCl_3$) δ: 4.24 (2H, t, J=7.3 Hz), 3.86 (2H, s), 2.49 (2H, t, J=7.3 Hz).

Intermediate 29

1,4,7-Trioxaspiro[4.4]nonane. A mixture of ethyl 3'-hydroxy-4'-oxo-6',7'-dihydro-4'H-spiro[cyclopentane-1,9'-pyrimido[2,1-c][1,4]oxazine]-2'-carboxylate (15.79 g, 183.5 mmol), ethylene glycol (16.7 mL, 300 mmol) and cat. $TsOH.H_2O$ (100 mg) in benzene (100 mL) was heated at reflux using Dean-Stark trap. After 17 h, the reaction mixture was cooled, diluted with ether (150 mL), washed with sat. $Na_2CO_3$ and brine (50 mL each), dried ($Na_2SO_4$), filtered and concentrated to give yellow liquid. Distillation under reduced pressure afforded the title compound as a yellow liquid (19.13 g, 80%). $^1$H NMR (500 MHz, $CDCl_3$) δ: 3.9.4 (2H, t, J=7.0 Hz), 3.94-3.90 (4H, m), 3.68 (2H, s), 2.09 (2H, t, J=7.0 Hz).

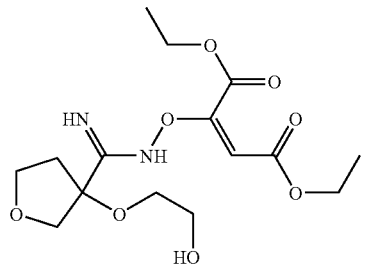

Intermediate 30

(E)-2-{[3-(2-Hydroxy-ethoxy) tetrahydrofuran-3-carboximidoyl]-aminooxy}but-2-enedioic acid diethyl ester. $^1$H NMR (500 MHz, $CDCl_3$) δ: 5.78 (1H, d, J=7.6 Hz), 5.59 (1H, br s), 5.38 (1H, s), 4.37-4.27 (2H, m), 4.20-4.13 (2H, m), 4.03-3.87 (4H, m), 3.79-3.75 (2H, m), 3.53-3.45 (2H, m), 1.60 (1H, br s), 1.38-1.23 (6H, m). HRMS (M+H) calcd for $C_{15}H_{25}N_2O_8$: 361.1611; found: 361.1620.

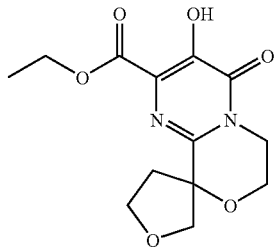

Intermediate 31

Ethyl 3'-hydroxy-4'-oxo-4,5,6',7'-tetrahydro-2H,4'H-spirofuran-3,9'-pyrimido[2,1-c][1,4]oxazine]-2'-carboxylate. Yield: 29%; brown solid. $^1$H NMR (500 MHz, $CDCl_3$) δ: 10.63 (1H, br s), 4.44 (2H, q, J=7.0 Hz), 4.18-4.11 (4H, m), 4.08-4.01 (4H, m), 2.66-2.60 (1H, m), 2.35-2.30 (1H, m), 1.41 (3H, t, J=7.0 Hz). HRMS (M+H) calcd for $C_{13}H_{17}N_2O_6$: 297.1087; found: 297.1071.

Intermediate 32

1,4,8-Trioxa-spiro[4.5]decane. A mixture of tetrahydro-4-pyranone (10 g, 99.9 mmol), ethylene glycol (20 mL, 150 mmol) and catalytic toluene sulfonic acid was refluxed in benzene (120 mL) for 5 h. After cooling to room temp, the benzene layer was decanted from the dark oil in the bottom of the flask and was concentrated. The resulting oil was taken up in methylene chloride and shaken in a separatory funnel. The CH$_2$Cl$_2$ layer was decanted from the insoluble oil. The CH$_2$Cl$_2$ layer was concentrated to give the title compound as a pale yellow oil (11.62 g, 81% yield). $^1$H-NMR (300 MHz, CDCl$_3$) δ: 3.91 (4H, s), 3.71 (4H, t, J=5.5 Hz), 1.68 (4H, t, J=5.7 Hz).

Intermediate 33

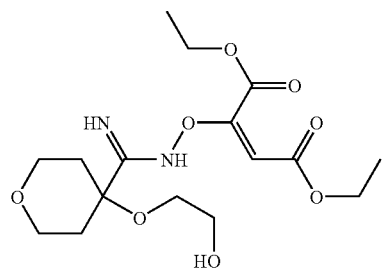

(E)-2-{[4-(2-Hydroxyethoxy)tetrahydropyran-4-carboximidoyl]-aminooxy}but-2-enedioic acid diethyl ester $^1$H-NMR (300 MHz, CDCl$_3$) δ: 5.72 (1H, d, J=22.7 Hz), 5.50 (1H, bs), 5.29 (1H, bs), 4.33-4.23 (2H, m), 4.19-4.04 (2H, m), 3.95-3.87 (1H, m), 3.79-3.63 (6H, m), 3.43-3.39 (2H, m), 2.15-1.74 (4H, m), 1.35-1.19 (6H, m). LCMS [M+H]$^+$ calcd for C$_{16}$H$_{27}$N$_2$O$_8$: 375.17; found: 375.19.

Intermediate 34

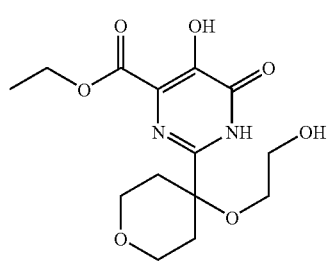

5-Hydroxy-2-[4-(2-hydroxyethoxy) tetrahydropyran-4-yl]-6-oxo-1,6-dihydropyrimidine-4-carboxylic acid ethyl ester. A solution of (E)-2-{[4-(2-hydroxyethoxy)tetrahydropyran-4-carboximidoyl]-aminooxy}but-2-enedioic acid diethyl ester (9.3 g, 25 mmol) in xylenes (150 mL) was refluxed for 18 h. After cooling to room temp, the mixture was shaken with 0.2 M Na$_2$CO$_3$. The aqueous phase was washed with EtOAc, made acidic with conc'd HCl and extracted with CH$_2$Cl$_2$. The organic phase was dried (Na$_2$SO$_4$) and concentrated. The resulting residue was triturated with ether to give the title compound as a brown solid (0.87 g, 10% yield) and impure product (2.36 g). LCMS [M+H]$^+$ calcd for C$_{14}$H$_{21}$N$_2$O$_7$: 329.13; found: 329.15.

Intermediate 35

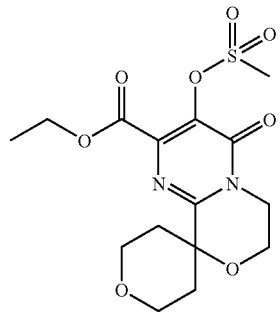

Ethyl 3'-(methylsulfonyloxy)-4'-oxo-2,3,5,6,6',7'-hexahydro-4'H-spiro[pyran-4,9'-pyrimido[2,1-c][1,4]oxazine]-2'-carboxylate. A solution of 5-hydroxy-2-[4-(2-hydroxyethoxy)tetrahydropyran-4-yl]-6-oxo-1,6-dihydropyrimidine-4-carboxylic acid ethyl este (0.86 g, 2.6 mmol) in THF (10 mL) was cooled to 0° C. Added to this was methanesulfonyl chloride (0.613 mL, 7.9 mmol) followed by slow addition of triethylamine (1.07 mL, 7.9 mmol). The mixture stirred for 4 h while gradually warming to room temp. before diluting with EtOAc. The mixture was washed with water and brine and dried (Na$_2$SO$_4$) before concentrating to give a dark oil. This was dissolved in EtOH (20 mL) and THF (10 mL) and added potassium carbonate (0.56 g, 4.04 mmol). The mixture was stirred at room temp for 18 h, diluted with EtOAc (200 mL) and the solids were removed by filtration. The solution was concentrated and the residue was triturated with methanol. Filtration gave the title compound as a white solid (0.23 g, 23%). $^1$H-NMR (300 MHz, CDCl$_3$) δ: 4.41 (2H, q, J=7.2 Hz), 4.03-3.98 (4H, m), 3.88-3.82 (2H, m), 3.74 (2H, t, J=11.2 Hz), 3.50 (3H, s), 2.44 (2H, dt, J=13.1, 4.9 Hz), 1.76 (2H, d, J=13.9 Hz), 1.38 (3H, t, J=7.1 Hz). LCMS [M+H]$^+$ calcd for C$_{15}$H$_{21}$N$_2$O$_8$S$_3$: 389.10; found: 389.13.

Intermediate 36

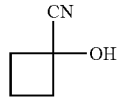

1-Hydroxycyclobutanecarbonitrile. To a flask containing cyclobutanone (13.41 g, 191 mmol) was added a solution of potassium phosphate monobasic (29.10 g, 214 mmol) in water (50 mL), followed by a solution of sodium cyanide (10.39 g, 210 mmol) in water (50 mL), and the reaction was stirred for 16 hours. The reaction was treated with diethyl ether (100 mL) and stirred for 30 minutes. The separated aqueous layer was washed with ether (2×100 mL), and the combined extracts were concentrated to an oil. The oil was dissolved in dichloromethane, dried (sodium sulfate), filtered, and concentrated to give an amber oil (15.10 g), which contained approximately 15% of the title compound. $^1$H NMR (500 MHz, CDCl$_3$) δ: 3.15 (1H, br s), 2.60-2.68 (2H, m), 2.29-2.38 (2H, m), 1.89-2.03 (2H, m).

Intermediate 37

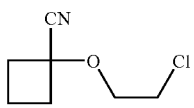

1-(2-Chloroethoxy)cyclobutanecarbonitrile. Zinc chloride (36.03 g, 264 mmol) was fused using a propane torch while under vacuum. The molten salt was cooled and the evacuated flask was flushed with nitrogen. The flask was loaded with 1-hydroxycyclobutanecarbonitrile (15.10 g,) and 2-chloroethanol (17.7 g, 218 mmol) and stirred with heating (90° C.) for 20 hours. The reaction mixture was diluted with water (200 mL) and extracted with ethyl acetate (1×150 mL, 4×100 mL). The combined organic layers were dried (sodium sulfate), filtered, and concentrated to an oil in-vacuo. The crude product was purified by vacuum distillation (b.p.$_{12}$ 85° C.) to give title compound (5.00 g, 31.3 mmol, 16.4% over two steps) as a clear liquid. $^1$H NMR (500 MHz, CDCl$_3$) δ: 3.75 (2H, t, J=5.5 Hz), 3.65 (2H, t, J=5.6 Hz), 2.52-2.61 (2H, m), 2.31-2.43 (2H, m), 1.91-2.06 (2H, m).

Intermediate 38

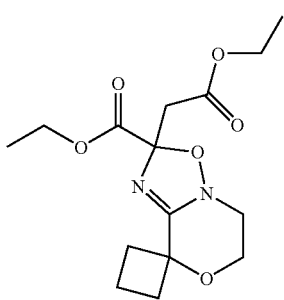

Ethyl 2-(2-ethoxy-2-oxoethyl)-5,6-dihydro-2H-spiro[[1,2,4]oxadiazolo[3,2-c][1,4]oxazine-8,1'-cyclobutane]-2-carboxylate. A solution of 1-(2-chloroethoxy)cyclobutanecarbonitrile (2.64 g, 16.5 mmol) in ethanol (10 mL) was treated with a 50 weight-percent aqueous solution of hydroxylamine (3.34 g, 50 mmol), and stirred with heating (60° C.) for 16 hours. The solvent was removed in vacuo, and the residue was dried from ethanol-water (1:1, 10 mL) twice, to give an oily solid.

A cold (0° C.) solution of the above oily solid in ethanol (5 mL) and water (10 mL) was treated with a solution of diethyl acetylenedicarboxylate (4.22 g, 25 mmol) in ethanol (50 mL). The reaction was stirred for 5 minutes, then warmed to room temperature, and stirred for 2 hours. The reaction was diluted with water (50 mL) and extracted with ethyl acetate (3×50 mL). The combined extracts were dried (sodium sulfate), filtered, and concentrated in vacuo. The crude mixture was partially purified by flash silica gel column chromatography, eluting with 10% to 35% ethyl acetate in hexanes. Product fractions were pooled and concentrated in vacuo to give title compound (2.58 g, 48%) as a yellow oil. LC/MS [M+H]$^+$= 327.14.

Intermediate 39

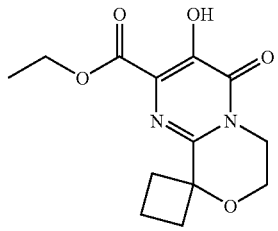

Ethyl 3'-hydroxy-4'-oxo-6',7'-dihydro-4'H-spiro[cyclobutane-1,9'-pyrimido[2,1-c][1,4]oxazine]-2'-carboxylate. A solution of ethyl 2-(2-ethoxy-2-oxoethyl)-5,6-dihydro-2H-spiro[[1,2,4]oxadiazolo[3,2-c][1,4]oxazine-8,1'-cyclobutane]-2-carboxylate (2.51 g, 7.7 mmol) in 1,2,4-trimethyl benzene (25 mL) was heated at reflux (180° C.) for 3 hours, then cooled to room temperature. The solvent was removed in vacuo, and the crude was dissolved in ethyl acetate (75 mL) and extracted with a saturated aqueous solution of sodium bicarbonate (4×75 mL). The combined extracts were brought to pH 1-2 using 6N hydrochloric acid, and the resultant solid was extracted with ethyl acetate (4×50 mL). The combined extract was dried (sodium sulfate), filtered, and concentrated in vacuo to give the title compound (0.235 g, 5.2% over two steps) as a brown solid. $^1$H NMR (500 MHz, CDCl$_3$) δ: 10.54 (1H, s), 4.46 (2H, q, J=7.1 Hz), 3.95-4.00 (4H, m), 2.67-2.74 (2H, m), 2.30 (2H, ddd, J=12.4, 9.9, 7.3 Hz), 2.09-2.19 (1H, m), 1.97-2.06 (1H, m), 1.44 (3H, t, J=7.2 Hz). LC/MS [M+H]$^+$=281.11.

Alternative Preparation of Intermediate 39 from Cyclobutanone.

Intermediate 40

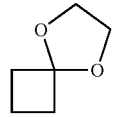

5,8-Dioxa-spiro[3.4]octane. A solution of cyclobutanone (7.7 g, 0.11 mol), ethylene glycol (6.82 g, 0.11 mol) and p-toluenesulfonic acid mono hydrate (200 mg, 1 mmol) in benzene (200 mL) was heated at reflux with a Dean-Stark trap for 14 hrs. After cooling, the mixture was washed with aqueous sodium bicarbonate solution (saturated, 15 mL), then with brine and dried (magnesium sulfate), filtered and concentrated to obtain 9.37 g (82%) of the title compound as a colorless liquid: $^1$H NMR (CDCl$_3$, 500 MHz) δppm 3.87 (4H, s, CH$_2$), 2.31 (4H, t, J=8 Hz, CH$_2$), 1.67 (2H, qt, J=8 Hz, CH$_2$); $^{13}$C NMR (CDCl$_3$, 125.77 Hz) δ: 109.08 (C), 63.87 (CH$_2$), 35.58 (CH$_2$), 11.42 (CH$_2$).

Intermediate 41

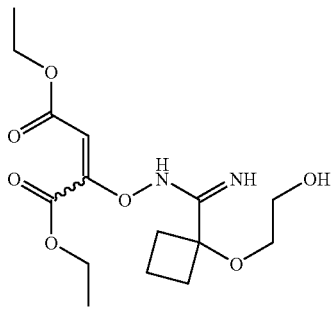

2-{[1-(2-Hydroxyethoxy)cyclobutanecarboximidoyl]-aminooxy}but-2-enedioic acid diethyl ester. To a mixture of 5,8-dioxa-spiro[3.4]octan (5.70 g, 50 mmol) and trimethylsilyl cyanide (5.05 g, 50 mmol) was added a catalytic amount of ZnI$_2$ (12 mg) in a cool water bath of ~10° C. and the mixture stirred at room temperature for 5 hrs to obtain 10.7 g of 1-(2-trimethylsilanyloxyethoxy)cyclobutanecarbonitrile as a mobile oil: $^1$H NMR (CDCl$_3$, 500 MHz) δ: 3.75 (2H, t, J=5 Hz, OCH$_2$), 3.55 (2H, t, J=5 Hz, OCH$_2$), 2.51-2.56 (2H, m, CH$_2$), 2.30-2.37 (2H, m, CH$_2$), 1.91-1.98 (2H, m, CH$_2$), 0.124 (9H, s, SiCH$_3$); $^{13}$C NMR (CDCl$_3$, 125.77 Hz) δppm 120.43 (CN), 72.05 (C), 67.71 (CH$_2$), 61.49 (CH$_2$), 34.02 (CH$_2$), 12.91 (CH$_2$), −0.29 (CH$_3$). LC/MS m/z 142 (M+H—SiMe$_3$).

A solution of 1-(2-trimethylsilanyloxyethoxy)cyclobutanecarbonitrile (3.5 g, 16.4 mmol) and 50% aqueous hydroxylamine (1.08 g, 16.4 mmol) in EtOH (16 mL) was stirred in an oil bath heated at 80° C. for 2.5 hrs and then cooled to room temperature. To this solution was added drop-wise diethyl acetylenedicarboxylate (2.93 g, 17.2 mmol) in an ice-bath and the mixture stirred at room temperature for 5 hrs. This mixture was concentrated in vacuo to obtain 6.16 g of a crude brownish oil containing the title compound: $^1$H NMR (500 MHz, CDCl$_3$) δ: 1.19-1.38 (6H, m) 1.72-1.86 (2H, m) 2.06-2.24 (2H, m) 2.29-2.49 (2H, m) 3.26-3.38 (2 H, m) 3.65-3.76 (2H, m) 4.11-4.19 (2H, m) 4.24-4.38 (2H, m) 5.67 (0.25H, s) 5.85 (0.5H, s). HRMS (M+H) calcd for C$_{15}$H$_{25}$N$_2$O$_7$ 345.1662, found 345.1648.

Intermediate 42

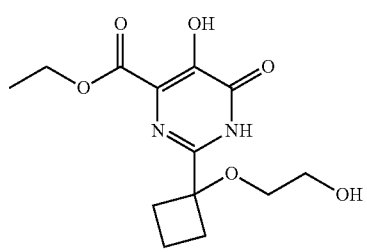

5-Hydroxy-2-[1]-(2-hydroxy-ethoxy)-cyclobutyl]-6-oxo-1,6-dihydro-pyrimidine-4-carboxylic acid ethyl ester. A solution of 2-{[1-(2-hydroxyethoxy)cyclobutanecarboximidoyl]-aminooxy}but-2-enedioic acid diethyl ester (5.9 g) in xylenes (30 mL) was heated at 150-155° C. for 20 h. The mixture was concentrated in vacuo and the residue re-dissolved in EtOAc (30 mL) was extracted with 1M aq. sodium carbonate solution (3×20 mL). The aqueous extracts were acidified with careful addition of concentrated HCl, and this mixture was extracted with CH$_2$Cl$_2$ (2×20 ml). The combined organic extracts were dried (Na$_2$SO$_4$), filtered and concentrated to obtain the title compound (1.19 g, 24% over three steps) as brownish oil: LC/MS m/z 299 (M+H).

Intermediate 43

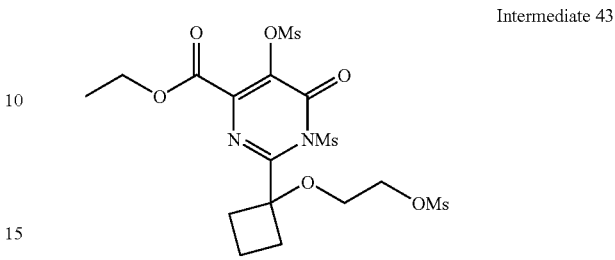

Ethyl 1-(methylsulfonyl)-5-(methylsulfonyloxy)-2-(1-(2-(methylsulfonyloxy)ethoxy)cyclobutyl)-6-oxo-1,6-dihydro-pyrimidine-4-carboxylate: A cold (0° C.) solution of 5-hydroxy-2-[1-(2-hydroxy-ethoxy)-cyclobutyl]-6-oxo-1,6-dihydro-pyrimidine-4-carboxylic acid ethyl ester (7.23 g, 25 mmol) in anhydrous tetrahydrofuran was treated with methanesulfonylchloride (Aldrich) by dropwise addition. The solution was warmed to room temperature and stirred for 4 hrs. The reaction was concentrated in-vacuo, and the crude product was dissolved in ethyl acetate (75 mL) and washed with saturated sodium bicarbonate solution. The organic solution was dried (sodium sulfate), filtered to remove solids, and concentrated in vacuo to give the title compound as a brown oil. $^1$H NMR (500 MHz, CDCl$_3$) δ: 4.49 (2H, q, J=7.0 Hz), 4.35-4.38 (2H, m), 3.93-4.00 (1H, m), 3.66-3.67 (3H, s), 3.62-3.65 (2H, m), 3.44-3.46 (3H, s), 3.05-3.07 (3H, s), 2.74-2.82 (1H, m), 2.60-2.67 (2H, m), 2.41-2.49 (2H, m), 1.43 (3H, t, J=7.0 Hz). LCMS (M+H): 532.94.

Intermediate 44

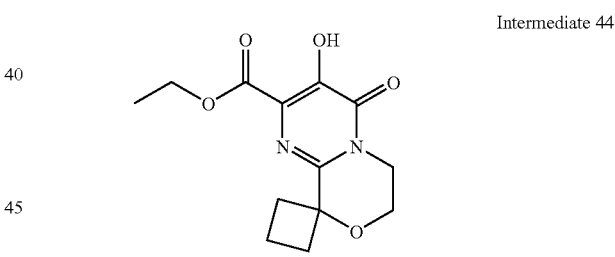

Ethyl 3'-hydroxy-4'-oxo-6',7'-dihydro-4'H-spiro[cyclobutane-1,9'-pyrimido[2,1-c][1,4]oxazine]-2'-carboxylate. To a solution of ethyl 1-(methylsulfonyl)-5-(methylsulfonyloxy)-2-(1-(2-(methylsulfonyloxy)ethoxy)cyclobutyl)-6-oxo-1,6-dihydropyrimidine-4-carboxylate obtained above in absolute ethanol (50 mL) and anhydrous tetrahydrofuran (75 mL) was added anhydrous potassium carbonate (3.46 g, 25 mmol), and the reaction was stirred with heating (65° C.) for 20 hrs. Solvent was removed in-vacuo and the crude product was dissolved in water (150 mL) and extracted with ethyl acetate (2×100 mL). The aqueous layer was made acidic (pH ~1-2) using 6.0 N hydrochloric acid, and the resulting solid was extracted with ethyl acetate (2×75 mL). The combined extract was dried (sodium sulfate), filtered to remove solids, and concentrated to give the title compound (4.30 g, 61%) as a light brown solid. $^1$H NMR (500 MHz, CDCl$_3$) δ: 10.57 (1H, s), 4.46 (2H, q, J=7.2 Hz), 3.97 (4H, s), 2.67-2.73 (2H, m), 2.27-2.33 (2H, m), 2.10-2.18 (1H, m), 1.98-2.06 (1H, m), 1.44 (3H, t, J=7.2 Hz). $^{13}$C NMR (126 MHz, CDCl$_3$) δ:

169.56, 157.68, 150.41, 148.19, 125.24, 79.09, 62.63, 58.52, 42.66, 34.72, 14.18, 13.87; LC/MS (M+H): 281.13.

Intermediate 45

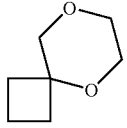

5,9-Dioxaspiro[3.5]nonane. ¹H NMR (500 MHz, C₆D₆) δ: 3.49 (4H, t, J=5.5 Hz), 2.23 (4H, t, J=8 Hz), 1.63 (2H, qt, J=8 Hz), 1.24 (2H, qt, J=5.5 Hz).

Intermediate 46

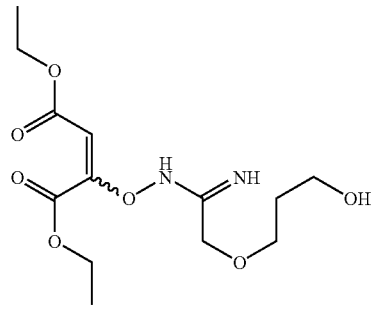

Diethyl 2-(1-(3-hydroxypropoxy)cyclobutanecarboximidamidooxy)maleat. ¹H NMR (500 MHz, C₆D₆) δ: 3.54 (2H, t, J=6.1 Hz), 3.45 (2H, t, J=6.1 Hz), 2.06-2.12 (2H, m), 1.87 (2H, dq, J=9.7, 2.6 Hz), 1.68 (2H, qt, J=6.1 Hz), 1.43-1.51 (1H, m), 1.26-1.34 (1H, m), 0.10 (9H, s). LC/MS [M+H]⁺= 359.20.

Intermediate 47

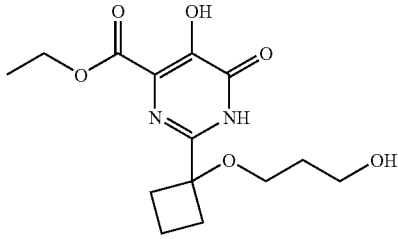

Ethyl 5-hydroxy-2-(1-(3-hydroxypropoxy)cyclobutyl)-6-oxo-1,6-dihydropyrimidine-4-carboxylate ¹H NMR (500 MHz, CDCl₃) δ: 4.46 (2H, q, J=7.0 Hz), 3.84 (2H, t, J=5.5 Hz), 3.41 (2H, t, J=5.5 Hz), 2.51-2.58 (2H, m), 2.29-2.38 (2H, m), 1.89-1.99 (2H, m), 1.82-1.90 (3H, m), 1.45 (3H, t, J=7.0 Hz), 1.31-1.41 (1H, m). LC/MS (ESI) [M+H]⁺=313.05.

Intermeidate 48

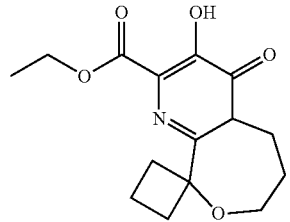

Ethyl 3'-hydroxy-4'-oxo-4a',5',6',7'-tetrahydro-4'H-spiro[cyclobutane-1,9'-oxepino[3,4-b]pyridine]-2'-carboxylate. A cold (0° C.) solution of ethyl 5-hydroxy-2-(1-(3-hydroxypropoxy)cyclobutyl)-6-oxo-1,6-dihydropyrimidine-4-carboxylate (3.0 g, 9.6 mmol) in tetrahydrofuran (25 mL) was treated with methanesulfony chloride (3.30 g, 29 mmol) followed by dropwise addition of triethylamine (4.7 mL, 33.6 mmol). The reaction was stirred for 16 hours at room temperature. The solvent was removed in vacuo and the mixture was dissolved in ethanol (50 mL) and dimethylformamide (25 mL). To the slurry was added potassium carbonate (1.36 g, 9.7 mmol) and the reaction was stirred at room temperature for 16 hours, followed by heating (80° C.) for 3 hours. The solvent was removed in vacuo. The crude product was diluted with ethyl acetate (50 mL) and washed with 1N hydrochloric acid (2×50 mL), extracted with ethyl acetate (2×25 mL) then brine ((50 mL). The solution was then dried (sodium sulfate), filtered and concentrated to give the title compound (0.534 g, 19%) as a brown solid. ¹H NMR (500 MHz, CDCl₃) δ: 10.64 (1H, br s), 4.45 (2H, q, J=7.0 Hz), 4.38 (2H, br), 3.91 (2H, t, J=5.0 Hz), 2.81 (2H, br), 2.36-2.44 (2H, m), 1.87-1.97 (1H, m), 1.82-1.86 (2H, m), 1.67-1.75 (1H, m), 1.43 (3H, t, J=7.2 Hz).

Intermediate 49

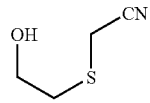

2-(2-Hydroxyethylthio)acetonitrile. To a stirred solution of 2-mercaptoethanol (17.53 mL, 250 mmol) in THF (120 mL) was added K₂CO₃ (41.5 g, 300 mmol) followed by chloroacetonitrile (17.0 mL, 270 mmol). After 48 h at room temperature, the reaction mixture was diluted with CH₂Cl₂ (200 mL), filtered through plug of celite and concentrated to give dark red oil (26.67 g, 91. ¹H NMR (500 MHz, CDCl₃) δ: 3.91 (2H, t, J=5.5 Hz), 3.40 (2H, s), 2.94 (2H, t, J=5.5 Hz), 2.00 (1H, br s).

Intermediate 50

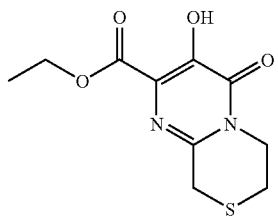

Ethyl 3-hydroxy-4-oxo-4,6,7,9-tetrahydropyrimido[2,1-c][1,4]thiazine-2-carboxylate. A mixture of 2-(2-hydroxyethylthio)acetonitrile (14.79 g, 126 mmol) and 50% aqueous hydroxylamine (7.65 mL, 125 mmol) in ethanol (100 mL) was heated at 80° C. for 2 h. Then, cooled in ice water bath and diethyl acetylenedicarboxylate (20 mL, 125 mmol) was added over 10 minutes. After 2 h at room temperature, the reaction mixture concentrated and the resulting dark residue was taken up in EtOAc (200 mL), washed successively with water (50 mL) and brine (50 mL), and dried ($Na_2SO_4$), filtered and concentrated to afford yellow oil which was used in the next step.

A solution of the above yellow oil in xylenes (200 mL) was heated at reflux for 15 h. The reaction mixture was cooled and extracted with 0.5 M aq. $Na_2CO_3$ (3×40 mL). The combined extracts washed with EtOAc (50 mL), acidified with conc. HCl and extracted with $CH_2Cl_2$ (4×50 mL). The combined $CH_2Cl_2$ extracts dried ($Na_2SO_4$), filtered and concentrated to give dark solid (6.81 g).

To a stirred solution of the above dark solid (6.81 g, ~24.8 mmol) and methanesulfonyl chloride (5.8 mL, 75 mmol) in THF (200 mL) at 0° C. was added $Et_3N$ (11 mL, 78.6 mmol) over 5 minutes. The reaction mixture was stirred for 4 h while allowing it warm to ambient temperature. After 1 h at room temperature, the reaction mixture was diluted with EtOAc (200 mL), washed with water (2×50 mL) and brine (50 mL). The organic layer dried ($Na_2SO_4$), filtered and concentrated to afford dark paste.

The above dark past (7.6 g) was dissolved in 2:1 THF/EtOH (150 mL) and treated with $K_2CO_3$ (2.07 g, 15 mmol). After stirring for 48 h at room temperature, the reaction mixture was concentrated, and the residue was taken up in water (100 mL), neutralized with conc. HCl and extracted with $CH_2Cl_2$ (5×50 mL). The combined $CH_2Cl_2$ dried ($Na_2SO_4$), filtered and concentrated to give dark brown past which was stirred with EtONa (15 mmol) in EtOH for 5 h at room temperature. The reaction mixture was concentrated and the resulting residue taken up in water (100 mL), and extracted with EtOAc (3×50 mL). The organic extracts discarded and aq. layer acidified with conc. HCl and extracted with $CH_2Cl_2$ (5×50 mL). The combined $CH_2CL_2$ extracts dried ($Na_2SO_4$), filtered and concentrated to give dark paste (1.3866 g, 4.3%, 80% pure). LRMS (M+H) calcd for 257.06; found: 257.12.

cooled in ice water bath and diethyl acetylenedicarboxylate (20 mL, 125 mmol) was added over 10 minutes. After 2 h at room temperature, the reaction mixture concentrated and the resulting turbid residue was taken up in EtOAc (200 mL), washed successively with water (2×75 mL) and brine (50 mL), and dried ($Na_2SO_4$), filtered and concentrated to afford a yellow oil.

A solution of above yellow oil in xylenes (1.0 L) was heated at reflux for 6 h. Then, the reaction dark mixture was cooled and concentrated to give dark solid. This solid was dissolved into 0.33 N aq. NaOH (450 mL), filtered and freeze dried to give black powder.

To a stirred slurry of the above black powder in DMF (250 mL) was added methanesulfonylchloride (15.4 mL, 200 mmol), cooled in ice-water bath and treated with Et3N (28 mL, 200 mmol). After 4 h at room temperature, DMF was removed under vaccuo and the resulting residue was triutated with THF (250 mL), filtered and concentrated to afford black paste.

A mixture of above the black paste and $K_2CO_3$ (13.8 g, 100 mmol) in DMF/EtOH (1:1, 200 mL) was stirred at 70° C. for 4 h. To this was carefully added benzyl bromide (8.92 mL, 75 mmol) and $K_2CO_3$ (7 g, 50 mmol) and stirred additional 16 h at 70° C. Then, the reaction mixture was concentrated and the resulting residue was taken up in EtOAc (250 mL), washed with water (3×50 mL), brine (50 mL), dried ($Na_2SO_4$), filtered and concentrated to give dark paste. Flash chromatography on silica gel column using mixtures of 30-60% EtOAc/Hex provided title compound as an orange paste. Crystallization from $Et_2O$/Hex gave product as a white solid (2.88 g, 5.86%). $^1$H NMR (500 MHz, $CDCl_3$) δ: 7.48-7.46 (2H, m), 7.37-7.30 (3H, m), 5.27 (2H, s), 4.40 (2H, t, J=5.5 Hz), 4.35 (2H, q, J=7.0 Hz), 3.77 (2H, s), 3.07 (2H, t, J=6.1 Hz), 1.31 (3H, t, J=7.0 Hz). HRMS (M+H) calcd for $C_{17}H_{19}N_2O_4S$: 347.1066; found: 347.1080.

Intermediate 51

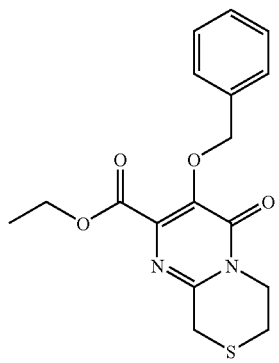

Ethyl 3-(benzyloxy)-4-oxo-4,6,7,9-tetrahydropyrimido[2,1-c][1,4]thiazine-2-carboxylate. A mixture of 2-(2-hydroxyethylthio)acetonitrile (16.6 g, 141.675 mmol) and 50% aqueous hydroxylamine (18.4 mL, 300 mmol) in ethanol (100 mL) was stirred room temperature for 1 h. The reaction mixture was concentrated to remove EtOH and the residue was freeze dried to afford a white powder. This was dissolved in EtOH/$H_2O$ (1:2, 200 mL), Intermediate 52

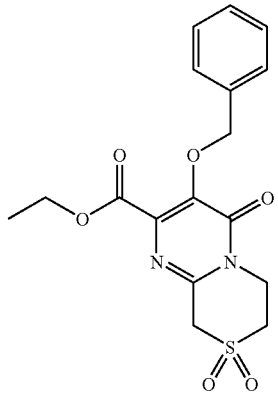

To a stirred solution of ethyl 3-(benzyloxy)-4-oxo-4,6,7,9-tetrahydropyrimido[2,1-c][1,4]thiazine-2-carboxylate (2.76 g, 7.98 mmol) in $CH_2Cl_2$ (100 mL) was added mCPBA (57-86%, 4.27 g, 17.55 mmol) over 5 min and stirred at room temperature for 1.5 h. Then, saturated $NaHCO_3$ (20 mL) and aq. 10% $Na_2S_2O_3$ solution (10 mL) were added and stirred for additional 20 min. Then, the reaction mixture was transferred to separatory funnel and the aq. layer separated. The organic layer washed with sat. $NaHCO_3$ (20 mL), brine (20 mL), dried ($Na_2SO_4$), filtered and concentrated to give yellow residue which was triturated with ether/$CH_2Cl_2$ and filtered to provide the product as white solid (2.69 g, 89%). $^1$H NMR (500 MHz, $CDCl_3$) δ: 7.46-7.44 (2H, m), 7.38-7.32 (3H, m), 5.31

(2H, s), 4.72 (2H, t, J=5.9 Hz), 4.47 (2H, s), 4.34 (2H, q, J=7.0 Hz), 3.49 (2H, t, J=6.1 Hz), 1.31 (3H, t, J=7.0 Hz). HRMS (M+H) calcd for $C_{17}H_{19}N_2O_6S$: 379.0964; found: 379.0974.

Intermediate 53

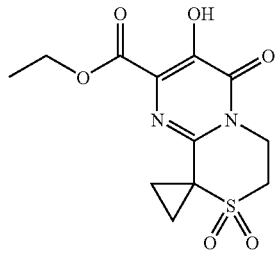

A mixture of intermediate 52 (0.379 g, 1 mmol), 1-chloro-2-iodoethane (0.19 g, 1 mmol) and $Cs_2CO_3$ (0.650 g, 2 mmol) in DMF (10 mL) was stirred at room temperature for 24 h. Then, the reaction mixture was diluted with ether (50 mL), washed with water (3×10 mL), brine (10 mL), dried ($Na_2SO_4$), filtered and concentrated to give a white solid. A solution of the white solid in TFA (5 mL) was stirred at room temperature for 2 h and concentrated. The resulting residue was purified by preparative-HPLC to afford the product as an off-white solid (0.184 g, 59%). $^1$H NMR (500 MHz, CDCl$_3$) δ: 10.82 (1H, s), 4.75 (2H, t, J=6.1 Hz). HRMS (M+H) calcd for $C_{12}H_{16}N_2O_6S$; found: 315.0652.

Intermediate 54

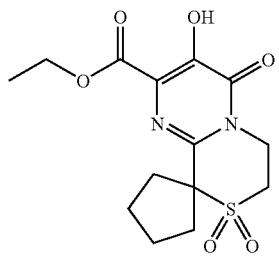

A mixture of intermediate 52 (0.379 g, 1 mmol), 1,4-diiodobutane (0.310 g, 1 mmol) and $Cs_2CO_3$ (0.650 g, 2 mmol) in DMF (6 mL) was stirred at room temperature for 18 h. Then, the reaction mixture was diluted with ether (100 mL), washed with water (3×10 mL), brine (10 mL), dried ($Na_2SO_4$), filtered and concentrated to give viscous brown oil.

A solution of the above brown oil in TFA (10 mL) was stirred at room temperature for 2 h and concentrated. The resulting residue was purified by Prep-HPLC to afford the product as an off-white solid (0.244 g, 71%). $^1$H NMR (500 MHz, CDCl$_3$) δ: 10.82 (1H, s), 4.71 (2H, t, J=6.4 Hz), 4.45 (2H, q, J=7.0 Hz), 3.53 (2H, t, J=6.4 Hz), 2.62-2.48 (4H, m), 1.96-1.90 (4H, m), 1.42 (3H, t, J=7.0 Hz). HRMS (M+H) calcd for $C_{14}H_{19}N_2O_6S$: 343.0964; found: 343.0958.

Intermediate 55

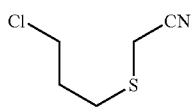

2-(3-Chloropropylthio)acetonitrile: To a stirred solution of 3-chloro-1-propanethiol (20 g, 180.8 mmol) and chloroacetonitrile (12.6 mL, 200 mmol) in THF (150 mL) was added $K_2CO_3$ (27.6 g, 200 mmol). After 24 h at room temperature, the reaction mixture was filtered through a silica gel plug and the plug was washed with ether (100 mL). The filtrate was concentrated to give colorless liquid (9.91 g, 37%). $^1$H NMR (500 MHz, CDCl$_3$) δ: 3.67 (2H, t, J=6.1 Hz), 3.31 (2H, s), 2.92 (2H, t, J=7.0 Hz), 2.15-2.10 (2H, m).

Intermediate 56

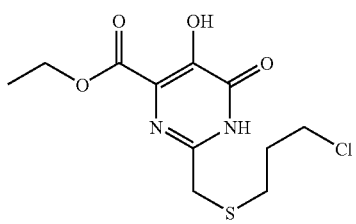

Ethyl 2-((3-chloropropylthio)methyl)-5-hydroxy-6-oxo-1,6-dihydropyrimidine-4-carboxylate: To a stirred solution of 2-(3-chloropropylthio)acetonitrile (9.9 g, 66.15 mmol) in ethanol (50 mL) was added 50% aq. hydroxylamine (4.3 mL, 70 mmol). After 15 h, the reaction mixture was cooled in ice-water bath and diethyl acetylenedicarboxylate was slowly added via syringe. The cold bath was removed and stirred for 1 h at room temperature and concentrated to give yellow residue. This was taken up in ether (200 mL), washed with water (50 mL), brine (50 mL), dried ($Na_2SO_4$), filtered and concentrated to give a yellow oil (25.9 g).

A xylenes (300 mL) solution of the above yellow oil was heated at reflux for 15 and then, cooled and extracted with 0.5 M aq. $Na_2CO_3$ (4×50 mL). The combine aq. layers washed were extracted with EtOAc (2×50 mL) and organic layers discarded. The aq. layer was acidified with conc. HCl and extracted with $CH_2Cl_2$ (4×50 mL). The combined $CH_2Cl_2$ extracts dried ($Na_2SO_4$), filtered and concentrated to afford brown powder (5.0 g, 25%). $^1$H NMR (500 MHz, CDCl$_3$) δ: 11.40 (1H, br s), 10.94 (1H, s), 4.51 (2H, q, J=7.0 Hz), 3.70 (2H, s), 3.61 (2H, t, J=6.1 Hz), 2.70 (2H, t, J=7.0 Hz0, 2.07-2.02 (2H, m), 1.44 (3H, t, J=7.0 Hz). LCMS (M+H) calcd for $C_{11}H_{16}ClN_2O_4S$: 307.05; found: 307.09.

Intermediate 57

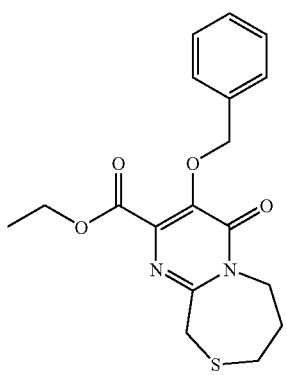

Ethyl 3-(benzyloxy)-4-oxo-6,7,8,10-tetrahydro-4H-pyrimido[2,1-c][1,4]thiazepine-2-carboxylate: A mixture of ethyl 2-((3-chloropropylthio)methyl)-5-hydroxy-6-oxo-1,6-dihydropyrimidine-4-carboxylate (5 g, 16 mmol) and $K_2CO_3$ (4.5 g, 32.5 mmol) in DMF (150 mL) was placed in preheated oil bath and stirred for 1.5 h. After this, benzylbromide (2.4 mL, 20 mmol) was added and continued stirring for additional 3 h. Then, the reaction mixture was cooled, diluted with ether (250 mL0, washed with water (3×50 mL). The combine aq. layers extracted with ether (4×100 mL) and combined with previous organic phase, and washed with brine (50 mL). The organic layer was dried (Na$_2$SO$_4$/activated carbon), filtered and concentrated to give viscous paste. Crystalization of this paste from CH$_2$Cl$_2$/hexanes provided the product as a white solid (4.4 g, 75%). $^1$H NMR (500 MHz, CDCl$_3$) δ: 7.48-7.46 (2H, m), 7.37-7.30 (3H, m), 5.25 (2H, s), 4.36-4.31 (4H, m), 3.89 (2H, s), 2.94 (2H, t, J=5.6 Hz), 2.16-2.12 (2H, m), 1.30 (3H, t, J=7.0 Hz). HRMS (M+H) calcd for C$_{18}$H$_{21}$N$_2$O$_4$S: 361.1222; found: 361.1221.

Intermediate 58

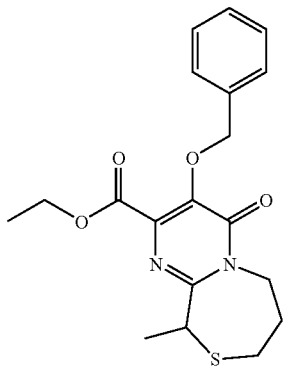

Ethyl 3-(benzyloxy)-10-methyl-4-oxo-6,7,8,10-tetrahydro-4H-pyrimido[2,1-c][1,4]thiazepine-2-carboxylate: To a stirred solution of ethyl 3-(benzyloxy)-4-oxo-6,7,8,10-tetrahydro-4H-pyrimido[2,1-c][1,4]thiazepine-2-carboxylate (0.180 g, 0.5 mmol) and iodomethane (0.62 mL, 10 mmol) in THF (5 mL) at −78 C was added 1M solution of LiHMDS (1 mL, 1 mmol) over 2 minutes. After 1.5 h, the reaction mixture was quenched with saturated aq. NH$_4$Cl, diluted with EtOAc (50 mL), dried (Na$_2$SO$_4$), filtered, concentrated and the residue was purified by Prep-HPLC to afford the desired product as orange solid (0.021 g, 11%). $^1$H NMR (500 MHz, CDCl$_3$) δ: 7.48-7.46 (2H, m), 7.37-7.29 (3H, m), 5.24 (2H, s), 5.15 (1H, dd, J=13.9, 4.4 Hz), 4.33 (2H, q, J=7.0 Hz), 4.18 (1H, q, J=7.0 Hz), 3.62 (1H, dd, J=13.6, 12.1 Hz), 3.14-3.09 (1H, m), 2.77 (1H, dt, J=14.4, 4.2 Hz), 2.34-2.27 (1H, m), 1.91-1.82 (1H, m), 1.62 (3H, d, J=7.0 Hz), 1.30 (3H, t, J=7.0 Hz). HRMS (M+H) calcd for C$_{19}$H$_{23}$N$_2$O$_4$S: 375.1379; found: 375.1375.

Intermediate 59

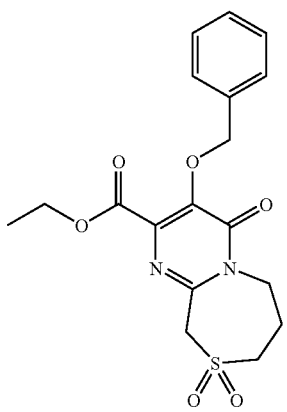

To a stirred solution of ethyl 3-(benzyloxy)-4-oxo-6,7,8,10-tetrahydro-4H-pyrimido[2,1-c][1,4]thiazepine-2-carboxylate (1.894 g, 5.255 mmol) in CH$_2$Cl$_2$ (50 mL) was added mCPBA (57-86%, 3.70 g, 15 mmol) at once. After 1.5 h, saturated NaHCO$_3$ (20 mL) and 10% Na$_2$S$_2$O$_3$ (10 mL) were added and stirred for additional 20 minutes. Then, the organic layer separated, washed successively with sat. NaHCO$_3$ (20 mL), brine (10 mL), dried (Na$_2$SO$_4$), filtered and concentrated to give paste which was crystallized from CH$_2$Cl$_2$/hexanes to afford the product as white solid (2.1 g, 99%). $^1$H NMR (500 MHz, CDCl$_3$) δ: 7.46-7.45 (2H, m), 7.37-7.31 (3H, m), 5.25 (2H, s), 4.60 (2H, s), 4.47-4.41 (2H, m), 4.34 (2H, q, J=7.0 Hz), 3.39 (2H, t, J=6.1 Hz), 2.38-2.33 (2H, m), 1.31 (3H, t, J=7.0 Hz). HRMS (M+H) calcd for C$_{18}$H$_{21}$N$_2$O$_6$S: 393.1120; found: 393.1136.

Intermediate 60

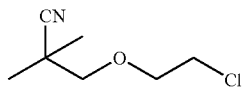

3-(2-Chloroethoxy)-2,2-dimethylpropanenitrile: To a solution of LDA (0.14 mol) in 100 mL THF at −30 C under N$_2$ was added drop-wise isobutyronitrile (9.7 g, 0.14 mol) in 40 mL THF over 20 min. After 20 min, a solution of 1-chloro-2-(chloromethoxy)ethane (18.1 g, 0.14 mol) in 50 mL THF was added drop-wise and the temperature was allowed to gradually rise to room temperature and stirred for 5 h. This was treated with 200 mL of water and Et$_2$O and the layers separated. The aqueous layer was extracted further with Et$_2$O. The combined extracts were washed with brine, dried over Na$_2$SO$_4$, filtered and concentrated to leave 23 g of crude product as a yellow oil. This was purified by silica chromatography using 9:1 hexanes/CH$_2$Cl$_2$ to 4:1 hexanes/CH$_2$Cl$_2$ as eluants. This yielded 7.4 g (32%) of the title compound as an oil. $^1$H NMR (300 MHz, CDCl$_3$) δ: 1.33 (s, 6H), 3.43 (s, 2H), 3.61 (t, J=5.7 Hz, 2H), 3.77 (t, J=5.9 Hz, 2H). LC/MS (M+H): 162.

Intermediate 61

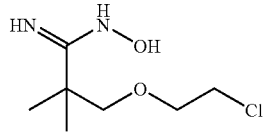

3-(2-Chloroethoxy)-N-Hydroxy-2,2-dimethylpropanamidine: 3-(2-Chloroethoxy)-2,2-dimethylpropanenitrile (6.1 g, 37.7 mmol) was placed together with 50% aqueous hydroxylamine (3.1 g, 37.7 mmol) in 60 mL EtOH and warmed at 75-80 C with stirring for 18 h. The solution was concentrated and then concentrated further with EtOH and vacuum dried to leave (9.4 g, ~80% pure) of the title compound as a gum. $^1$H NMR (300 MHz, CDCl$_3$) δ: 1.17 (s, 6H), 3.40 (s, 2H), 3.58-3.73 (m, 4H), 5.16 (s, 2H). LC/MS (M+H): 195.

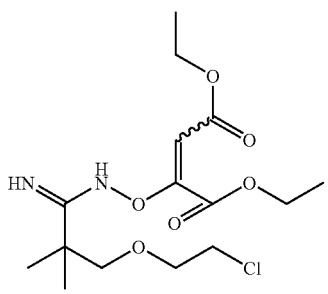

Intermediate 62

Diethyl 2-(3-(2-chloroethoxy)-2,2-dimethylpropanimidamidooxy)but-2-enedioate A solution of 3-(2-chloroethoxy)-N-Hydroxy-2,2-dimethylpropanamidine (7.4 g, 37.7 mmol) in 70 mL EtOH and 10 mL H$_2$O was treated with diethyl acetylenedicarboxylate (6.4 g, 37.7 mmol). This was stirred for 1 h at room temperature and concentrated. The residue was dissolved in EtOAc and washed with water and brine. The EtOAc solution was dried over Na$_2$SO$_4$, filtered and concentrated to leave 14 g of a yellow oil. This was purified by chromatography on silica using 3:1 hexanes/EtOAc to give 5 g (36%) of the title compound as a clear oil. $^1$H NMR (300 MHz, CDCl$_3$) δ: 1.15 (s, 6H), 1.16-1.39 (m, 6H), 3.41 (s, 2H), 3.56-3.77 (m, 4H), 4.05-4.20 (m, 2H), 4.21-4.37 (m, 2H), 5.30-5.45 (m, 1H), 5.62 (s, 0.5H), 5.64-5.75 (m, 1H), 5.77 (s, 0.5H). LC/MS (M+H): 365.

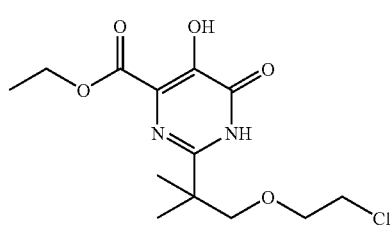

Intermediate 63

Ethyl 2-(1-(2-chloroethoxy)-2-methylpropan-2-yl)-5-hydroxy-6-oxo-1,6-dihydropyrimidine-4-carboxylate Diethyl 2-(3-(2-chloroethoxy)-2,2-dimethylpropanimidamidooxy)but-2-enedioate was dissolved in 150 mL 1,2,4-trimethylbenzene and heated at 155-160° C. for 2.5 hrs with stirring under N$_2$. The solvent was evaporated at reduced pressure and the residue was dissolved in EtOAc and extracted 2× with dil NaHCO$_3$. The aqueous extracts were acidified with HCl and extracted with CH$_2$Cl$_2$. After drying (MgSO$_4$), filtration and concentration provided the title compound (1.9 g, 43%) as a white solid. $^1$H NMR (300 MHz, CDCl$_3$) δ: 1.31 (s, 6H), 1.41 (t, J=7.1 Hz, 3H), 3.54 (s, 2H), 3.63-3.72 (m, 2H), 3.75-3.83 (m, 2H), 4.42 (q, J=7.3 Hz, 2H). LC/MS (M+H): 319.

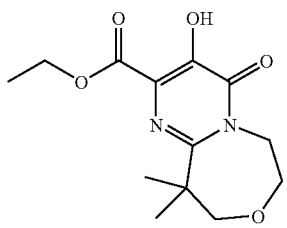

Intermediate 64

Ethyl 3-hydroxy-10,10-dimethyl-4-oxo-6,7,9,10-tetrahydro-4H-pyrimido[1,2-d][1,4]oxazepine-2-carboxylate. Ethyl 2-(1-(2-chloroethoxy)-2-methylpropan-2-yl)-5-hydroxy-6-oxo-1,6-dihydropyrimidine-4-carboxylate (1.75 g, 5.49 mmol) was dissolved in 30 mL DMF under N2 and treated with K$_2$CO$_3$ (2.27 g, 16.5 mmol). This was warmed at 70-80° C. with stirring for 16 h. The DMF was evaporated at reduced pressure and the residue was dissolved in water and washed with Et$_2$O. The aqueous layer was acidified with dil HCl and extracted with CH$_2$Cl$_2$. After drying (MgSO$_4$), filtration and concentration a solid was obtained. Trituration from 1:1 Et$_2$O/hexanes gave the title compound (1.2 g, 77%) as white solid. $^1$H NMR (300 MHz, CDCl$_3$) δ: 1.35-1.45 (m, 9H), 3.58 (s, 2H), 3.60-4.10 (m, 1H), 4.41 (q, J=6.95 Hz, 2H), 4.30-4.82 (m, 2H), 10.42 (s, 1H). LC/MS (M+H): 283.

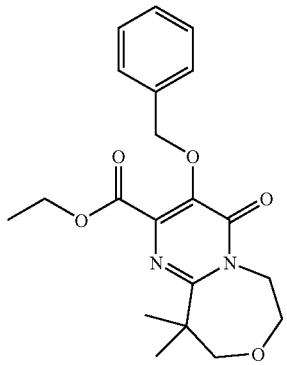

Intermediate 65

Ethyl 3-(benzyloxy)-10,10-dimethyl-4-oxo-6,7,9,10-tetrahydro-4H-pyrimido[1,2-d][1,4]oxazepine-2-carboxylate. Ethyl 3-hydroxy-10,10-dimethyl-4-oxo-6,7,9,10-tetrahydro-4H-pyrimido[1,2-d][1,4]oxazepine-2-carboxylate (790 mg, 2.8 mmol) and benzyl bromide (580 mg, 3.4 mmol) were placed together in 10 mL DMF under N$_2$ and treated with K$_2$CO$_3$ (512 mg, 4 mmol). After warming for 2.5 h at 60-70° C., the DMF was removed under reduced pressure. The residue was dissolved in CH$_2$Cl$_2$ and washed with H$_2$O. The CH$_2$Cl$_2$ solution was dried over MgSO$_4$, filtered and concentrated to give the title compound (940 mg, 90%) as a solid. $^1$H NMR (300 MHz, CDCl$_3$) δ: 1.27 (t, J=7.3 Hz, 3H), 1.54 (s, 6H), 3.59 (s, 2H), 3.65-3.95 (m, 2H), 4.30 (q, J=7.3 Hz, 2H), 4.40-4.80 (m, 2H), 5.19 (s, 2H), 7.29-7.34 (m, 3H), 7.39-7.49 (m, 2H). LC/MS (M+H): 373.

Intermediate 66

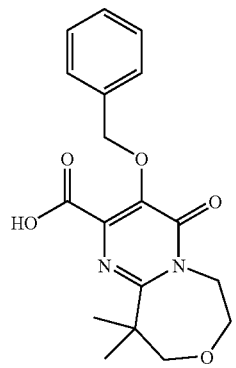

3-(Benzyloxy)-10,10-dimethyl-4-oxo-6,7,9,10-tetrahydro-4H-pyrimido[1,2-d][1,4]oxazepine-2-carboxylic acid. Ethyl 3-(benzyloxy)-10,10-dimethyl-4-oxo-6,7,9,10-tetrahydro-4H-pyrimido[1,2-d][1,4]oxazepine-2-carboxylate (920 mg, 2.5 mmol) was dissolved in 5 mL of THF and to it was added with stirring LiOH (120 mg, 5 mmol) and 5 mL water. After 30 min, the THF was evaporated and the aqueous layer was acidified with dil HCl. This was extracted with $CH_2Cl_2$, dried ($MgSO_4$), filtered and concentrated. Trituration from $Et_2O$ gave the title compound (790 mg, 91%) as a solid: $^1$H NMR (300 MHz, $CDCl_3$) δ: 1.40 (s, 6H), 3.60 (s, 2H), 3.65-3.95 (m, 2H), 4.10-4.90 (m, 2H), 5.41 (s, 2H), 7.25-7.42 (m, 3H), 7.45-7.58 (m, 2H). LC/MS (M+H): 345.

Intermediate 67

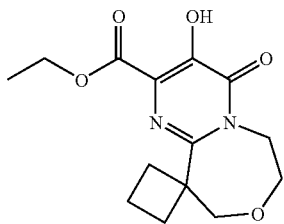

Ethyl 3'-hydroxy-4'-oxo-4',6',7',9'-tetrahydrospiro[cyclobutane-,1,10'-pyrimido[1,2-d][1,4]oxazepine]-2'-carboxylat.e $^1$H NMR (300 MHz, $CDCl_3$) δ: 1.42 (t, J=7.0 Hz, 3H), 1.78-2.27 (m, 4H), 2.57-2.75 (m, 2H), 3.59-3.79 (m, 2H), 3.82 (s, 2H), 4.27-4.36 (m, 2H), 4.43 (q, J=7.0 Hz, 2H), 10.50 (s, 1H). LC/MS (M+H) m/z 295.

Intermediate 68

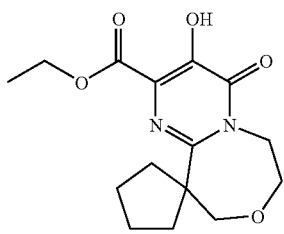

Ethyl 3'-hydroxy-4'-oxo-4',6',7',9'-tetrahydrospiro[cyclopentane-1,10'-pyrimido[1,2-d][1,4]oxazepine]-2'-carboxylate. $^1$H NMR (300 MHz, $CDCl_3$) δ: 1.41 (t, J=7.0 Hz, 3H), 1.59-1.83 (m, 8H), 2.12-2.29 (m, 2H), 3.55 (s, 2H), 3.61-3.69 (m, 2H), 3.72-3.80 (m, 2H), 4.41 (q, J=7.0 Hz, 2H), 10.67 (s, 1H). LC/MS (M+H) m/z 309.

Intermediate 69

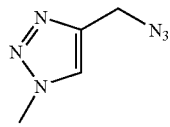

4-(Azidomethyl)-1-methyl-1H-1,2,3-triazole. A solution of (1-methyl-1H-1,2,3-triazol-4-yl)methanol (0.62 g, 5.48 mmol) (F. Sternfeld et al. J. Med. Chem. 47, 2004, 216-2179) in tetrahydrofuran (12 ml) was cooled to 0° C. and treated with methanesulfonyl chloride (0.42 ml, 5.50 mmol). Triethylamine (0.75 ml, 5.5 mmol) was then added dropwise and the mixture was stirred for 15 min. The reaction mixture was then diluted with N,N-dimethylformamide (10 ml), treated with sodium azide (0.80 g, 12.3 mmol) and stirred at 22° C. for 18 h. The mixture was then diluted with ethyl acetate washed with water and brine and dried over anhydrous magnesium sulfate. Evaporation of the solvent and chromatography of the residue on silica gel (elution ethyl acetate) gave 0.710 g (94% yield) of the title material as a clear oil. $^1$HNMR 400 MHz ($CDCl_3$) δ (ppm): 4.15 (3H, s, $CH_3$), 4.51 (2H, s, $NCH_2$), 7.57 (1H, s, CH). MS ($ESI^+$) m/z 139 [$M+H^+$].

Intermediate 70

(1-Methyl-1H-1,2,3-triazol-4-yl)methanamine. Hydrogenation of 4-(azidomethyl)-1-methyl-1H-1,2,3-triazole (0.70 g, 5.07 mmol) gave 0.55 g (98% yield) of the title amine as an oil. $^1$HNMR 400 MHz ($CDCl_3$) δ (ppm): 3.94 (2H, m, $NCH_2$), 4.10 (3H, s, $CH_3$), 7.52 (1H, m, CH).

Intermediate 71

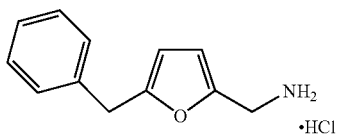

2-(Azidomethyl)-5-benzylfuran. $^1$HNMR 400 MHz ($CDCl_3$) δ (ppm): 3.99 (2H, s, $CH_2$), 4.27 (2H, s, $CH_2$), 5.98 (1H, d, J=3.1 Hz, CH), 6.27 (1H, d, J=3.1 Hz, CH), 7.25-7.35 (5H, m, aromatics). MS ($ESI^+$) m/z 213 [$M+H^+$].

Intermediate 72

(5-Benzylfuran-2-yl)methanamine hydrochloride salt. $^1$HNMR 400 MHz (DMSO-$d_6$) δ (ppm): 3.98 (2H, s, $CH_2$), 4.02 (2H, s, CH$_2$), 6.17 (1H, d, J=3 Hz, CH), 6.45 (1H, d, J=3 Hz, CH), 7.22-7.35 (5H, m, aromatics). MS (ESI$^+$) m/z 188 [M+H$^+$].

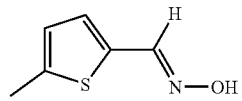

Intermediate 73

5-Methylthiophene-2-carbaldehyde oxime: To a solution of 5-methylthiophene-2-carboxaldehyde (4.0 g, 31.8 mmol; Aldrich) in EtOH (24 mL) was added a solution of hydroxylamine hydrochloride (3.28 g, 47.2 mmol; Aldrich) in water (6 mL) and then a solution of sodium acetate (5.20 g, 67.5 mmol) in water (6 mL after which the mixture heated at reflux for 1 h. The mixture, after cooling, was concentrated in vacuo, and the residue diluted with water and extracted with CH$_2$Cl$_2$ (25 mL×2). The combined extracts were washed with water, brine, dried (Na$_2$SO$_4$), filtered and concentrated. The residual oily solid was triturated with Et$_2$O (~20 mL) to obtain 3.4 g (76% yield) of the title compound as an off-white powder: HPLC: 1.69 min (at 254 nm); LC/MS m/z 142 (M+H); $^1$H NMR (500 MHz, CDCl$_3$) δ ppm 2.53 (3H, s, CH$_3$), 6.77 (1H, d, J=3.7 Hz, Th—H), 7.21 (1H, d, J=3.7 Hz, Th—H), 7.63 (1H, s, Th—H), 9.22 (1H, br, OH); $^1$H NMR (500 MHz, DMSO-d6) δ ppm 2.46 (3H, s, CH$_3$), 6.83 (1H, dd, J=3.5, 1 Hz, Th—H), 7.26 (1H, d, J=3.5 Hz, Th—H), 7.71 (1H, s, Th—H), 11.65 (1H, s, 6-NOH); $^{13}$C NMR (125.8 MHz, CDCl$_3$) δ ppm 15.4 (CH$_3$), 125.0 (CH), 129.1 (C), 132.5 (CH), 141.4 (CH), 147.0 (C); HRMS (ESI) calcd for C$_6$H$_8$NOS (M+H) 142.0327, found 142.0327 (δ+0.3 ppm). $^1$H— and $^{13}$C-NMR indicated this material was predominantly one geometric isomer. The mother liquor, after concentration gave 0.79 g (18% yield) of the title compound, whose $^1$H-NMR indicated a ~1:1 mixture of two geometric oxime isomers.

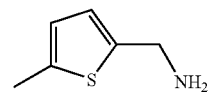

Intermediate 74

(5-Methylthiophen-2-yl)methanamine: To a stirred 1M solution of lithium aluminum hydride in THF (50 mL, 50 mmol; Aldrich) was added drop-wise over 10 min a solution of the 5-methylthiophene-2-carbaldehyde oxime (3.38 g, 24 mmol) in THF (5 mL; Sure Seal, Aldrich) at room temperature and then the mixture was heated at reflux for 1.5 h under a nitrogen atmosphere. To the mixture, after cooling, was added drop-wise and carefully with vigorous stirring water (2 mL), 15% NaOH (2 mL) and then water (6 mL). To this was added Na$_2$SO$_4$ (20 g) and stirred under nitrogen overnight. This was filtered through Celite and washed with CH$_2$Cl$_2$. The filtrate and washings were combined, concentrated in vacuo to obtain 2.82 g (92% yield) of the title compound as an amber colored oil: HPLC: 0.60 min (at 254 nm); $^1$H NMR (500 MHz, CDCl$_3$) δ ppm 1.54-1.79 (2H, br, NH$_2$), 2.44 (3H, s, CH$_3$), 3.94 (2H, s, CH$_2$), 6.56 (1H, d, J=3.4 Hz, Th—H), 6.66 (1H, d, J=2.7 Hz, Th—H); $^{13}$C NMR (125.8 MHz, CDCl$_3$) δ ppm 15.5 (CH$_3$), 41.7 (CH$_2$), 123.6 (CH), 124.8 (CH), 138.6 (C), 145.2 (C).

This free base (2.18 g, 17.2 mmol) was dissolved in anhydrous diethyl ether (50 mL), and to this was added 2M HCl in diethyl ether (20 mL). The precipitate formed was filtered, washed with ether, and dried in vacuo to obtain 1.88 g (67% yield) of the title compound as a brownish powder: HPLC: 0.50 min (at 254 nm); $^1$H NMR (500 MHz, DMSO-d$_6$) δ ppm 2.43 (3H, s, CH$_3$), 4.12 (2H, q, J=5.4 Hz, CH$_2$), 6.74 (1H, d, J=3.4 Hz, Th—H), 7.03 (1H, d, J=3.4 Hz, Th—H), 8.46 (3H, brs, $^+$NH$_3$).

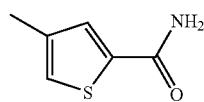

Intermediate 75

4-Methyl-thiophene-2-carboxylic acid amide. To a stirred solution of 4-methlthiophene-2-carboxylic acid (8) (5.12 g, 35 mmol; Aldrich) and DMF (3 drops, ~0.15 mL) in CH$_2$Cl$_2$ (40 mL) cooled in an ice-bath was added under nitrogen drop-wise over a period of 10 min a 2M solution of oxalyl chloride in CH$_2$Cl$_2$ (20 mL, 40 mmol: Aldrich). The mixture was stirred at room temperature for 1 h. The mixture was concentrated in vacuo: $^1$H NMR (500 MHz, CDCl$_3$) δ ppm 2.31 (3H, s) 7.42 (1H, s) 7.77 (1H, s); $^{13}$C NMR (125.8 MHz, CDCl$_3$) δ ppm 15.7 (CH$_3$), 133.9 (CH), 136.9 (C), 139.7 (CH), 159.8 (C).

The residue, re-dissolved in EtOAc (20 mL) was added to a stirred solution of conc-NH$_4$OH (28%, 30 mL) in EtOAc (100 mL) in an ice-bath, and the mixture stirred at room temperature for 2 h. The cloudy solution was filtered through Celite and the clear filtrate was washed with brine, dried (Na$_2$SO$_4$), filtered and concentrated in vacuo to obtain 4.80 g (34.0 mmol, Y.97%) of the title compound as a beige solid: HPLC: 1.10 min (AP 99% at 254 nm); LC/MS m/z 142 (M+H); $^1$H NMR (500 MHz, CDCl$_3$) δ ppm 2.26 (3H, s, 7-Me), 6.04 (2H, brs, NH$_2$), 7.09 (1H, d, J=1.5 Hz, 5-H), 7.34 (1H, d, J=1 Hz, 3-H); $^{13}$C NMR (125.8 MHz, CDCl$_3$) δ ppm 15.7 (7-CH$_3$), 126.6 (5-CH), 131.6 (3-H), 137.4 (2-C), 138.6 (4-C), 164.2 (6-C=O); HRMS (ESI) calcd for C$_6$H$_8$NOS (M+H) 142.0327, found 142.0321.

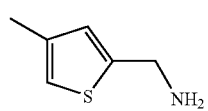

Intermediate 76

(4-Methylthiophen-2-yl)methanamine. The title compound (2.40 g) was prepared as an amber colored oil in 99% yield from 4-methyl-thiophene-2-carboxylic acid amide (2.70 g, 19.0 mmol) and LiAlH$_4$ (1M THF solution, 40 mL). LRMS (ESI) m/z 128 (M+H). $^1$H NMR (500 MHz, CDCl$_3$) δ ppm 2.21 (3H, s, CH$_3$), 3.97 (2H, s, CH$_2$), 6.71 (1H, s, Th—H), 6.74 (1H, s, Th—H). $^{13}$C NMR (125.8 MHz, CDCl$_3$) δ ppm 15.8 (CH$_3$), 41.6 (CH$_2$), 119.1 (CH), 126.1 (CH), 137.5 (CH), 147.5 (C).

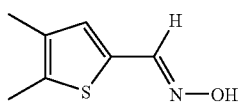

Intermediate 77

4,5-Dimethylthiophene-2-carbaldehyde oxime (about 2:1 mixture of oxime region-isomers). Yield: 98% (white powder). HPLC: 2.22 min (AP 74% at 254 nm) and 2.33 min (AP 26% at 254 nm). LC/MS: m/z 156 (M+H). $^1$H NMR (500 MHz, CDCl$_3$) δ ppm 2.10 (3×1/3H, s, CH$_3$), 2.14 (3×2/3H, s, CH$_3$), 2.33 (3×1/3H, s, CH$_3$), 2.37 (3×2/3H, s, CH$_3$), 6.89 (1×2/3H, s, Th—H), 7.10 (1×2/3H, s, Th—H), 7.56 (1×2/3H, s, Th—H), 8.14 (1×1/3H, s, Th—H). $^{13}$C NMR (125.8 MHz, CDCl$_3$) δ ppm 13.3, 13.4, 13.5 (CH$_3$), 126.4 (minor, C), 130.5 (minor, C), 133.0 (minor, CH), 133.0 (major, C), 133.7 (major, C), 135.2 (major, CH), 136.1 (minor, C), 140.9 (major, C), 141.2 (major, CH), 145.2 (minor, CH).HRMS (ESI) calcd for C$_7$H$_{10}$NOS (M+H) 156.0483, found 156.0480.

Intermediate 78

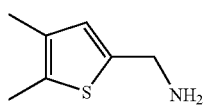

(4,5-Dimethylthiophen-2-yl)methanamine. Yield: 99% (amber colored oil). HPLC: 1.43 min (AP 95% at 254 nm). LRMS (ESI) 142 (M+H), 158 (M+17). $^1$H NMR (500 MHz, CDCl$_3$) δ ppm 2.07 (3H, s, CH$_3$), 2.29 (3H, s, CH$_3$), 3.90 (2H, s, Th—CH$_2$), 6.58 (1H, s, Th—H). $^{13}$C NMR (125.8 MHz, CDCl$_3$) δ ppm 13.1 (CH$_3$), 13.6 (CH$_3$), 41.5 (CH$_2$), 126.8 (CH), 131.4 (C), 132.7 (C), 142.4 C).

Intermediate 79

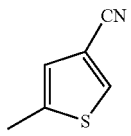

5-Methylthiophene-3-carbonitrile. To a solution of 2-methyl-4-bromothiophene (16) (1.00 g, 5.65 mmol; Oakwood) in N-methyl-2-pyrrolidone (5 mL) was added CuCN (1.08 g, 12.1 mmol) and the mixture stirred in an oil bath heated at 160° C. under a nitrogen atmosphere for 20 h. This mixture was cooled and to this was added 14% aq. NH$_4$OH (10 mL) and stirred for 15 min. To this diethyl ether (15 mL) was added and stirred for 30 min. The ether layer was collected and the aqueous layer was extracted again with diethyl ether (15 mL). The combined ether extracts were washed with dilute ammonium hydroxide solution, brine, dried (Na$_2$SO$_4$), filtered and concentrated to obtain 585 mg (4.76 mmol, Y. 84%) of the title compound as a volatile organic oil: HPLC: 2.04 min (AP 82% at 254 nm). LC/MS m/z 156 (M+H+MeOH); $^1$H NMR (500 MHz, CDCl$_3$) δ ppm 2.49 (3H, s, CH$_3$), 6.93 (1H, s, Th—H), 7.68 (1H, s, Th—H); $^{13}$C NMR (125.8 MHz, CDCl$_3$) δ ppm 15.1 (CH$_3$), 110.3 (C), 115.5 (CN), 126.3 (CH), 133.7 (CH), 142.1 (C).

Intermediate 80

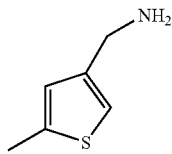

(5-Methylthiophen-3-yl)methanamine. To a stirred solution of lithium aluminum hydride in THF (1M, 4.5 mL, 4.5 mmol; Aldrich) was added drop-wise over 10 min a solution of 5-methylthiophene-3-carbonitrile (550 mg, 4.47 mmol) in THF (5 mL; Sure Seal, Aldrich) at room temperature and then the mixture was heated at reflux for 1 h under a nitrogen atmosphere. To the mixture, after cooling was added dropwise and carefully with vigorous stirring sequentially water (1 mL), 15% NaOH (1 mL) and then water (3 mL). To this was added Na2SO4 (10 g) and stirred under nitrogen for 1 h. This was filtered through Celite and washed with CH2Cl2. The filtrate and washings were combined, concentrated in vacuo to obtain 450 mg (79% yield) of the title compound as an amber colored oil: HPLC: 0.61 min (at 254 nm); LRMS (APCI) m/z 128 (M+H); $^1$H NMR (500 MHz, CDCl3) δ ppm 1.56 (2H, s, NH2), 2.45 (3H, s, CH3), 3.77 (2H, s, CH2), 6.68 (1H, s, Th—H), 6.82 (1H, s, Th—H); 13C NMR (125.8 MHz, CDCl3) δ ppm 15.4 (CH3), 42.0 (CH2), 118.0 (CH), 125.3 (CH), 140.5 (C), 144.6 (C).

Intermediate 81

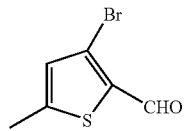

3-Bromo-5-methylthiophene-2-carbaldehyde. The title compounds was prepared by the method described by Frohlich et al., (Monatshefte fur Chemie 1996, 127, 325). To a stirred solution of diisopropylamine (3.85 g, 38 mmol) in THF (25 mL, Sure Seal, Aldrich) was added drop-wise through a syringe at −30° C. a solution of n-BuLi in hexane (1.6M, 21.3 mL, 34 mmol, Aldrich) under a nitrogen atmosphere, and the mixture stirred at −30° C. for another 20 min. This LDA solution was cooled to −70° C. and to this solution was added a solution of 5-methyl-2-bromothiophene (5.00 g, 3.23 mL, 28 mmol, Aldrich) quickly and stirred at −70° C. for 2 h. To this mixture was then added a solution of DMF (2.56 g, 35 mmol) in THF (10 mL) at −70° C. over a period of 30 min. This mixture was stirred at −70° C. for another 30 min, and the cooling bath was removed. After 1 h, the mixture was poured into water (50 mL), and extracted with diethyl ether (25 mL×2). The combined extracts were washed with brine, dried (Na$_2$SO$_4$), filtered and concentrated to obtain 5.23 g of a brown oily solid which was triturated with a 2:1 mixture of diethyl ether and hexanes to collect 2.45 g (43% yield) of the title compound as a brownish crystalline powder: HPLC: 2.29 min (at 254 nm), impurity peak at 2.82 min (AP 14.8% for 2-Br-5-Me-thiophene, the starting bromide); LC/MS m/z 205/207 (M+H); $^1$H NMR (500 MHz, CDCl$_3$) δ ppm 2.54 (3H, s, Me), 6.84 (1H, s, Th—H), 9.86 (1H, s, CHO); $^{13}$C NMR (125.8 MHz, CDCl$_3$) δppm 16.5 (CH$_3$), 120.5 (C), 130.6 (CH), 135.0 (C), 151.1 (C), 182.7 (C=O). An additional amount (1.48 g, 7.22 mmol; total yield 69%) of the title compound was obtained from the mother liquor by column chromatography (SiO$_2$, 20-50% CH$_2$Cl$_2$/hexanes).

Intermediate 82

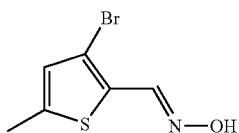

3-Bromo-5-methylthiophene-2-carbaldehyde oxime. Yield: 92%; beige crystalline solid. HPLC: 2.19 min (AP 72% at 254 nm), 2.30 (AP 28%, minor geometric isomer). LC/MS: m/z 220/222 (M+H). $^1$H NMR (500 MHz, CDCl$_3$) δ ppm 2.46 (1.5H, d, J=0.9 Hz, Me), 2.50 (3H, d, J=0.9 Hz, Me), 6.68 (0.5H, q, J=0.9 Hz, Th—H), 6.78 (1H, q, J=0.9 Hz, Th—H), 7.82 (1H, s, oxime-H), 8.27 (0.5H, s, oxime-H). $^{13}$C NMR (125.8 MHz, CDCl$_3$) δ ppm 15.5 (CH$_3$), 15.8 (CH$_3$), 113.4 (CBr), 115.3 (C), 123.5 (C), 127.9 (C), 128.1 (CH), 128.8 (CH), 140.1 (CH), 142.6 (C), 144.5 (CH), 146.4 (C); HRMS (ESI) calcd for C$_6$H$_7$BrNOS (M+H) 219.9432, found 219.9433.

Intermediate 83

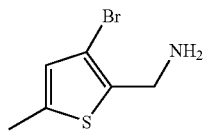

(3-Bromo-5-methylthiophen-2-yl)methanamine. To a stirred solution of lithium aluminum hydride in Et$_2$O (1M, 4.1 mL, 4.1 mmol; Aldrich) and diethyl ether (15 mL, Sure Seal, Aldrich) was added drop-wise over 10 min a solution of the 3-bromo-5-methylthiophene-2-carbaldehyde oxime (450 mg, 2.05 mmol) in Et$_2$O (20 mL; Sure Seal, Aldrich) at room temperature and then the mixture stirred at room temperature for 4 h under a nitrogen atmosphere. To the mixture was added drop-wise and carefully with vigorous stirring water (1 mL), 15% NaOH (1 mL) and then water (3 mL). After stirring for 1 h, to this was added Na$_2$SO$_4$ (10 g) and stirred for another 1 h. This was filtered through Celite and washed with CH$_2$Cl$_2$. The filtrate and washings were combined, concentrated in vacuo to obtain 275 mg (1.33 mmol, Y. 65%) of the title compound contaminated about 30% of (5-methylthiophen-2-yl)methanamine as a brownish oil: HPLC: 1.04 min (AP 60% at 254 nm); impurity peaks at 0.55 min (AP 20% for des-Br-amine), 1.63 min (AP 11%, unknown); LC/MS m/z 189/191 (M+H—NH$_3$); $^1$H NMR (500 MHz, CDCl$_3$) δ ppm 2.43 (3H, s, CH$_3$), 3.90 (2H, s, CH$_2$), 6.59 (1H, s, Th—H).

Intermediate 84

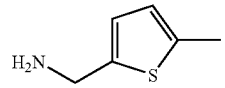

(5-Methylthiophen-2-yl)methanamine. Prepared in the reaction above.

Intermediate 85

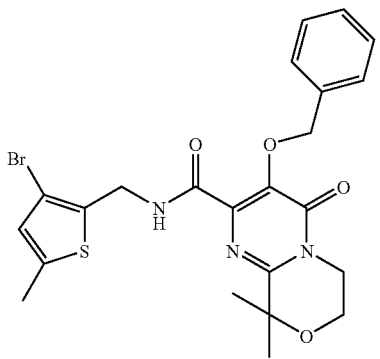

3-(Benzyloxy)-N-((3-bromo-5-methylthiophen-2-yl)methyl)-9,9-dimethyl-4-oxo-4,6,7,9-tetrahydropyrimido[2,1-c][1,4]oxazine-2-carboxamide. To a solution of 3-(benzyloxy)-9,9-dimethyl-4-oxo-4,6,7,9-tetrahydropyrimido[2,1-c][1,4]oxazine-2-carboxylic acid (376 mg, 1.14 mmol) in dimethylformamide (8 mL) was added O-(7-azabenzotriazol-1-yl)-N,N,N',N'-tetramethyluronium hexafluorophosphate (HATU, 0.167 g, 0.44 mmol; Aldrich) and the mixture was stirred under nitrogen for 20 minutes. To this was added (3-bromo-5-methylthiophen-2-yl)methanamine and N,N-dimethylaminopyridine (146 mg, 1.20 mmol; Aldrich) and the mixture stirred for 1.5 h. The solvent was removed in-vacuo and the crude product in ethyl acetate (25 mL) was washed with 1 N hydrochloric acid (15 mL), then with brine, dried (sodium sulfate), filtered, and concentrated to give 800 mg of an orange-brown solid. This was purified by silica gel column chromatography, eluting with 15% ethyl acetate in CH$_2$Cl$_2$ to give 302 mg (0.585 mmol, Y. 51%) of 3-(benzyloxy)-N-((3-bromo-5-methylthiophen-2-yl)methyl)-9,9-dimethyl-4-oxo-4,6,7,9-tetrahydropyrimido[2,1-c][1,4]oxazine-2-carboxamide as a beige crystalline powder: HPLC: 3.02 min (AP 98% at 254 nm). LC/MS m/z 518/520(M+H); $^1$H NMR (500 MHz, CDCl$_3$) δ ppm 1.60 (6H, s, gem-CH$_3$), 2.40 (3H, s, Th—CH$_3$), 3.93-3.98 (2H, m, NCH$_2$), 3.98-4.03 (2H, m, OCH$_2$), 4.59 (2H, d, J=6.1 Hz, NCH$_2$), 5.27 (2H, s, OCH$_2$), 6.59 (1H, s, Th—H), 7.26-7.35 (3H, m, Ph-H) 7.49 (2H, d, J=6.7 Hz, Ph-H), 7.81 (1H, t, J=5.6 Hz, NH); $^{13}$C NMR (125.8 MHz, CDCl$_3$) δ ppm 15.5 (CH$_3$), 27.8 (10,11-CH$_3$), 37.4 (13-CH$_2$), 43.0 (7-NCH$_2$), 58.1 (8-OCH$_2$), 74.8 (19-OCH$_2$), 76.2 (9-C), 109.0 (C—Br), 127.9 (CH), 128.4 (CH), 128.5 (CH), 128.9 (CH), 132.3 (C), 136.5 (C), 139.8 (C), 140.3 (C), 142.1 (C), 156.3 (C), 159.7 (C=O), 162.3 (C=O); HRMS (ESI) calcd for C$_{23}$H$_{25}$BrN$_3$O$_4$S (M+H) 518.0749, found 518.0739.

Intermediate 86

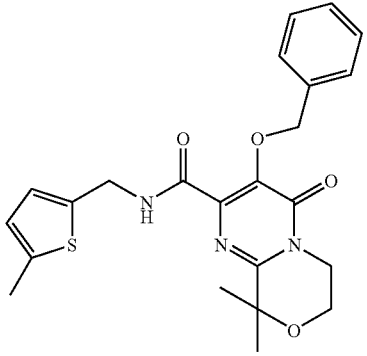

3-(Benzyloxy)-N-((5-methylthiophen-2-yl)methyl)-9,9-dimethyl-4-oxo-4,6,7,9-tetrahydropyrimido[2,1-c][1,4]oxazine-2-carboxamide. HPLC: 2.68 min (AP 85% at 254 nm); LC/MS m/z 440 (M+H); $^1$H NMR (500 MHz, CDCl$_3$) δ ppm 1.61 (6H, s, gem-CH$_3$), 2.44 (3H, s, Th—CH$_3$), 3.95-4.01 (2H, m, NCH$_2$), 4.01-4.06 (2H, m, OCH$_2$), 4.63 (2H, d, J=5.5 Hz, NCH$_2$), 5.28 (2H, s, OCH$_2$), 6.55-6.61 (1H, m, Th—H), 6.74 (1H, d, J=3.1 Hz, Th—H), 7.27-7.38 (3H, m, Ph-H) 7.50 (2H, d, J=7.6 Hz, Ph-H), 7.62 (1H, brs, NH); $^{13}$C NMR (125.8 MHz, CDCl$_3$) δ ppm 15.5 (CH$_3$), 27.8 (CH$_3$), 38.7 (CH$_2$), 43.0 (CH$_2$), 58.1 (CH$_2$), 74.9 (C), 76.2 (C), 125.0 (CH), 126.1 (CH), 128.5 (CH), 128.6 (CH), 129.0 (CH), 136.5 (C), 138.0 (C), 140.0 (C), 142.1 (C), 156.3 (C), 159.7 (C=O), 162.2 (C=O); HRMS (ESI) calcd for C$_{23}$H$_{26}$N$_3$O$_4$S (M+H) 440.1644, found 440.1624.

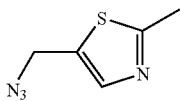

Intermediate 87

5-(Azidomethyl)-2-methylthiazole. A solution of (2-methylthiazol-5-yl)methanol (3.99 g, 30.9 mmol) in tetrahydrofuran (100 ml) was cooled to 0° C. and treated with methanesulfonyl chloride (2.40 ml, 30.9 mmol) followed by triethylamine (4.3 ml, 30.9 mmol) added dropwise over 10 min. The resulting mixture was stirred for 20 min, diluted with N,N-dimethylformamide (50 ml) and then treated with sodium azide (3.20 g, 49.2 mmol). After 18 h at 22° C., the reaction mixture was diluted with ethyl acetate, washed with saturated sodium bicarbonate, brine and dried over anhydrous magnesium sulfate. Evaporation of the solvent under reduced pressure followed by chromatography of the residue on silica gel (elution toluene-ethyl acetate 0-20%) gave 4.42 g (92% yield) of the title azide as a clear oil. 1HNMR 400 MHz (CDCl$_3$) δ (ppm): 2.74 (3H, s, CH$_3$), 4.50 (2H, s, CH$_2$), 7.56 (1H, s, CH). MS (ESI+) m/e 155 [M+H+].

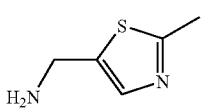

Intermediate 88

(2-Methylthiazol-5-yl)methanamine dihydrochloride salt. A solution of 5-(azidomethyl)-2-methylthiazole (4.40 g, 28.54 mmol) in ethanol (350 ml), water (50 ml) and concentrated hydrochloric acid (10 ml) was hydrogenated over 1 g of 10% Palladium on activated carbon and under one atmosphere of hydrogen for 18 h. The catalyst was then filtered and the filtrate was evaporated under reduced pressure. Triturating the residual solid in anhydrous ethanol gave 4.55 g (79% yield) of the title amine hydrochloride as a white solid. $^1$HNMR 400 MHz (DMSO-d$_6$) δ (ppm): 2.68 (3H, s, CH$_3$), 4.22-4.26 (2H, m, NCH$_2$), 7.77 (1H, s, CH), 8.62 (3H, broad, NH).

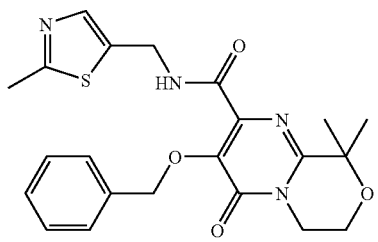

Intermediate 89

3-(Benzyloxy)-9,9-dimethyl-N-((2-methylthiazol-5-yl) methyl)-4-oxo-4,6,7,9-tetrahydropyrimido[2,1-c][1,4]oxazine-2-carboxamide. A mixture of 3-(benzyloxy)-9,9-dimethyl-4-oxo-4,6,7,9-tetrahydropyrimido[2,1-c][1,4]oxazine-2-carboxylic acid (0.200 g, 0.605 mmol) and (2-methylthiazol-5-yl)methanamine dihydrochloride salt (0.135 g, 0.67 mmol) in acetonitrile (15 ml) was treated at 25° C. with triethylamine (0.40 ml, 2.9 mmol) followed by benzotriazole-1-yl-oxy-tris-(dimethylamino)-phosphonium-hexafluorophosphate (0.30 g, 0.68 mmol). After 3 hours, the reaction mixture was diluted with ethyl acetate, washed successively with saturated sodium bicarbonate and brine, dried over anhydrous magnesium sulfate and concentrated under reduced pressure. Chromatography of the residue on silica gel (elution ethyl acetate) followed by crystallization from ethyl acetate gave 0.246 g (92% yield) of the title amide as white crystals; mp 167° C. $^1$HNMR 400 MHz (CDCl$_3$) δ (ppm): 1.64 (6H, s, 2×CH$_3$), 2.70 (3H, s, CH$_3$), 4.0-4.08 (4H, m, 2×CH$_2$), 4.68 (2H, d, J=5.8 Hz, NCH$_2$), 5.32 (2H, s, OCH$_2$), 7.34-7.39 (3H, m, aromatics), 7.49 (1H, s, CH), 7.50-7.53 (2H, m, aromatics), 7.72 (1H, broad t, NH). Anal. Calcd for C$_{22}$H$_{24}$N$_4$O$_4$S: C, 59.98; H, 5.49; N, 12.71; Found: C, 59.99; H, 5.31; N, 12.61.

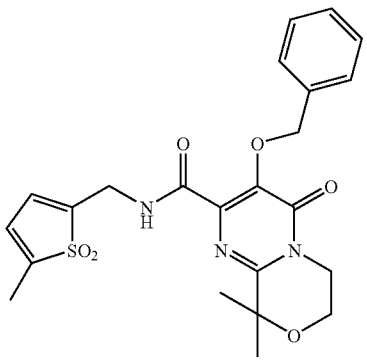

Intermediate 90

3-(Benzyloxy)-N-((5-methylthiophen-2-yl)methyl)-9,9-dimethyl-4-oxo-4,6,7,9-tetrahydropyrimido[2,1-c][1,4]oxazine-2-carboxamide sulfone. To a solution of 3-(benzyloxy)-N-((5-methylthiophen-2-yl)methyl)-9,9-dimethyl-4-oxo-4,6,7,9-tetrahydropyrimido[2,1-c][1,4]oxazine-2-carboxamide (70 mg, 0.16 mmol) in CH$_2$Cl$_2$ (5 mL) was added m-chloroperbenzoic acid (96 mg, 0.47 mmol; 80-90% active peracid, Aldrich) and the mixture stirred at room temperature overnight (24 h). The mixture diluted with CH$_2$Cl$_2$ (10 mL) was washed with 5% NaHSO$_4$ (10 mL) and then with saturated sodium bicarbonate (10 mL×2), brine, dried (Na$_2$SO$_4$), filtered and concentrated to a gum which was purified by column (SiO$_2$, 30% EtOAc/CH$_2$Cl$_2$) to obtain 23 mg (0.049 mmol, Y.30%) of the title compound as a lightly colored film: HPLC: 2.12 min (AP 93% at 254 nm); LC/MS m/z 472 (M+H); $^1$H NMR (500 MHz, CDCl$_3$) δ ppm 1.62 (6H, s, gem-CH$_3$), 2.11 (3H, s, Th—CH$_3$), 3.96-4.00 (2H, m, NCH$_2$), 4.01-4.05 (2H, m, OCH$_2$), 4.42 (2H, d, J=5.8 Hz, NCH$_2$), 5.30 (2H, s, OCH$_2$), 6.29 (1H, dd, J=4.3, 2.1 Hz, Th—H), 6.56 (1H, d, J=4.3 Hz, Th—H), 7.30 (1H, t, J=7.2 Hz, Ph-H), 7.35 (2H, t, J=7.5 Hz, Ph-H), 7.57 (2H, d, J=7.3 Hz, Ph-H), 8.03 (1H, t, J=5.6 Hz, NH); $^{13}$C NMR (125.8 MHz, CDCl$_3$) δ ppm 9.46 (CH$_3$), 27.8 (CH$_3$), 34.1 (CH$_2$), 43.0 (CH$_2$), 58.1 (CH$_2$), 74.9 (C), 76.3 (C), 122.4 (CH), 125.9 (CH), 128.4 (CH), 128.6 (CH), 128.9 (CH), 136.7 (C), 138.4 (C), 139.4 (C), 141.0 (C), 142.5 (C), 156.5 (C), 159.7 (C=O), 162.2 (C=O); HRMS (ESI) calcd for C$_{23}$H$_{26}$N$_3$O$_6$S (M+H) 472.1542, found 472.1547.

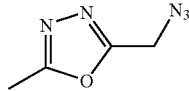

Intermediate 91

2-(Azidomethyl)-5-methyl-1,3,4-oxadiazole. A solution of 2-(chloromethyl)-5-methyl-1,3,4-oxadiazole (R. Rufenacht, Helv. Chim. Acta, 55, 1979, 1972) (2.00 g, 15.09 mmol) in N,N-dimethylformamide (75 ml) was treated at 22° C. with sodium azide (3.0 g, 46.1 mmol) and the resulting mixture was stirred for 18 h. The reaction mixture was diluted with ethyl acetate, washed with saturated sodium bicarbonate, brine and dried over anhydrous magnesium sulfate. Evaporation of the solvent under reduced pressure followed by chromatography of the residue on silica gel (elution toluene-ethyl acetate 0-10%) gave 1.78 g (84% yield) of the title azide as a clear oil. $^1$HNMR 400 MHz (CDCl$_3$) δ (ppm): 2.60 (3H, s, CH$_3$), 4.55 (2H, s, CH$_2$). MS (ESI$^+$) m/e 140 [M+H$^+$].

Intermediate 92

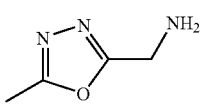

(5-Methyl-1,3,4-oxadiazol-2-yl)methanamine. A solution of 2-(azidomethyl)-5-methyl-1,3,4-oxadiazole (1.68 g, 12.08 mmol) in tetrahydrofuran (30 ml) was treated at 22° C. with triphenylphosphine (3.7 g, 14.1 mmol) and the resulting mixture was stirred for one hour. Water (0.5 ml) was then added and the mixture was stirred for another 18 h at 22° C. The solvent was then concentrated in vacuo and the residue was partitioned between dichloromethane and 1 N hydrochloric acid (50 ml). The aqueous phase was basified with sodium hydroxide, saturated with sodium chloride and extracted several times with ethyl acetate. The combined organic extracts were dried over anhydrous magnesium sulfate and concentrated to give 0.477 g (35% yield) of the title amine as a clear oil. $^1$HNMR 400 MHz (CDCl$_3$) δ (ppm): 2.54 (3H, s, CH$_3$), 4.04 (2H, m, CH$_2$).

Intermediate 93

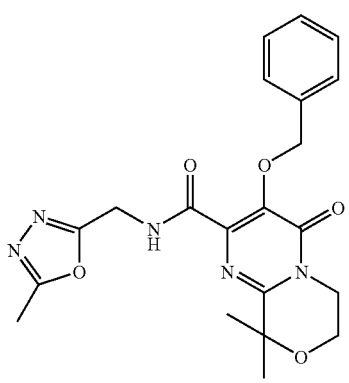

3-(Benzyloxy)-9,9-dimethyl-N-((5-methyl-1,3,4-oxadiazol-2-yl)methyl)-4-oxo-4,6,7,9-tetrahydropyrimido[2,1-c][1,4]oxazine-2-carboxamide. White crystals (85% yield); mp 181° C. (ethyl acetate). $^1$HNMR 400 MHz (CDCl$_3$) δ (ppm): 1.65 (6H, s, 2×CH$_3$), 2.54 (3H, s, CH$_3$), 4.0-4.08 (4H, m, 2×CH$_2$), 4.77 (2H, d, J=5.8 Hz, NCH$_2$), 5.35 (2H, s, OCH$_2$), 7.3-7.4 (3H, m, aromatics), 7.55-7.6 (2H, m, aromatics), 8.06 (1H, broad t, NH). Anal. Calcd for C$_{21}$H$_{23}$N$_5$O$_5$: C, 59.29; H, 5.45; N, 16.46; Found: C, 59.12; H, 5.37; N, 16.51.

Intermediate 94

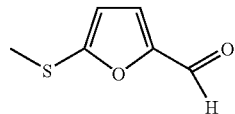

5-(Methylthio)furan-2-carbaldehyde. To a solution of 2-(diethoxymethyl)furan (2.00 g, 11.75 mmol) in dry THF (8 mL) was added a solution of n-BuLi (1.6 M in Hexane) (8.80 mL, 14.1 mmol) at −78° C. The resulting mixture was stirred at −78° C. for 1 h and treated with methyldisulfide (1.06 mL, 11.75 mmol). The reaction mixture was stirred at −78° C. for 30 min followed by warming to 0° C. for 1 hour. HCl (1N) (20 mL) was added and the organic material was extracted with ether (2×50 mL). The combined organic fractions were dried (MgSO4) and concentrated in vacuo to afford 1.58 g (94%) of crude title compound. LCMS ($^+$ESI, M+H$^+$) m/z 143.

Intermediate 95

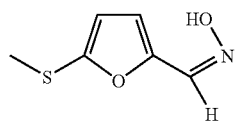

5-(Methylthio)furan-2-carbaldehyde oxime. To a solution of 5-(methylthio)furan-2-carbaldehyde (1.0 g, 7.04 mmol) in ethanol (10 mL) was added an aqueous solution of hydroxylamine hydrochloride (3.75M) (2.26 mL, 8.45 mmol) and an aqueous solution of sodium acetate (1.5 M) (3.78 mL, 5.63 mmol). The reaction mixture was stirred a 23° C. for 18 hours. The ethanol was concentrated in vacuo, H$_2$O was added (50 mL) and the precipitate was filtered and dried in oven (60° C.) for 10 minutes to afford 277 mg (25%) of the title compound. LCMS ($^+$ESI, M+H$^+$) m/z 158.

Intermediate 96

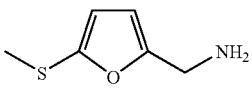

(5-(Methylthio)furan-2-yl)methanamine. To a solution of 5-(methylthio)furan-2-carbaldehyde oxime (220 mg, 1.40 mmol) in glacial acetic acid (15 mL) was added zinc dust (2.10 g, 32.2 mmol) and the reaction mixture was stirred at 23° C. for 4 h. After filtration on celite, the acetic acid was concentrated in vacuo and the crude material purified on functionalized silica gel (6 g) containing sulfonic acid (0.8 mmol/g) to afford 138 mg (69%) of the title compound as an orange oil. $^1$H NMR (400 MHz, CDCl$_3$): 6.36 (1H, d, J=3.2 Hz), 6.11 (1H, d, J=3.2 Hz), 3.80 (2H, s), 2.36 (3H, s).

Intermediate 97

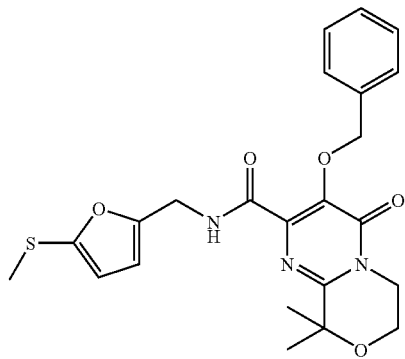

3-(Benzyloxy)-9,9-dimethyl-N-((5-(methylthio)furan-2-yl)methyl)-4-oxo-4,6,7,9-tetrahydropyrimido[2,1-c][1,4]oxazine-2-carboxamide. $^1$H NMR (400 MHz, CDCl$_3$): 7.73 (1H, br s), 7.50-7.57 (2H, m), 7.31-7.41 (3H, m), 6.39 (1H, d, 3.2 Hz), 6.24 (1H, d, J=3.3 Hz), 5.34 (2H, s), 4.55 (2H, d, J=5.8 Hz), 3.99-4.10 (4H, m), 2.40 (3H, s), 1.66 (6H, s). LCMS ($^+$ESI, M+H$^+$) m/z 456.

Intermediate 98

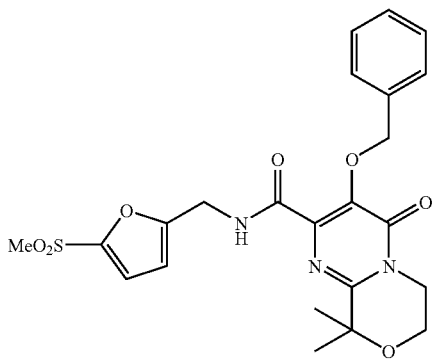

3-(Benzyloxy)-9,9-dimethyl-N-((5-(methylsulfonyl)furan-2-yl)methyl)-4-oxo-4,6,7,9-tetrahydropyrimido[2,1-c][1,4]oxazine-2-carboxamide. To a solution of 3-(benzyloxy)-9,9-dimethyl-N-((5-(methylthio)furan-2-yl)methyl)-4-oxo-4,6,7,9-tetrahydropyrimido[2,1-c][1,4]oxazine-2-carboxamide (50 mg, 0.13 mmol) in CH$_2$Cl$_2$ (5 mL) was added peracetic acid (32%) (0.250 mL, 1.3 mmol). The reaction mixture was stirred at 23° C. for 18 h and then treated with H$_2$O (25 mL). The organic material was extracted with CH$_2$Cl$_2$ (2×25 mL), the combined organic fractions were dried (MgSO$_4$) and the solvent removed under vacuo to afford 17 mg (27%) of the title compound as a beige solid. LCMS ($^+$ESI, M+H$^+$) m/z 488.

Example 1

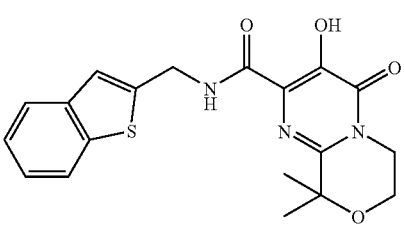

Pyrimido[2,1-c][1,4]oxazine-2-carboxamide, N-(benzo[b]thien-2-ylmethyl)-4,6,7,9-tetrahydro-3-hydroxy-9,9-dimethyl-4-oxo-. $^1$H NMR (500 MHz, DMSO-d$_6$) δ 1.57 (s, 6H) 3.84 (t, J=5.04 Hz, 2H) 3.97 (t, J=5.04 Hz, 2H) 4.75 (d, J=6.41 Hz, 2 H) 7.29-7.37 (m, 3H) 7.80 (d, J=7.93 Hz, 1H) 7.91 (d, J=7.94 Hz, 1H) 9.59 (s, 1 H) 12.13 (s, 1H). $^{13}$C NMR (125.8 MHz, DMSO-d$_6$) δ 27.52, 38.12, 42.74, 57.35, 75.34, 122.11, 122.35, 123.27, 124.09, 124.31, 125.23, 138.95, 139.07, 142.42, 151.72, 156.94, 168.38. Anal. Calcd for C$_{19}$H$_{19}$N$_3$O$_4$S: C, 59.20; H, 4.96; N, 10.90. Found: C, 59.24; H, 4.86; N, 10.75.

Example 2

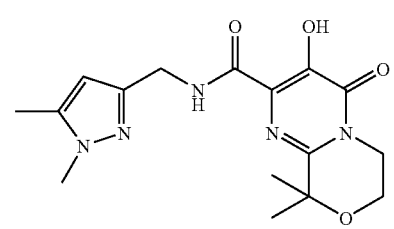

Pyrimido[2,1-c][1,4]oxazine-2-carboxamide, N-[(1,5-dimethyl-1H-pyrazol-3-yl)methyl]-4,6,7,9-tetrahydro-3-hydroxy-9,9-dimethyl-4-oxo-. $^1$H NMR (500 MHz, DMSO-d$_6$) δ 1.56 (s, 6H) 2.19 (s, 3H) 3.66 (s, 3H) 3.83 (t, J=5.04 Hz, 2H) 3.97 (t, J=5.04 Hz, 2H) 4.35 (d, J=6.41 Hz, 2H) 5.93 (s, 1H) 9.25 (s, 1H) 12.35 (s, 1H). $^{13}$C NMR (125.8 MHz, DMSO-d$_6$) δ 10.56, 27.47, 35.55, 36.38, 42.71, 57.35, 75.32, 103.58, 125.39, 139.05, 145.35, 146.84, 1515.55, 156.96, 168.03.

Anal. Calcd for $C_{16}H_{21}N_5O_4$: C, 55.32; H, 6.09; N, 20.16. Found: C, 55.41; H, 6.27; N, 20.44.

Example 3

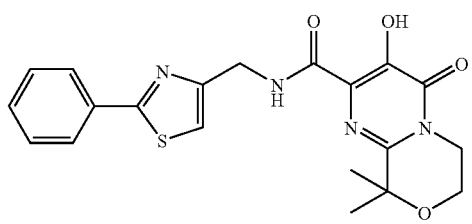

Pyrimido[2,1-c][1,4]oxazine-2-carboxamide, 4,6,7,9-tetrahydro-3-hydroxy-9,9-dimethyl-4-oxo-N-[(2-phenyl-4-thiazolyl)methyl]-. $^1$H NMR (500 MHz, DMSO-d$_6$) δ 1.59 (s, 6H) 3.84 (t, J=5.04 Hz, 2H) 3.98 (t, J=5.04 Hz, 2H) 4.66 (d, J=6.10 Hz, 2H) 7.49-7.51 (m, 3H) 7.93 (dd, J=7.63, 1.83 Hz, 2H) 9.48 (s, 1H) 12.19 (s, 1 H). $^{13}$C NMR (125.8 MHz, DMSO-d$_6$) δ 27.52, 42.74, 57.37, 75.35, 115.96, 125.41, 125.93, 129.18, 130.19, 132.87, 145.35, 151.67, 154.03, 156.98, 166.97, 168.33. Anal. Calcd for $C_{20}H_{20}N_4O_4S$: C, 58.24; H, 4.88; N, 13.58. Found: C, 58.10; H, 4.77; N, 13.40.

Example 4

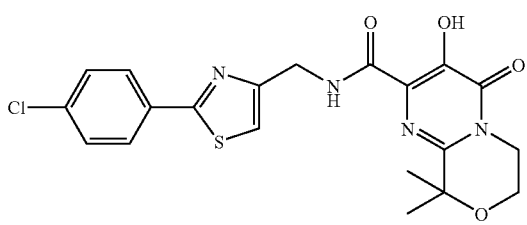

Pyrimido[2,1-c][1,4]oxazine-2-carboxamide, N-[[2-(4-chlorophenyl)-4-thiazolyl]methyl]-4,6,7,9-tetrahydro-3-hydroxy-9,9-dimethyl-4-oxo-. $^1$H NMR (500 MHz, DMSO-d$_6$) δ 1.58 (s, 6H) 3.84 (t, J=5.04 Hz, 2H) 3.98 (t, J=5.04 Hz, 2 H) 4.65 (d, J=6.10 Hz, 2H) 7.52 (s, 1H) 7.57 (d, J=8.55 Hz, 2H) 7.94 (d, J=8.55 Hz, 2H) 9.48 (t, J=6.10 Hz, 1H) 12.17 (s, 1H). $^{13}$C NMR (125.8 MHz, DMSO-d$_6$) δ 27.52, 42.74, 57.37, 75.35, 116.55, 125.39, 127.62, 129.24, 131.70, 134.70, 145.35, 151.35, 151.67, 154.23, 165.60, 168.35. Anal. Calcd for $C_{20}H_{19}ClN_4O_4S$: C, 53.75, H, 4.28; N, 12.53. Found: C, 53.70; H, 4.25; N, 12.38.

Example 5

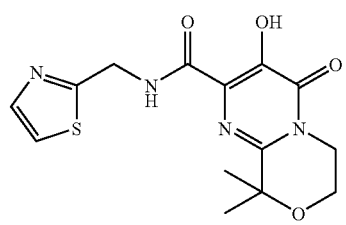

Pyrimido[2,1-c][1,4]oxazine-2-carboxamide, 4,6,7,9-tetrahydro-3-hydroxy-9,9-dimethyl-4-oxo-N-(2-thiazolylmethyl)-. $^1$H NMR (500 MHz, DMSO-d$_6$) δ 1.57 (s, 6H) 3.84 (t, J=4.73 Hz, 2H) 3.98 (t, J=4.88 Hz, 2H) 4.79 (d, J=6.10 Hz, 2H) 7.66 (m, 1H) 7.75 (m, 1H) 9.68 (t, J=6.26 Hz, 1H) 11.93 (s, 1H). $^{13}$C NMR (125.8 MHz, DMSO-d$_6$) δ 27.49, 40.39, 42.75, 57.35, 75.35, 120.34, 125.14, 142.11, 145.38, 151.81, 156.94, 167.61, 168.51.

Example 6

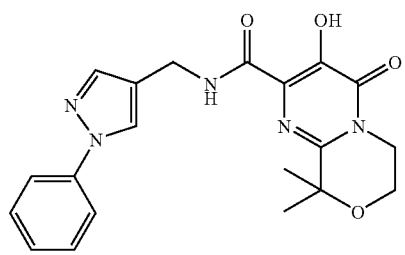

Pyrimido[2,1-c][1,4]oxazine-2-carboxamide, 4,6,7,9-tetrahydro-3-hydroxy-9,9-dimethyl-4-oxo-N-[(1-phenyl-1H-pyrazol-4-yl)methyl]-. $^1$H NMR (500 MHz, DMSO-d$_6$) δ 1.56 (s, 6H) 3.83 (t, J=5.04 Hz, 2H) 3.97 (t, J=5.04 Hz, 2H) 4.43 (d, J=6.41 Hz, 2H) 7.29 (t, J=7.48 Hz, 1H) 7.48 (t, J=7.78 Hz, 2H) 7.71 (s, 1H) 7.80 (d, J=7.63 Hz, 2H) 8.40 (s, 1H) 9.32 (s, 1H) 12.34 (s, 1H). $^{13}$C NMR (125.8 MHz, DMSO-d$_6$) δ 27.52, 33.00, 42.71, 57.35, 75.32, 118.11, 120.67, 125.46, 126.04, 126.33, 129.42, 139.51, 140.56, 145.36, 151.55, 156.97, 168.19. Anal Calcd for $C_{20}H_{21}N_5O_4$: C, 60.75; H, 5.35; N 17.71. Found: C, 60.94; H, 5.29; N, 17.85.

Example 7

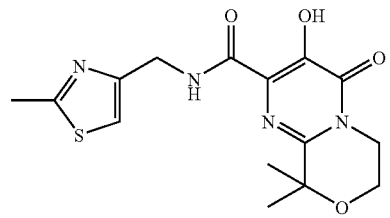

Pyrimido[2,1-c][1,4]oxazine-2-carboxamide, 4,6,7,9-tetrahydro-3-hydroxy-9,9-dimethyl-N-[(2-methyl-4-thiazolyl)methyl]-4-oxo-. $^1$H NMR (500 MHz, DMSO-d$_6$) δ 1.60 (s, 6H) 2.60-2.65 (m, 3H) 3.79-3.87 (m, 2H) 3.93-4.01 (m, 2H) 4.53 (d, J=6.41 Hz, 2H) 7.19-7.26 (br s, 1H) 9.38 (d, J=5.80 Hz, 1H), 12.24 (br s, 1). $^3$C NMR (125.8 MHz, DMSO-d$_6$) δ

28.50, 42.73, 57.35, 75.33, 114.97, 125.37, 145.36, 151.62, 152.27, 156.95, 165.46, 168.22.

Example 8

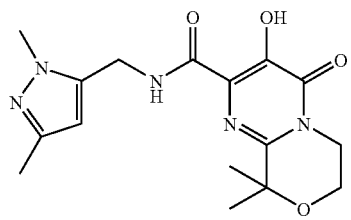

Pyrimido[2,1-c][1,4]oxazine-2-carboxamide, N-[(1,3-dimethyl-1H-pyrazol-5-yl)methyl]-4,6,7,9-tetrahydro-3-hydroxy-9,9-dimethyl-4-oxo-. $^1$H NMR (500 MHz, DMSO-$d_6$) δ 1.57 (s, 6H) 2.07 (s, 3H) 3.74 (s, 3H) 3.83 (t, J=5.04 Hz, 2H) 3.97 (t, J=5.19 Hz, 2H) 4.47 (d, J=6.41 Hz, 2H), 5.92 (s, 1), 9.33 (br s, 1), 12.02 (br s, 1). $^{13}$C NMR (125.8 MHz, DMSO-$d_6$) δ 13.08, 27.53, 33.52, 35.86, 42.72, 57.35, 75.31, 104.78, 125.26, 139.66, 145.41, 157.02, 168.15. Anal. Calcd for $C_{16}H_{21}N_5O_4$: C, 55.32; H, 6.09; N, 20.16. Found: C, 55.14; H, 5.99; N, 20.44.

Example 9

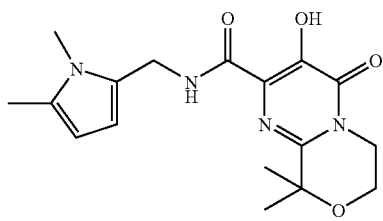

Pyrimido[2,1-c][1,4]oxazine-2-carboxamide, N-[(1,5-dimethyl-1H-pyrrol-2-yl)methyl]-4,6,7,9-tetrahydro-3-hydroxy-9,9-dimethyl-4-oxo-. $^1$H NMR (500 MHz, CHLOROFORM-D) δ 1.51 (s, 6H), 2.23 (s, 3H) 3.42-3.49 (m, 4H) 4.01 (s, 3H) 4.55-4.62 (m, 2H) 5.85 (s, 1H) 6.06 (s, 1H) 7.48 (s, 1H) 12.11 (s, 1H). $^{13}$C NMR (125.8 MHz, DMSO-$d_6$) δ 12.10, 27.52, 30.02, 34.69, 42.71, 57.33, 75.29, 104.85, 106.88, 125.42, 127.49, 128.45, 145.40, 151.54, 156.98, 167.71.

Example 10

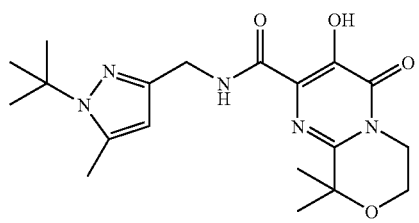

Pyrimido[2,1-c][1,4]oxazine-2-carboxamide, N-[[1-(1,1-dimethylethyl)-5-methyl-1H-pyrazol-3-yl]methyl]-4,6,7,9-tetrahydro-3-hydroxy-9,9-dimethyl-4-oxo-. $^1$H NMR (500 MHz, DMSO-$d_6$) δ 1.55 (s, 12H) 2.37 (s, 3H) 3.83 (t, J=5.04 Hz, 2 H) 3.97 (t, J=5.04 Hz, 2H) 4.35 (d, J=6.10 Hz, 2H) 5.96 (s, 1H) 9.24 (s, 1H) 12.31 (s, 1H.). $^{13}$C NMR (125.8 MHz, DMSO-$d_6$) δ 14.07, 27.46, 29.68, 36.71, 42.71, 57.37, 59.15, 75.29, 106.55, 125.39, 138.73, 144.87, 145.31, 151.61, 156.96, 168.02. Anal. Calcd for $C_{19}H_{27}N_5O_4$: C, 58.59; H, 6.98; N, 17.98. Found: C, 58.36; H, 7.03; N, 18.03.

Example 11

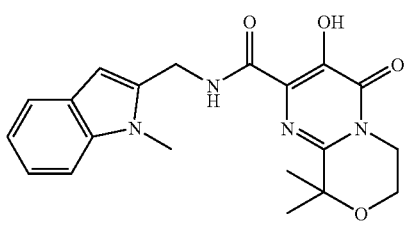

Pyrimido[2,1-c][1,4]oxazine-2-carboxamide, 4,6,7,9-tetrahydro-3-hydroxy-9,9-dimethyl-N-[(1-methyl-1H-indol-2-yl)methyl]-4-oxo-. $^1$H NMR (500 MHz, DMSO-$d_6$) δ 1.57 (d, J=5.19 Hz, 6H) 3.77 (s, 3H) 3.83 (d, J=4.27 Hz, 2H) 3.97 (d, J=4.27 Hz, 2H) 4.67-4.75 (m, 2H) 6.35 (d, J=7.32 Hz, 1H) 6.99 (d, J=7.02 Hz, 1H) 7.11 (d, J=7.63 Hz, 1H) 7.37-7.45 (m, 1H) 7.45-7.52 (m, 1H) 9.34 (d, J=5.49 Hz, 1H) 12.14-12.21 (m, 1H). $^{13}$C NMR (125.8 MHz, DMSO-$d_6$) δ 27.53, 29.57, 35.05, 42.73, 57.35, 75.32, 100.18, 109.44, 119.04, 119.74, 120.82, 125.39, 126.81, 136.90, 137.12, 145.33, 151.70, 156.95, 168.16. Anal Calcd for $C_{20}H_{22}N_4O_4$: C, 62.81; H, 5.79; N, 14.65. Found: C, 62.57; H, 5.92; N, 14.47.

Example 12

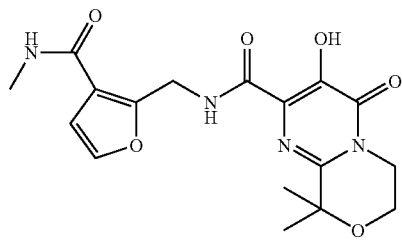

Pyrimido[2,1-c][1,4]oxazine-2-carboxamide, 4,6,7,9-tetrahydro-3-hydroxy-9,9-dimethyl-N-[[3-[(methylamino)carbonyl]-2-furanyl]methyl]-4-oxo-. $^1$H NMR (500 MHz, DMSO-$D_6$) δ ppm 1.56 (s, 6H) 2.76 (d, J=4.27 Hz, 3H) 3.79-3.86 (m, 2 H) 3.95-4.04 (m, 2H) 4.80 (d, J=6.41 Hz, 2H) 6.88 (d, J=1.83 Hz, 1H) 7.62 (d, J=1.83 Hz, 1H) 8.24 (d, J=4.58 Hz, 1H) 9.64 (t, J=6.10 Hz, 1H) 12.02 (s, 1H). $^{13}$C NMR (125.8 MHz, DMSO-$d_6$) δ 25.52, 27.47, 35.16, 42.70, 57.38, 75.31, 109.24, 117.34, 125.25, 141.63, 145.29, 151.69, 153.93, 156.95, 162.91, 167.88.

Example 13

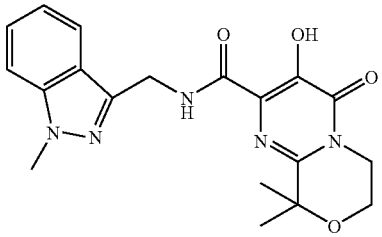

Pyrimido[2,1-c][1,4]oxazine-2-carboxamide, 4,6,7,9-tetrahydro-3-hydroxy-9,9-dimethyl-N-[(1-methyl-1H-indazol-3-yl)methyl]-4-oxo-. $^1$H NMR (500 MHz, DMSO-$d_6$) δ 1.55 (s, 6H) 3.82 (t, J=5.04 Hz, 2H) 3.94 (m, 2H) 4.02 (s, 3H) 4.82 (d, J=6.10 Hz, 2H) 7.11 (t, J=7.48 Hz, 1H) 7.36-7.42 (m, 1H) 7.60 (d, J=8.54 Hz, 1H) 7.85 (d, J=8.24 Hz, 1H) 9.53 (t, J=6.26 Hz, 1H) 12.26 (s, 1H). Anal. calcd. for $C_{19}H_{21}N_5O_4$: C, 59.52; 5.52, 18.26; Found: C, 59.63; H, 5.50; N, 18.29.

Example 14

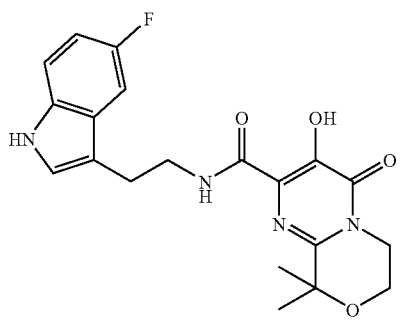

Pyrimido[2,1-c][1,4]oxazine-2-carboxamide, N-[2-(5-fluoro-1H-indol-3-yl)ethyl]-4,6,7,9-tetrahydro-3-hydroxy-9,9-dimethyl-4-oxo-. $^1$H NMR (500 MHz, DMSO-$d_6$) δ 1.55 (s, 6H) 2.96 (t, J=7.17 Hz, 2H) 3.56 (q, J=6.61 Hz, 2H) 3.83 (m, 2H) 3.97 (d, J=3.97 Hz, 2H) 6.84 (t, J=9.16 Hz, 1H) 7.11 (d, J=10.07 Hz, 1H) 7.21 (s, 1H) 7.54-7.61 (m, 1H) 8.90 (s, 1H) 10.94 (s, 1H) 12.38 (s, 1H). $^{13}$C NMR (125.8 MHz, DMSO-$d_6$) δ 24.64, 27.50, 42.70, 57.36, 75.28, 97.14, 97.34, 106.62, 106.81, 111.54, 119.24, 123.27, 123.97, 125.33, 136.02, 145.27, 151.54, 156.96, 157.85, 159.72, 168.06.

Anal. Calcd for $C_{20}H_{21}FN_4O_4$: C, 59.99; H, 5.28; N, 13.99. Found: C, 59.86; H, 5.21; N, 13.95.

Example 15

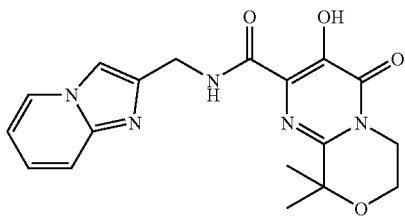

Pyrimido[2,1-c][1,4]oxazine-2-carboxamide, 4,6,7,9-tetrahydro-3-hydroxy-N-(imidazo[1,2-a]pyridin-2-ylmethyl)-9,9-dimethyl-4-oxo-. $^1$H NMR (500 MHz, DMSO-$d_6$) δ 1.58 (s, 6H) 3.85 (t, J=5.04 Hz, 2H) 3.99 (m, 2H) 4.74 (d, J=6.10 Hz, 2H) 7.38 (t, J=6.87 Hz, 1H) 7.78-7.83 (m, 1H) 7.85-7.89 (m, 1H) 8.20 (s, 1H) 8.81 (d, J=6.71 Hz, 1H) 9.50 (t, J=6.10 Hz, 1H) 11.97 (s, 1H). Anal. Calcd for $C_{18}H_{19}N_5O_4$—$CF_3CO_2H$: C, 49.69; H, 4.17; N, 14.49. Found: C, 50.03; H, 4.17; N, 14.44.

Example 16

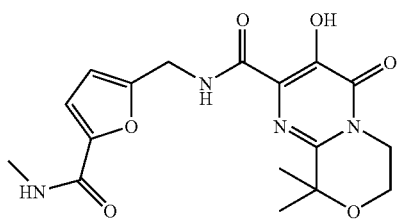

3-Hydroxy-9,9-dimethyl-N-((5-(methylcarbamoyl)-2-furyl)methyl)-4-oxo-4,6,7,9-tetrahydropyrimido[2,1-c][1,4]oxazine-2-carboxamider. $^1$H NMR (500 MHz, DMSO-$d_6$) δ 1.57 (s, 6H) 2.72 (d, J=4.58 Hz, 3H) 3.81-3.88 (m, 2H) 3.97 (t, J=5.19 Hz, 2H) 4.53 (d, J=6.10 Hz, 2H) 6.40 (d, J=3.36 Hz, 1H) 7.01 (d, J=3.36 Hz, 1H) 8.20 (d, J=4.58 Hz, 1H) 9.38 (s, 1H) 12.09 (s, 1H). $^{13}$C NMR (125.8 MHz, DMSO-$d_6$) δ 25.38; 27.50; 35.78; 42.74; 57.35; 75.33; 109.00, 113.54, 125.27, 145.38, 146.98, 151.70, 153.42, 156.95, 158.09, 168.34. Anal. Calcd for $C_{17}H_{20}N_4O_6$: C, 54.25; H, 5.35; N, 14.88. Found: C, 54.11; H, 5.14; N, 14.68.

Example 17

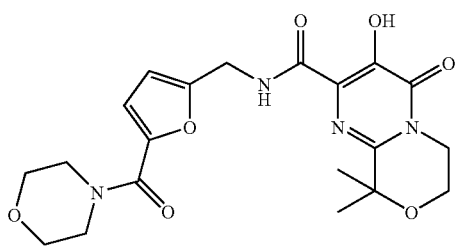

Pyrimido[2,1-c][1,4]oxazine-2-carboxamide, 4,6,7,9-tetrahydro-3-hydroxy-9,9-dimethyl-N-[[5-(4-morpholinylcarbonyl)-2-furanyl]methyl]-4-oxo-. $^1$H NMR (500 MHz, DMSO-d$_6$) δ 1.56 (s, 6H) 3.60-3.65 (overlapping m, 6H,) 3.83 (t, J=5.04 Hz, 2H) 3.97 (t, J=5.04 Hz, 2H) 4.53 (d, J=6.10 Hz, 2H) 6.45 (d, J=3.36 Hz, 1H) 6.96 (d, J=3.36 Hz, 1H) 9.42 (s, 1H) 12.08 (br s, 1H). $^{13}$C NMR (125.8 MHz, DMSO-d$_6$) δ 27.48, 35.67, 42.73, 57.35, 66.10, 75.32, 108.62, 116.67, 125.23, 145.37, 145.73, 151.70, 153.28, 156.95, 158.04, 168.42. Anal. Calcd for C$_{20}$H$_{24}$N$_4$O$_7$-0.5 (CF$_3$CO$_2$H): C, 51.53; H, 5.05; N, 11.45. Found: C, 51.35; H, 5.06; N, 11.07.

Example 18

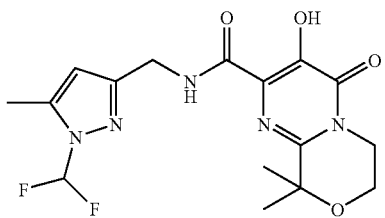

Pyrimido[2,1-c][1,4]oxazine-2-carboxamide, N-[[1-(difluoromethyl)-5-methyl-1H-pyrazol-3-yl]methyl]-4,6,7,9-tetrahydro-3-hydroxy-9,9-dimethyl-4-oxo-. $^1$H NMR (500 MHz, DMSO-d$_6$) δ1.57 (s, 6H) 2.16 (s, 3H) 3.84 (t, J=4.88 Hz, 2H) 3.96 (m, 2H) 4.64 (d, J=6.10 Hz, 2H) 6.16 (s, 1H), 7.83 (t, J=57.68 Hz, 1 H), 9.38 (t, J=6.10 Hz, 1H), 11.89 (s, 1H). $^{13}$C NMR (125.8 MHz, DMSO-d$_6$) δ 13.11, 27.51, 33.26, 42.74, 57.36, 75.32, 107.81-111.73 (triplet), 108.30, 125.15, 141.59, 145.26, 150.44, 151.78, 156.92, 168.35.

Example 19

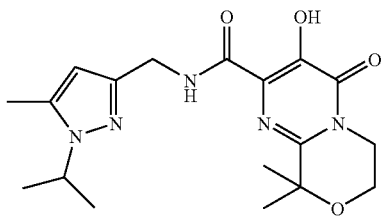

Pyrimido[2,1-c][1,4]oxazine-2-carboxamide, 4,6,7,9-tetrahydro-3-hydroxy-9,9-dimethyl-N-[[5-methyl-1-(1-methylethyl)-1H-pyrazol-3-yl]methyl]-4-oxo-. $^1$H NMR (500 MHz, DMSO-d$_6$) δ1.34 (d, J=6.71 Hz, 6H) 1.56 (s, 6H) 2.22 (s, 3H) 3.83 (t, J=5.04 Hz, 2H) 3.97 (t, J=5.19 Hz, 2H) 4.37 (d, J=6.10 Hz, 2H), 4.43 (heptet, J=6.71 Hz, 1H), 5.91 (s, 1H), 9.27 (m, 1H), 12.31 (s, 1H). $^{13}$C NMR (125.8 MHz, DMSO-d$_6$) δ 10.40, 22.37, 27.46, 36.79, 42.71, 48.49, 57.38, 75.30, 103.34, 125.39, 137.93, 145.31, 146.74, 151.61, 156.97, 168.01. Anal. Calcd for C$_{18}$H$_{25}$N$_5$O$_4$: C, 57.58; H, 6.71; N, 18.65. Found: C, 57.75; H, 6.52; N, 18.58.

Example 20

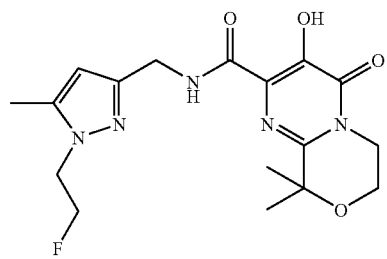

Pyrimido[2,1-c][1,4]oxazine-2-carboxamide, N-[[1-(2-fluoroethyl)-5-methyl-1H-pyrazol-3-yl]methyl]-4,6,7,9-tetrahydro-3-hydroxy-9,9-dimethyl-4-oxo-. $^1$H NMR (500 MHz, DMSO-d$_6$) δ ppm 1.56 (s, 6H) 2.22 (s, 3H) 3.83 (t, J=4.88 Hz, 2H) 3.97 (t, J=4.88 Hz, 2H) 4.32 (t, J=4.58 Hz, 1H) 4.38 (d, J=6.10 Hz, 2H) 4.76 (t, J=4.58 Hz, 1H), 5.97 (s, 2H), 9.30 (br s, 1H), 12.32 (s, 1H). $^{13}$C NMR (125.8 MHz, DMSO d$_6$) δ ppm 10.47, 27.47, 36.49, 40.12, 42.72, 48.51, 57.36, 75.32, 81.66, 82.99, 103.86, 125.39, 139.93, 145.35, 147.92, 151.59, 156.97, 168.11.

Example 21

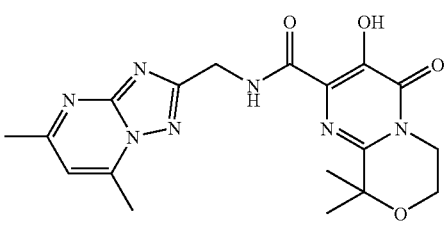

Pyrimido[2,1-c][1,4]oxazine-2-carboxamide, N-[(5,7-dimethyl[1,2,4]triazolo[1,5-a]pyrimidin-2-yl)methyl]-4,6,7,9-tetrahydro-3-hydroxy-9,9-dimethyl-4-oxo-. $^1$H NMR (500 MHz, DMSO-d$_6$) δ ppm 1.59 (s, 6H) 2.57 (s, 3 H) 2.71 (2, 3H) 3.17 (d, J=5.19 Hz, 1H) 3.85 (t, J=5.04 Hz, 2H) 3.99 (t, J=5.19 Hz, 2H) 4.73 (d, J=6.10 Hz, 2H), 7.16 (s, 1H), 9.44 (m, 1H), 12.10 (s, 1H). $^{13}$C NMR (125.8 MHz, DMSO-d$_6$) δ 16.44, 24.39, 27.52, 37.30, 42.74, 57.38, 75.33, 110.68, 125.29, 145.38, 146.73, 151.72, 154.96, 156.97, 164.34, 168.37.

Anal. Calcd for $C_{18}H_{21}N_7O_4$: C, 54.12; H, 5.29; N, 24.54. Found: C, 54.25; H, 5.54; N, 24.76.

Example 22

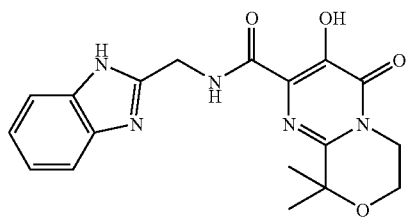

Pyrimido[2,1-c][1,4]oxazine-2-carboxamide, N-(1H-benzimidazol-2-ylmethyl)-4,6,7,9-tetrahydro-3-hydroxy-9,9-dimethyl-4-oxo-. $^1$HNMR (500 MHz, DMSO-$d_6$) δ ppm 1.59 (s, 6H) 3.87 (t, J=5.04 Hz, 2H) 4.00 (t, J=5.04 Hz, 2H) 4.95 (d, J=5.80 Hz, 2H) 7.46 (dd, J=6.26, 3.20 Hz, 2H) 7.74 (dd, J=5.95, 3.20 Hz, 2H) 9.55 (s, 1H), 11.72 (br s, 1). $^{13}$C NMR (125.8 MHz, DMSO-$d_6$) δ 27.52, 35.93, 42.79, 57.39, 75.32, 114.15, 124.62, 125.27, 145.23, 151.28, 151.76, 156.95, 158.05, 158.32, 168.93. Anal. Calcd for $C_{18}H_{19}N_5O_4$—$CF_3CO_2H$: C, 49.69; H, 4.17; N, 14.49. Found: C, 49.59; H, 4.10; N, 14.35.

Example 23

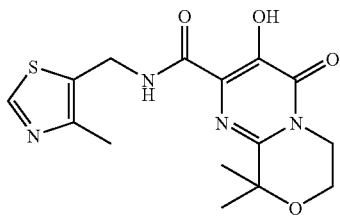

Pyrimido[2,1-c][1,4]oxazine-2-carboxamide, 4,6,7,9-tetrahydro-3-hydroxy-9,9-dimethyl-N-[(4-methyl-5-thiazolyl)methyl]-4-oxo-. $^1$HNMR 400 MHz (DMSO-$d_6$) δ (ppm): 1.56 (6H, s, 2×$CH_3$), 2.44 (3H, s, $CH_3$), 3.82 (2H, t, J=5 Hz, $CH_2$), 3.97 (2H, t, J=5 Hz, $CH_2$), 4.62 (2H, d, J=6.1 Hz, $NCH_2$), 8.87 (1H, s, CH), 9.50 (1H, broad, NH), 12.09 (1H, s, OH). HRMS (ESI$^-$) calculated for $C_{15}H_{19}N_4O_4S$ [M+H$^+$]: 351.1127; found: 351.1114.

Example 24

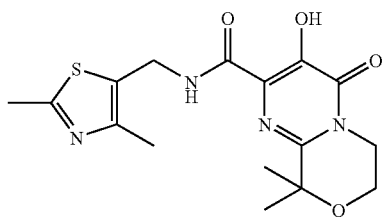

Pyrimido[2,1-c][1,4]oxazine-2-carboxamide, N-[(2,4-dimethyl-5-thiazolyl)methyl]-4,6,7,9-tetrahydro-3-hydroxy-9,9-dimethyl-4-oxo-: $^1$HNMR 400 MHz (DMSO-$d_6$) δ (ppm): 1.56 (6H, s, 2×$CH_3$), 2.35 (3H, s, $CH_3$), 2.53 (3H, s, $CH_3$), 3.83 (2H, t, J=5 Hz, $CH_2$), 3.97 (2H, t, J=5 Hz, $CH_2$), 4.53 (2H, d, J=6.1 Hz, $NCH_2$), 9.42 (1H, broad t, NH), 12.13 (1H, s, OH). HRMS (ESI$^+$) calculated for $C_{16}H_{21}N_4O_4S$ [M+H$^+$]: 365.1284; found: 365.1284.

Example 25

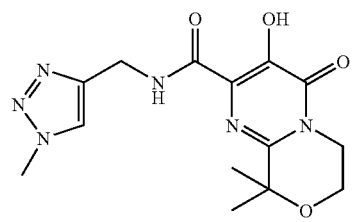

Pyrimido[2,1-c][1,4]oxazine-2-carboxamide, 4,6,7,9-tetrahydro-3-hydroxy-9,9-dimethyl-N-[(1-methyl-1H-1,2,3-triazol-4-yl)methyl]-4-oxo-. $^1$HNMR 400 MHz (DMSO-$d_6$) δ (ppm): 1.56 (6H, s, 2×$CH_3$), 3.83 (2H, t, J=5 Hz, $CH_2$), 3.97 (2H, t, J=5 Hz, $CH_2$), 4.02 (3H, s, $NCH_3$), 4.52 (2H, d, J=6.1 Hz, $NCH_2$), 9.47 (1H, broad, NH), 12.24 (1H, s, OH). HRMS (ESI$^+$) calculated for $C_{14}H_{19}N_6O_4$ [M+H$^+$]: 335.1468; found: 335.1483.

Example 26

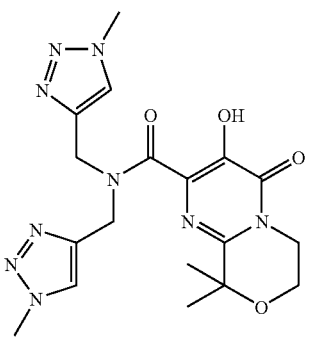

Pyrimido[2,1-c][1,4]oxazine-2-carboxamide, 4,6,7,9-tetrahydro-3-hydroxy-9,9-dimethyl-N,N-bis[(1-methyl-1H-1,2,3-triazol-4-yl)methyl]-4-oxo-. $^1$HNMR 400 MHz (DMSO-$d_6$) δ (ppm): 1.40 (6H, s, 2×$CH_3$), 3.86 (2H, t, J=4.5 Hz, $CH_2$), 3.98 (2H, t, J=4.5 Hz, $CH_2$), 3.99 (3H, s, $NCH_3$), 4.05 (3H, s, $NCH_3$), 4.51 (2H, s, $NCH_2$), 4.63 (2H, s, $NCH_2$), 7.83 (1H, s, CH), 7.96 (1H, s, CH), 10.04 (1H, s, OH). HRMS (ESI+) calculated for $C_{18}H_{24}N_9O_4$ [M+H+]: 430.1951; found: 430.1938.

Example 27

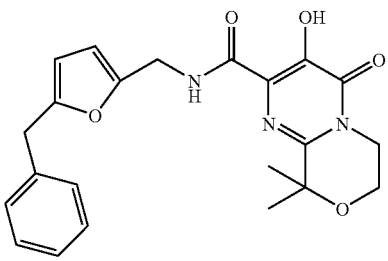

Pyrimido[2,1-c][1,4]oxazine-2-carboxamide, 4,6,7,9-tetrahydro-3-hydroxy-9,9-dimethyl-4-oxo-N-[[5-(phenylmethyl)-2-furanyl]methyl]. $^1$HNMR 400 MHz (CDCl$_3$) δ (ppm): 1.59 (6H, s, 2×CH$_3$), 3.98 (2H, s, CH$_2$), 4.04 (4H, s, 2×CH$_2$), 4.57 (2H, d, J=6.1 Hz, NCH$_2$), 5.99 (1H, d, J=3 Hz, CH), 6.23 (1H, d, J=3 Hz, CH), 7.2-7.35 (5H, m, aromatics), 7.75 (1H, broad, NH), 11.97 (1H, s, OH). HRMS (ESI+) calculated for $C_{22}H_{24}N_3O_5$ [M+H+]: 410.1716; found: 410.1735.

Example 28

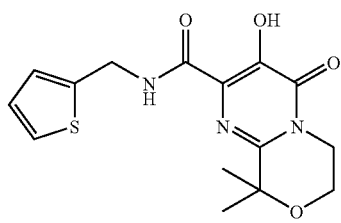

Pyrimido[2,1-c][1,4]oxazine-2-carboxamide, 4,6,7,9-tetrahydro-3-hydroxy-9,9-dimethyl-4-oxo-N-(2-thienylmethyl)-. A solution of ethyl 3-hydroxy-9,9-dimethyl-4-oxo-4,6,7,9-tetrahydropyrimido[2,1-c][1,4]oxazine-2-carboxylate (50 mg, 0.19 mmol) and 2-aminomethylthiophene (84 mg, 0.74 mmol: Aldrich) in DMF (1 mL; Sure Seal) was stirred in an oil bath heated at 100° C. under nitrogen for 1.5 h. The solvent was concentrated in vacuo and the residue, diluted in CH$_2$Cl$_2$ (10 mL), was washed with 1N HCl (5 mL), brine, dried (Na$_2$SO$_4$), filtered, and concentrated. The residue was crystallized from 95% EtOH to obtain 43 mg (69% yield) of the title compound as an off-white crystalline powder: HPLC, 2.15 min (at 254 nm); $^1$H NMR (500 MHz, CDCl$_3$) δ ppm 1.57 (6H, s, 2CH$_3$), 4.01 (4H, s, N, O—CH$_2$), 4.78 (2H, d, J=6.1 Hz, N—CH$_2$), 6.95-7.01 (1H, m, Th—H), 7.04 (1H, d, J=3.4 Hz, Th—H), 7.23-7.30 (1H, m, Th—H), 7.81 (1H, s, NH), 11.92 (1H, s, OH); $^{13}$C NMR (125.8 MHz, CDCl$_3$) δ ppm 28.1 (CH$_3$), 38.0 (NCH$_2$), 43.2 (NCH$_2$), 58.2 (OCH$_2$), 75.9 (C), 125.4 (C), 125.7 (CH), 126.4 (CH), 127.2 (CH), 139.8 (C), 146.4 (C), 151.8 (C), 157.8 (C=O), 168.0 (C=O); HRMS (ESI) calcd for $C_{15}H_{18}N_3O_4S$ (M+H) 336.1018, found 336.1031; UV (MeOH) λmax 237 nm (ε 1.69×10$^4$), 305 nm (ε 8.63×10$^3$); Anal. calcd for $C_{15}H_{17}N_3O_4S$: C, 53.71; H, 5.10; N, 12.53; found C, 53.49; H, 5.11; N, 12.45.

Example 29

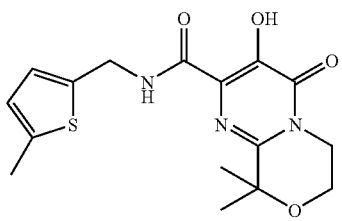

Pyrimido[2,1-c][1,4]oxazine-2-carboxamide, 4,6,7,9-tetrahydro-3-hydroxy-9,9-dimethyl-N-[(5-methyl-2-thienyl)methyl]-4-oxo-. $^1$H NMR (500 MHz, CDCl$_3$) δ ppm 1.57 (6H, s, gem-CH$_3$), 2.45 (3H, s, CH$_3$), 4.01 (4H, s, N, O—CH$_2$), 4.69 (2H, d, J=6.1 Hz, N—CH$_2$), 6.61 (1H, d, J=3.4 Hz, Th—H), 6.81 (1H, d, J=3.4 Hz, Th—H), 7.75 (1H, s, NH), 11.96 (1H, s, OH). $^{13}$C NMR (125.8 MHz, CDCl$_3$) δ ppm 15.5 (CH$_3$), 28.1 (CH$_3$), 38.3 (CH$_2$), 43.2 (7-CH$_2$), 58.2 (CH$_2$), 75.9 (C), 125.1 (CH), 125.4 (C), 126.4 (CH), 137.2 (C), 140.5 (C), 146.4 (C), 151.8 (C), 157.8 (C=O), 168.0 (C=O). HRMS (ESI) calcd for $C_{16}H_{20}N_3O_4S$ (M+H) 350.1175, found 350.1176 (δ +0.4 ppm); UV (MeOH) λmax 242 nm (ε 1.53×10$^4$), 305 (ε 7.54×10$^3$). Anal. calcd for $C_{16}H_{19}N_3O_4S$: C, 55.00; H, 5.48; N, 12.02; found C, 55.17; H, 5.60; N, 11.86.

Example 30

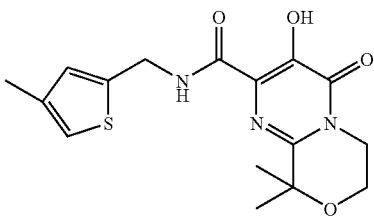

Pyrimido[2,1-c][1,4]oxazine-2-carboxamide, 4,6,7,9-tetrahydro-3-hydroxy-9,9-dimethyl-N-[(4-methyl-2-thienyl)methyl]-4-oxo-. Yield: 77%; white crystalline powder (95% EtOH) HPLC: 2.37 min (AP>98% at 254 nm) LC/MS m/z 350 (M+H) $^1$H NMR (500 MHz, CDCl$_3$) δ ppm 1.57 (6H, s, gem-CH$_3$), 2.23 (3H, s, CH$_3$), 4.01 (4H, s, N, O—CH$_2$), 4.71 (2H, d, J=6.1 Hz, N—CH$_2$), 6.82 (1H, s, Th—H), 6.85 (1H, s, Th—H), 7.78 (1H, brs, NH), 11.94 (1H, s, OH). $^{13}$C NMR (125.8 MHz, CDCl$_3$) δ ppm 15.8 (CH$_3$), 28.1 (CH$_3$), 38.2 (CH$_2$), 43.2 (CH$_2$), 58.2 (CH$_2$), 75.9 (C), 120.7 (CH), 125.4 (C), 128.8 (CH), 137.9 (C), 139.5 (C), 146.4 (C), 151.8 (C), 157.8 (C=O), 168.0 (C=O). HRMS (ESI) calcd for $C_{16}H_{20}N_3O_4S$ (M+H) 350.1175, found 350.1189. UV (MeOH) λmax 239 nm (ε 1.44×10$^4$), 305 (ε 7.69×10$^3$). Anal calcd for $C_{16}H_{19}N_3O_4S \cdot 0.3H_2O$: C, 54.16; H, 5.57; N, 11.84; found C, 54.15; H, 5.48; N, 11.83.

Example 31

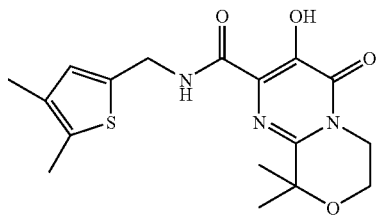

N-((4,5-dimethyl-2-thienyl)methyl)-3-hydroxy-9,9-dimethyl-4-oxo-4,6,7,9-tetrahydropyrimido[2,1-c][1,4]oxazine-2-carboxamide. Yield: 49% (white crystalline powder). HPLC: 2.76 min (AP>98% at 254 nm). LC/MS m/z 364 (M+H). $^1$H NMR (500 MHz, CDCl$_3$) δ ppm 1.57 (6H, s, gem-CH$_3$), 2.08 (3H, s, Th—CH$_3$), 2.30 (3H, s, Th—CH$_3$), 4.00 (4H, s, N, O—CH$_2$), 4.64 (2H, d, J=5.8 Hz, N—CH$_2$), 6.71 (1H, s, Th—H), 7.73 (1H, brs, NH), 11.97 (1H, s, OH). $^{13}$C NMR (125.8 MHz, CDCl$_3$) δ ppm 13.2 (CH$_3$), 13.6 (CH$_3$), 28.1 (CH$_3$), 38.2 (CH$_2$), 43.2 (CH$_2$), 58.2 (CH$_2$), 75.9 (C), 125.5 (C), 129.5 (CH), 133.1, 133.2 (C), 134.5 (C), 146.4 (C), 151.8 (C), 157.8 (C=O), 168.0 (C=O). HRMS (ESI) calcd for C$_{17}$H$_{22}$N$_3$O$_4$S (M+H) 364.1331, found 364. UV (MeOH) λmax 240 nm (ε 1.45×10$^4$), 306 (ε 7.64×10$^3$). Anal. calcd for C$_{17}$H$_{21}$N$_3$O$_4$S.0.2H$_2$O: C, 55.63; H, 5.88; N, 11.45; found C, 55.51; H, 5.88; N, 11.42.

Example 32

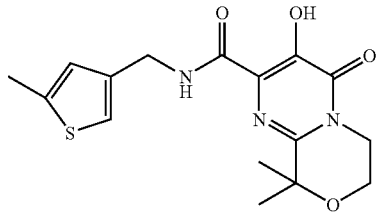

Pyrimido[2,1-c][1,4]oxazine-2-carboxamide, 4,6,7,9-tetrahydro-3-hydroxy-9,9-dimethyl-N-[(5-methyl-3-thienyl)methyl]-4-oxo-. HPLC: 2.40 min (AP 99% at 254 nm). LC/MS m/z 350 (M+H). $^1$H NMR (500 MHz, CDCl$_3$) δ ppm 1.57 (6H, s, gem-CH$_3$), 2.46 (3H, s, Th—CH$_3$), 4.01 (4H, s, N, O—CH$_2$), 4.52 (2H, d, J=6.1 Hz, N—CH$_2$), 6.72 (1H, s, Th—H), 6.93 (1H, s, Th—H), 7.73 (1H, brs, NH), 12.05 (1H, s, OH). $^{13}$C NMR (125.8 MHz, CDCl$_3$) δ ppm 15.4 (CH$_3$), 28.1 (CH$_3$), 38.6 (CH$_2$), 43.2 (CH$_2$), 58.2 (CH$_2$), 75.8 (C), 120.2 (CH), 125.4 (CH), 125.5 (C), 137.8 (C), 141.5 (C), 146.4 (C), 151.8 (C), 157.9 (C=O), 168.1 (C=O). UV (MeOH) λmax 239 nm (ε 1.26×10$^4$), 305 (ε 6.2×10$^3$). Anal. calcd for C$_{16}$H$_{19}$N$_3$O$_4$S: C, 55.00; H, 5.48; N, 12.02; found C, 55.06; H, 5.52; N, 11.92.

Example 33

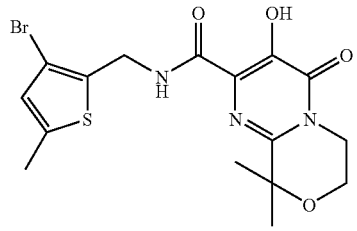

Pyrimido[2,1-c][1,4]oxazine-2-carboxamide, N-[(3-bromo-5-methyl-2-thienyl)methyl]-4,6,7,9-tetrahydro-3-hydroxy-9,9-dimethyl-4-oxo-. A solution of 3-(benzyloxy)-N-((3-bromo-5-methylthiophen-2-yl)methyl)-9,9-dimethyl-4-oxo-4,6,7,9-tetrahydropyrimido[2,1-c][1,4]oxazine-2-carboxamide (44 mg, 0.085 mmol) in TFA (1 mL) was left at room temperature overnight (~18 h). TFA was removed in vacuo and the residue triturated with diethyl ether to obtain 27 mg of a light brown powder which was crystallized from CH$_2$Cl$_2$-95% EtOH to obtain 17 mg (0.040 mmol, Y. 47%) of the title compound as a beige crystalline powder: HPLC: 2.72 min (AP 91% at 254 nm); LC/MS m/z 428/430 (M+H); $^1$H NMR (500 MHz, CDCl$_3$) δ ppm 1.58 (6H, s, gem-CH$_3$), 2.42 (3H, s, Th—CH$_3$), 4.00 (4H, s, N, O—CH$_2$), 4.64 (2H, d, J=6 Hz, CH$_2$), 6.62 (1H, s, Th—H), 7.92 (1H, s, NH), 11.81 (1H, s, OH); $^{13}$C NMR (125.8 MHz, CDCl$_3$) δ ppm 15.5 (CH$_3$), 28.1 (CH$_3$), 37.0 (CH$_2$), 43.2 (CH$_2$), 58.2 (CH$_2$), 75.9 (C), 109.9 (C), 125.4 (C), 128.1 (CH), 131.3 (C), 140.2 (C), 146.3 (C), 151.8 (C), 157.8 (C=O), 168.0 (C=O); HRMS (ESI) calcd for C$_{16}$H$_{20}$N$_3$O$_4$SBr (M+H) 428.0280, found 428.0277.

Example 34

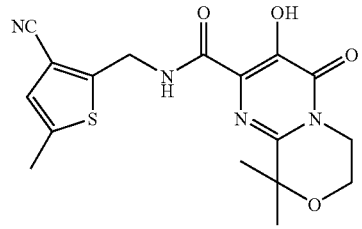

Pyrimido[2,1-c][1,4]oxazine-2-carboxamide, N-[(3-cyano-5-methyl-2-thienyl)methyl]-4,6,7,9-tetrahydro-3-hydroxy-9,9-dimethyl-4-oxo-. A mixture of 3-(benzyloxy)-N-((3-bromo-5-methylthiophen-2-yl)methyl)-9,9-dimethyl-4-oxo-4,6,7,9-tetrahydropyrimido[2,1-c][1,4]oxazine-2-carboxamide (52 mg, 0.10 mmol) and CuCN (9 mg, 0.10 mmol) in N-methyl-2-pyrrolidone (1 mL) was stirred in an oil bath heated at 120° C. under a nitrogen atmosphere for 8 h. HPLC indicated the reaction was incomplete. To this more of CuCN (10 mg) was added and the mixture heated at 150° C. for another 6 h. The solvent was removed in vacuo and the residue diluted with EtOAc (10 mL) was mixed with 14% aq. NH$_4$OH (5 mL) and stirred at room temperature for 30 min. The aqueous phase was acidified with 6N HCl and extracted with CH$_2$Cl$_2$ (15 mL×2). The combined extracts were washed with brine, dried (Na$_2$SO$_4$), filtered and concentrated to give a brown oily solid which was triturated with 95% EtOH to obtain 21 mg (0.056 mmol, Y. 56%) of the title compound as a beige crystalline powder: HPLC: 2.29 min (AP 95% at 254 nm); LC/MS m/z 375 (M+H); $^1$H NMR (500 MHz, CDCl$_3$) δ ppm 1.60 (6H, s, gem-CH$_3$), 2.44 (3H, s, Th—CH$_3$), 4.01 (4H, s, N, O—CH$_2$), 4.82 (2H, d, J=6.4 Hz, CH$_2$), 6.81 (1H, s, Th—H), 8.07 (1H, t, J=6.1 Hz, NH), 11.64 (1H, s, OH); $^{13}$C NMR (125.8 MHz, CDCl$_3$) δ ppm 15.3 (CH$_3$), 28.0 (CH$_3$), 36.7 (CH$_2$), 43.2 (CH$_2$), 58.2 (CH$_2$), 75.9 (C), 108.9 (C), 114.7 (C), 125.1 (C), 125.9 (CH), 141.5 (C), 146.5 (C), 148.9 (C), 152.2 (C), 157.7 (C=O), 168.4 (C=O); HRMS (ESI)

calcd for $C_{17}H_{19}N_4O_4S$ (M+H) 375.1124, found 375.1143; UV (MeOH) λmax 232 nm (ε 12.55×10⁴), 305 (ε 9.34×10³).

Example 35

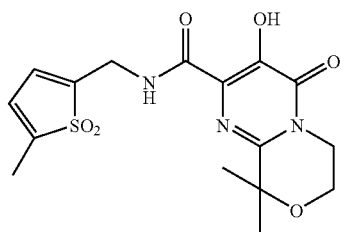

Pyrimido[2,1-c][1,4]oxazine-2-carboxamide, 4,6,7,9-tetrahydro-3-hydroxy-9,9-dimethyl-N-[(5-methyl-1,1-dioxido-2-thienyl)methyl]-4-oxo-. Yield: 43%; off-white powder. HPLC: 1.71 min (AP 96% at 254 nm). LC/MS m/z 382 (M+H). ¹H NMR (500 MHz, CDCl₃) δ ppm 1.60 (6H, s, gem-CH₃), 2.13 (3H, s, Th—CH₃), 4.01 (4H, s, N, O—CH₂), 4.50 (2H, d, J=5.8 Hz, N—CH₂), 6.36 (1H, dd, J=4.0, 1.8 Hz, Th—H), 6.64 (1H, d, J=4.0 Hz, Th—H), 8.09 (1H, t, J=4.6 Hz, NH), 11.58 (1H, s, OH). ¹³C NMR (125.8 MHz, CDCl₃) δ ppm 9.50 (CH₃), 28.0 (CH₃), 33.9 (CH₂), 43.2 (CH₂), 58.2 (CH₂), 76.0 (C), 122.2 (CH), 125.3 (C), 126.2 (CH), 137.7 (C), 141.4 (C), 146.2 (C), 152.1 (C), 157.8 (C=O), 168.4 (C=O)HRMS (ESI) calcd for $C_{16}H_{20}N_3O_6S$ (M+H) 382.1073, found 382.1081.

Additional formula I compounds are tabulated in the table below.

| Example | Structure | HPLC RT (min) | Mass spec |
|---|---|---|---|
| 36 | Pyrimido[2,1-c][1,4]oxazine-2-carboxamide, 4,6,7,9-tetrahydro-3-hydroxy-9,9-dimethyl-4-oxo-N-(3-thienylmethyl)- | 2.81 | 336.13 |
| 37 | Pyrimido[2,1-c][1,4]oxazine-2-carboxamide, 4,6,7,9-tetrahydro-3-hydroxy-9,9-dimethyl-N-[(5-methyl-2-furanyl)methyl]-4-oxo- | 2.9 | 334.17 |
| 38 | Pyrimido[2,1-c][1,4]oxazine-2-carboxamide, N-(2-furanylmethyl)-4,6,7,9-tetrahydro-3-hydroxy-9,9-dimethyl-4-oxo- | 2.52 | 320.15 |

-continued

| Example | Structure | HPLC RT (min) | Mass spec |
|---|---|---|---|
| 39 | 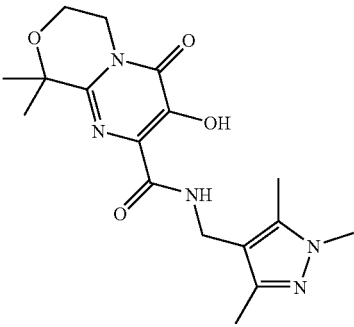<br>Pyrimido[2,1-c][1,4]oxazine-2-carboxamide, 4,6,7,9-tetrahydro-3-hydroxy-9,9-dimethyl-4-oxo-N-[(1,3,5-trimethyl-1H-pyrazol-4-yl)methyl]- | 1.82 | 362.21 |
| 40 | 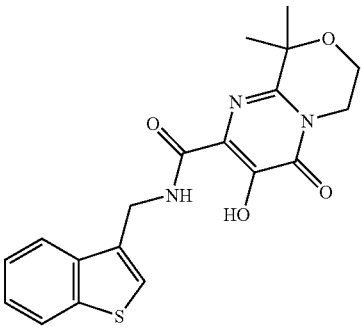<br>Pyrimido[2,1-c][1,4]oxazine-2-carboxamide, N-(benzo[b]thien-3-ylmethyl)-4,6,7,9-tetrahydro-3-hydroxy-9,9-dimethyl-4-oxo- | 1.32 | 402.16 |
| 41 | 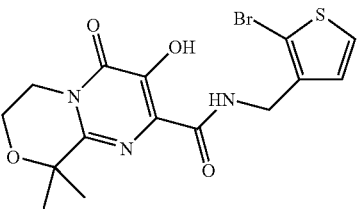<br>Pyrimido[2,1-c][1,4]oxazine-2-carboxamide, N-[(2-bromo-3-thienyl)methy]-4,6,7,9-tetrahydro-3-hydroxy-9,9-dimethyl-4-oxo- | 1.25 | 411.25 |
| 42 | 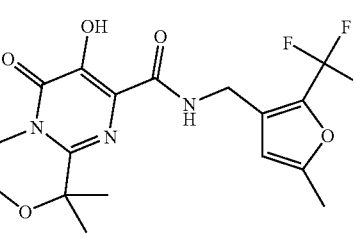<br>Pyrimido[2,1-c][1,4]oxazine-2-carboxamide, 4,6,7,9-tetrahydro-3-hydroxy-9,9-dimethyl-N-[[5-methyl-2-(trifluoromethyl)-3-furanyl]methy]-4-oxo- | 1.33 | 348.2 |

-continued

| Example | Structure | HPLC RT (min) | Mass spec |
|---|---|---|---|
| 43 | 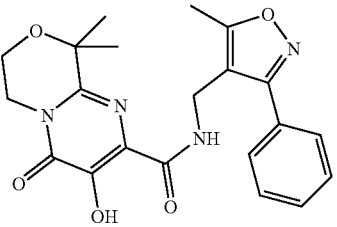<br>Pyrimido[2,1-c][1,4]oxazine-2-carboxamide, 4,6,7,9-tetrahydro-3-hydroxy-9,9-dimethyl-N-[(5-methyl-3-phenyl-4-isoxazolyl)methy]-4-oxo- | 1.33 | 431.18 |
| 44 | 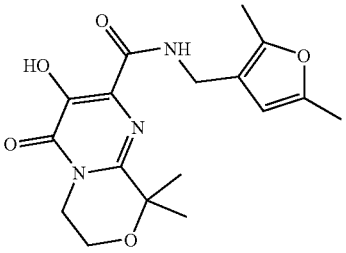<br>Pyrimido[2,1-c][1,4]oxazine-2-carboxamide, N-[(2,5-dimethyl-3-furanyl)methyl]-4,6,7,9-tetrahydro-3-hydroxy-9,9-dimethyl-4-oxo- | 1.01 | 362.26 |
| 45 | 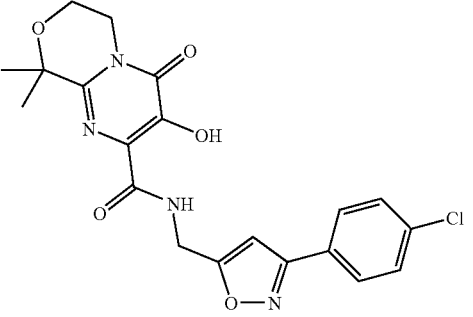<br>Pyrimido[2,1-c][1,4]oxazine-2-carboxamide, N-[[3-(4-chlorophenyl)-5-isoxazolyl]methyl]-4,6,7,9-tetrahydro-3-hydroxy-9,9-dimethyl-4-oxo- | 1.09 | 333.22 |
| 46 | 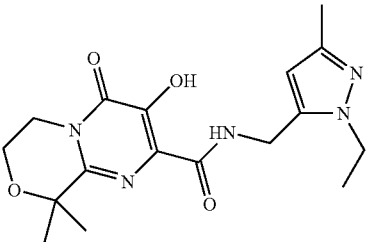<br>Pyrimido[2,1-c][1,4]oxazine-2-carboxamide, N-[(1-ethyl-3-methyl-1H-pyrazol-5-yl)methyl]-4,6,7,9-tetrahydro-3-hydroxy-9,9-dimethyl-4-oxo- | 1.18 | 427.24 |

-continued
| Example | Structure | HPLC RT (min) | Mass spec |
|---|---|---|---|
| 47 | 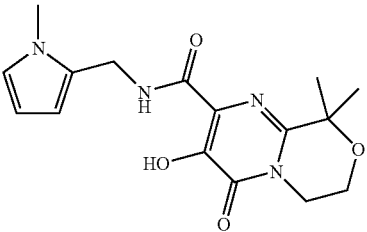 Pyrimido[2,1-c][1,4]oxazine-2-carboxamide, 4,6,7,9-tetrahydro-3-hydroxy-9,9-dimethyl-N-[(1-methyl-1H-pyrrol-2-yl)methyl]-4-oxo | 1.39 | 411.29 |
| 48 | 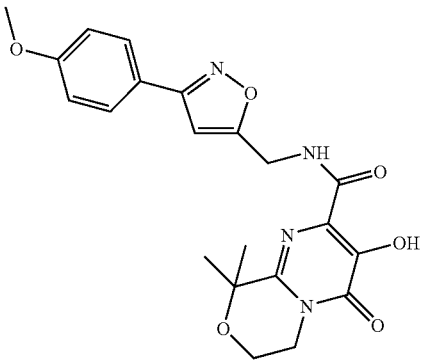 Pyrimido[2,1-c][1,4]oxazine-2-carboxamide, 4,6,7,9-tetrahydro-3-hydroxy-N-[[3-(4-methoxyphenyl)-5-isoxazolyl]methyl]-9,9-dimethyl-4-oxo- | 1.13 | 438.16 |
| 49 | 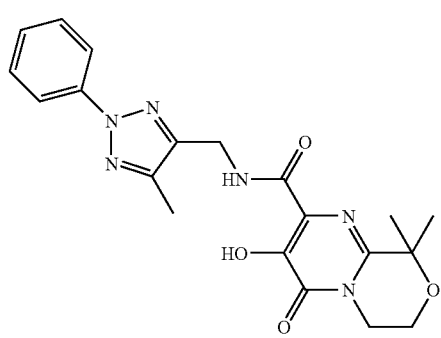 Pyrimido[2,1-c][1,4]oxazine-2-carboxamide, 4,6,7,9-tetrahydro-3-hydroxy-9,9-dimethyl-N-[(5-methyl-2-phenyl-2H-1,2,3-triazol-4-yl)methy]-4-oxo- | 1.05 | 399.27 |

-continued

| Example | Structure | HPLC RT (min) | Mass spec |
|---|---|---|---|
| 50 | 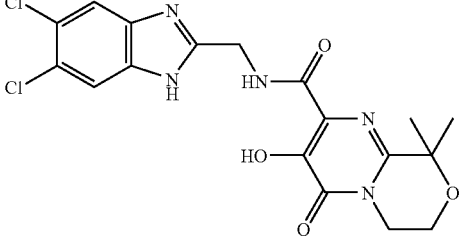 Pyrimido[2,1-c][1,4]oxazine-2-carboxamide, N-[(5,6-dichloro-1H-benzimidazol-2-yl)methyl]-4,6,7,9-tetrahydro-3-hydroxy-9,9-dimethyl-4-oxo- | 1.25 | 427.29 |
| 51 | 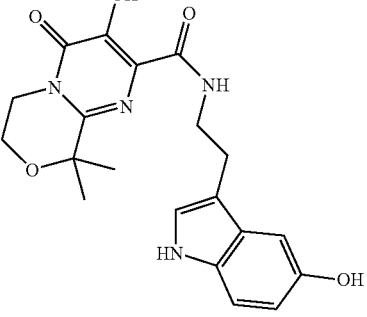 Pyrimido[2,1-c][1,4]oxazine-2-carboxamide, 4,6,7,9-tetrahydro-3-hydroxy-N-[2-(5-hydroxy-1H-indol-3-yl)ethyl]-9,9-dimethyl-4-oxo- | 1.23 | 350.19 |
| 52 | 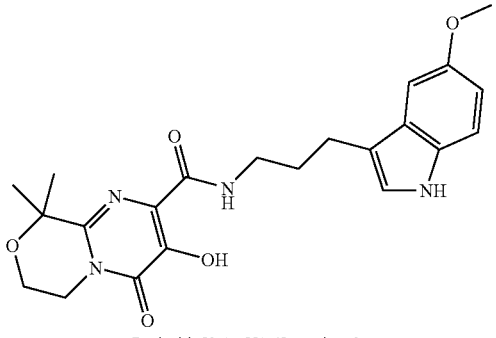 Pyrimido[2,1-c][1,4]oxazine-2-carboxamide, 4,6,7,9-tetrahydro-3-hydroxy-N-[3-(5-methoxy-1H-indol-3-yl)propyl]-9,9-dimethyl-4-oxo- | 1.19 | 369.13 |
| 53 | 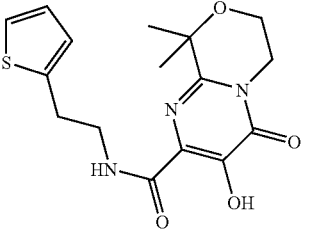 Pyrimido[2,1-c][1,4]oxazine-2-carboxamide, 4,6,7,9-tetrahydro-3-hydroxy-9,9-dimethyl-4-oxo-N-[2-(2-thienyl)ethyl]- | 0.75 | 394.14 |

-continued

| Example | Structure | HPLC RT (min) | Mass spec |
|---------|-----------|---------------|-----------|
| 54 | 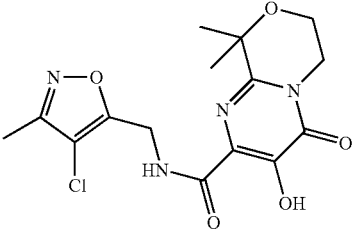 Pyrimido[2,1-c][1,4]oxazine-2-carboxamide, N-[(4-chloro-3-methyl-5-isoxazolyl)methyl]-4,6,7,9-tetrahydro-3-hydroxy-9,9-dimethyl-4-oxo- | 1.32 | 370.16 |
| 55 | 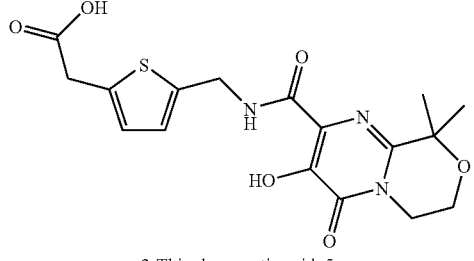 2-Thiopheneacetic acid, 5-[[[(4,6,7,9-tetrahydro-3-hydroxy-9,9-dimethyl-4-oxopyrimido[2,1-c][1,4]oxazin-2-yl)carbonyl]amino]methy]- | 1.26 | 383.19 |
| 56 | 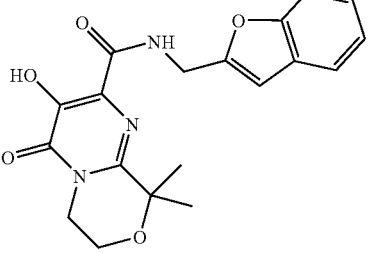 Pyrimido[2,1-c][1,4]oxazine-2-carboxamide, N-(2-benzofuranylmethyl)-4,6,7,9-tetrahydro-3-hydroxy-9,9-dimethyl-4-oxo- | 1.32 | 397.19 |
| 57 | 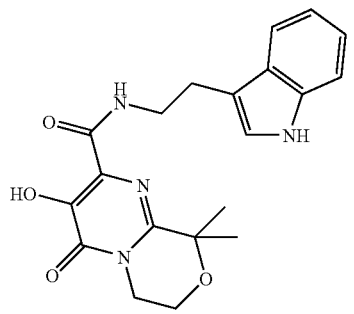 Pyrimido[2,1-c][1,4]oxazine-2-carboxamide, 4,6,7,9-tetrahydro-3-hydroxy-N-[2-(1H-indol-3-yl)ethyl]-9,9-dimethyl-4-oxo- | 0.26 | 371.16 |

-continued
| Example | Structure | HPLC RT (min) | Mass spec |
|---|---|---|---|
| 58 | 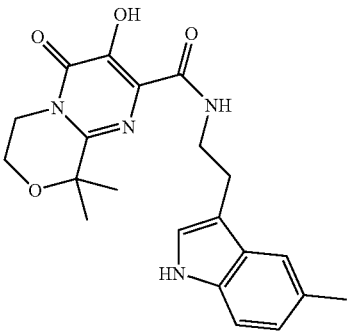<br>Pyrimido[2,1-c][1,4]oxazine-2-carboxamide, 4,6,7,9-tetrahydro-3-hydroxy-9,9-dimethyl-N-[2-(5-methyl-1H-indol-3-yl)ethyl]-4-oxo- | 0.87 | 446.15 |
| 59 | 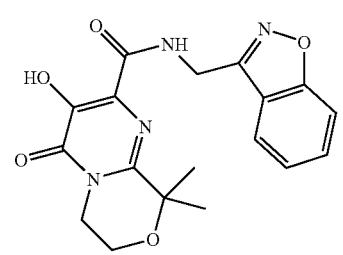<br>Pyrimido[2,1-c][1,4]oxazine-2-carboxamide, N-(1,2-benzisoxazol-3-ylmethyl)-4,6,7,9-tetrahydro-3-hydroxy-9,9-dimethyl-4-oxo- | 0.19 | 348.19 |
| 60 | 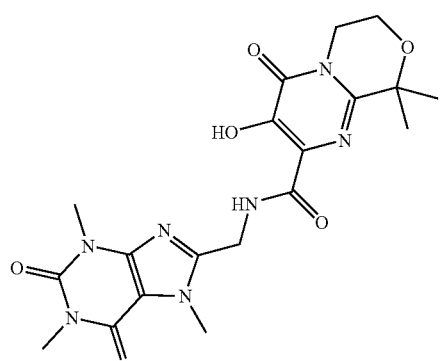<br>Pyrimido[2,1-c][1,4]oxazine-2-carboxamide, 4,6,7,9-tetrahydro-3-hydroxy-9,9-dimethyl-4-oxo-N-[(2,3,6,7-tetrahydro-1,3,7-trimethyl-2,6-dioxo-1H-purin-8-yl)methyl]- | 1.36 | 403.16 |

-continued
| Example | Structure | HPLC RT (min) | Mass spec |
|---|---|---|---|
| 61 | 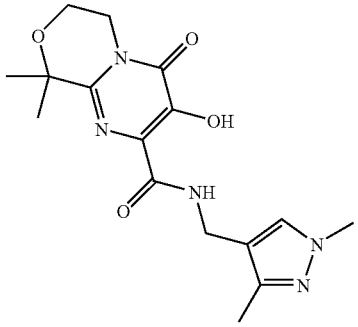 Pyrimido[2,1-c][1,4]oxazine-2-carboxamide, N-[(1,3-dimethyl-1H-pyrazol-4-yl)methyl]-4,6,7,9-tetrahydro-3-hydroxy-9,9-dimethyl-4-oxo- | 0.98 | 362.14 |
| 62 | 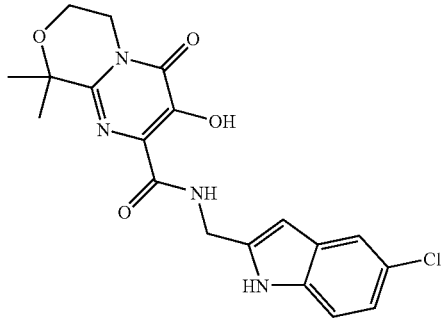 Pyrimido[2,1-c][1,4]oxazine-2-carboxamide, N-[(5-chloro-1H-indol-2-yl)methyl]-4,6,7,9-tetrahydro-3-hydroxy-9,9-dimethyl-4-oxo- | 1 | 362.19 |
| 63 | 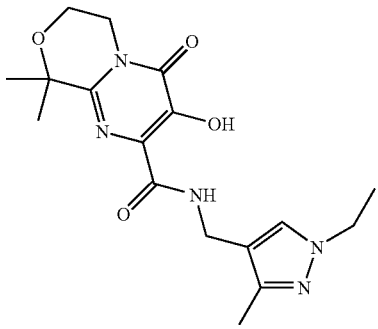 Pyrimido[2,1-c][1,4]oxazine-2-carboxamide, N-[(1-ethyl-3-methyl-1H-pyrazol-4-yl)methyl]-4,6,7,9-tetrahydro-3-hydroxy-9,9-dimethyl-4-oxo- | 0.94 | 348.17 |

-continued
| Example | Structure | HPLC RT (min) | Mass spec |
|---|---|---|---|
| 64 | 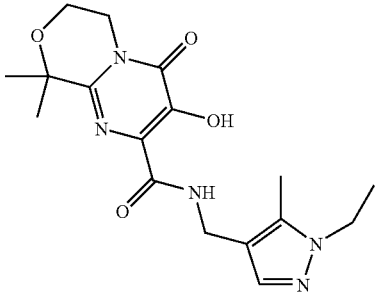 Pyrimido[2,1-c][1,4]oxazine-2-carboxamide, N-[(1-ethyl-5-methyl-1H-pyrazol-4-yl)methyl]-4,6,7,9-tetrahydro-3-hydroxy-9,9-dimethyl-4-oxo- | 1.55 | 472.22 |
| 65 | 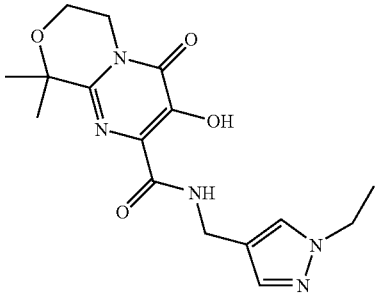 Pyrimido[2,1-c][1,4]oxazine-2-carboxamide, N-[(1-ethyl-1H-pyrazol-4-yl)methyl]-4,6,7,9-tetrahydro-3-hydroxy-9,9-dimethyl-4-oxo- | 0.96 | 348.12 |
| 66 | 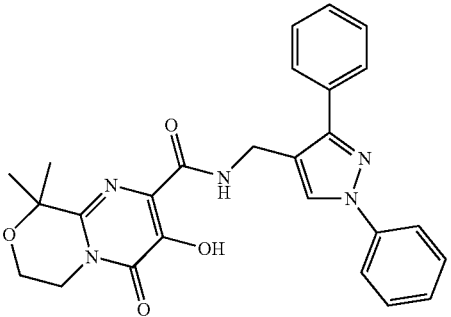 Pyrimido[2,1-c][1,4]oxazine-2-carboxamide, N-[(1,3-diphenyl-1H-pyrazol-4-yl)methyl]-4,6,7,9-tetrahydro-3-hydroxy-9,9-dimethyl-4-oxo- | 0.92 | 348.17 |

-continued

| Example | Structure | HPLC RT (min) | Mass spec |
|---|---|---|---|
| 67 | 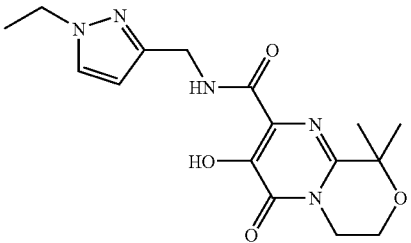<br>Pyrimido[2,1-c][1,4]oxazine-2-carboxamide, N-[(1-ethyl-1H-pyrazol-3-yl)methyl]-4,6,7,9-tetrahydro-3-hydroxy-9,9-dimethyl-4-oxo- | 0.77 | 320.15 |
| 68 | 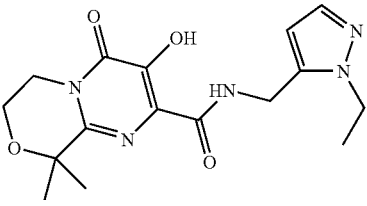<br>Pyrimido[2,1-c][1,4]oxazine-2-carboxamide, N-[(1-ethyl-1H-pyrazol-5-yl)methyl]-4,6,7,9-tetrahydro-3-hydroxy-9,9-dimethyl-4-oxo- | 1.15 | 382.07 |
| 69 | 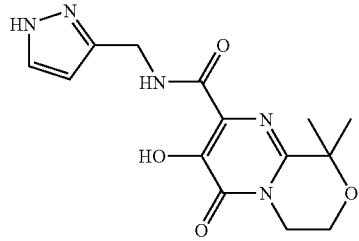<br>Pyrimido[2,1-c][1,4]oxazine-2-carboxamide, 4,6,7,9-tetrahydro-3-hydroxy-9,9-dimethyl-4-oxo-N-(1H-pyrazol-3-ylmethyl)- | 1.11 | 382.12 |
| 70 | 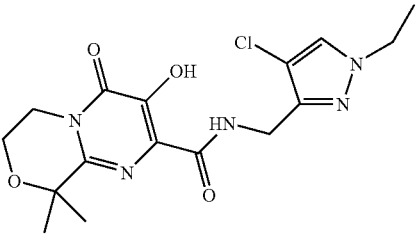<br>Pyrimido[2,1-c][1,4]oxazine-2-carboxamide, N-[(4-chloro-1-ethyl-1H-pyrazol-3-yl)methyl]-4,6,7,9-tetrahydro-3-hydroxy-9,9-dimethyl-4-oxo- | 0.85 | 334.13 |

-continued

| Example | Structure | HPLC RT (min) | Mass spec |
|---|---|---|---|
| 71 | 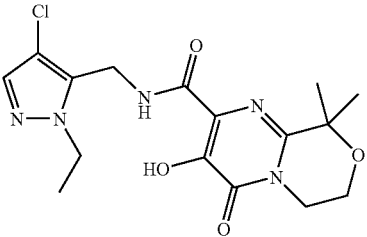 Pyrimido[2,1-c][1,4]oxazine-2-carboxamide, N-[(4-chloro-1-ethyl-1H-pyrazol-5-yl)methyl]-4,6,7,9-tetrahydro-3-hydroxy-9,9-dimethyl-4-oxo- | 1.13 | 426.13 |
| 72 | 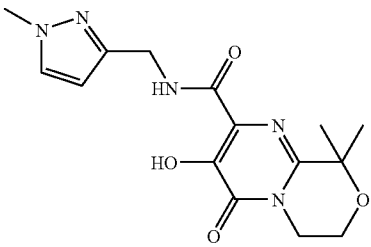 Pyrimido[2,1-c][1,4]oxazine-2-carboxamide, 4,6,7,9-tetrahydro-3-hydroxy-9,9-dimethyl-N-[(1-methyl-1H-pyrazol-3-yl)methyl]-4-oxo- | 1.34 | 427.15 |
| 73 | 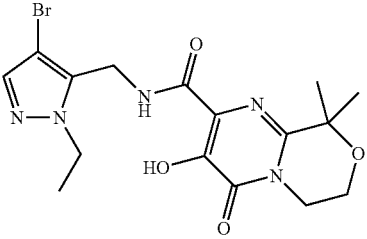 Pyrimido[2,1-c][1,4]oxazine-2-carboxamide, N-[(4-bromo-1-ethyl-1H-pyrazol-5-yl)methyl]-4,6,7,9-tetrahydro-3-hydroxy-9,9-dimethyl-4-oxo- | 0.58 | 364.15 |
| 74 | 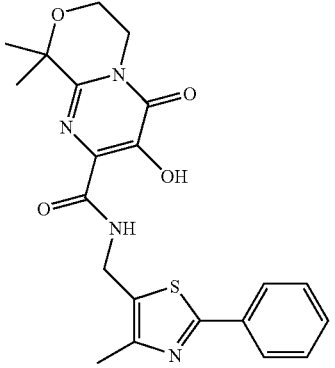 Pyrimido[2,1-c][1,4]oxazine-2-carboxamide, 4,6,7,9-tetrahydro-3-hydroxy-9,9-dimethyl-N-[(4-methyl-2-phenyl-5-thiazolyl)methyl]-4-oxo- | 8.05 | 336.13 |

| Example | Structure | HPLC RT (min) | Mass spec |
|---|---|---|---|
| 75 | 3-Furancarboxylic acid, 5-[[[(4,6,7,9-tetrahydro-3-hydroxy-9,9-dimethyl-4-oxopyrimido[2,1-c][1,4]oxazin-2-yl)carbonyl]amino]methyl] | 9.48 | 386.15 |

Example 76

N-(2,3-dihydro-1-benzofuran-2-ylmethyl)-3-hydroxy-9,9-dimethyl-4-oxo-4,6,7,9-tetrahydropyrimido[2,1-c][1,4]oxazine-2-carboxamide. $^1$H NMR (500 MHz, DMSO-D$_6$) δ ppm 1.54 (s, 3H), 1.56 (s, 3H), 3.01 (dd, J=15.87, 6.41 Hz, 1H), 3.27-3.34 (m, 2H), 3.48-3.55 (m, 1H), 3.57-3.65 (m, 1H), 3.83 (t, J=5.04 Hz, 2 H), 3.97 (t, J=5.04 Hz, 2H), 5.01 (dd, J=9.31, 5.34 Hz, 1H), 6.75-6.84 (m, 2H), 7.08 (t, J=7.32 Hz, 1H), 7.22 (d, J=7.32 Hz, 1H), 9.00 (t, J=6.10 Hz, 1H), 12.18 (s, 1H). $^{13}$C NMR (125 MHz, DMSO-D$_6$) δ ppm, 27.49, 32.20, 42.73, 42.79, 57.35, 75.29, 80.22, 109.00, 120.31, 125.09, 126.28, 127.78, 145.32, 151.64, 156.95, 158.68, 168.58. Anal. Calcd for C$_{19}$H$_{21}$N$_3$O$_5$: C, 61.44; H, 5.69; N, 11.31. Found: C, 61.41; H, 5.66; N, 11.23.

Example 77

3'-Hydroxy-8'-methyl-N-((5-methyl-2-furyl)methyl)-4'-oxo-7',8'-dihydro-4'H,6'H-spiro[cyclobutane-1,9'-pyrazino[1,2-a]pyrimidine]-2'-carboxamide. $^1$H NMR (500 MHz, DMSO-D$_6$) δ ppm 1.85 (dd, J=14.04, 3.66 Hz, 2H), 2.04-2.14 (m, 2H), 2.24 (s, 3H), 2.50 (m, 3H), 2.74 (s, 4H), 3.53 (t, J=5.95 Hz, 1H), 4.01 (t, J=5.80 Hz, 1H), 4.47 (d, J=6.10 Hz, 3H), 6.01 (d, J=1.83 Hz, 1H), 6.18 (d, J=3.05 Hz, 1H), 9.21 (t, J=6.10 Hz, 1H), 12.61 (s, 1H).

Example 78

3-Hydroxy-9,9-dimethyl-N-((1-(methylsulfonyl)-1H-indazol-3-yl)methyl)-4-oxo-4,6,7,9-tetrahydropyrimido[2,1-c][1,4]oxazine-2-carboxamide. $^1$H NMR (500 MHz, DMSO-D$_6$) δ ppm 1.57 (s, 6H), 3.42 (s, 3H), 3.83 (t, J=5.04 Hz, 2H), 3.97 (t, J=5.19 Hz, 2H), 4.91 (d, J=6.10 Hz, 2H), 7.43 (t, J=7.63 Hz, 1H), 7.65 (t, J=7.78 Hz, 1H), 7.96 (d, J=8.55 Hz, 1H), 8.02 (d, J=7.93 Hz, 1H), 9.64 (s, 1H), 12.00 (s, 1 H). $^{13}$C NMR (125 MHz, DMSO-D$_6$) δ ppm 27.50, 35.80, 40.55, 42.73, 57.35, 75.35, 112.68, 121.30, 123.66, 124.06, 125.22, 129.52, 140.65, 149.77, 157.01, 168.44.

Example 79

Methyl 3-((((3-hydroxy-9,9-dimethyl-4-oxo-4,6,7,9-tetrahydropyrimido[2,1-c][1,4]oxazin-2-yl)carbonyl)amino)

methyl)-1H-indazole-1-carboxylate. $^1$H NMR (500 MHz, DMSO-D$_6$) δ ppm 1.57 (s, 6H), 3.83 (t, J=5.04 Hz, 2H), 3.94-4.00 (m, 2H), 4.04 (s, 3H), 4.88 (d, J=6.41 Hz, 2H), 7.41 (t, J=7.63 Hz, 1H), 7.64 (t, J=7.78 Hz, 1H), 8.00 (d, J=7.93 Hz, 1H), 8.14 (d, J=8.24 Hz, 1H), 9.61 (t, J=6.26 Hz, 1H), 12.03 (br s, 1H). $^{13}$C NMR (125 MHz, DMSO-D$_6$) δ ppm 27.48, 35.69, 40.12, 42.74, 54.28, 57.35, 75.35, 114.00, 121.05, 123.90, 125.23, 129.45, 140.02, 145.35, 148.74, 150.48, 151.79, 156.95, 168.39.

Example 80

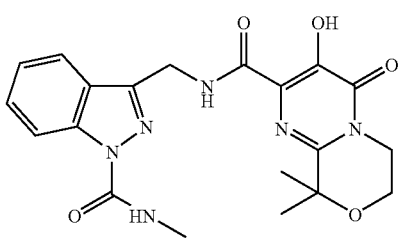

3-Hydroxy-9,9-dimethyl-N-((1-(methylcarbamoyl)-1H-indazol-3-yl)methyl)-4-oxo-4,6,7,9-tetrahydropyrimido[2,1-c][1,4]oxazine-2-carboxamide. $^1$H NMR (500 MHz, DMSO-D$_6$) δ ppm 1.57 (s, 6H), 2.86 (d, J=4.58 Hz, 3H), 3.83 (t, J=5.04 Hz, 2 H), 3.97 (t, J=5.19 Hz, 2H), 4.90 (d, J=6.41 Hz, 2H), 7.29 (t, J=7.48 Hz, 1 H), 7.55 (t, J=7.78 Hz, 1H), 7.93 (d, J=8.24 Hz, 1H), 8.16 (d, J=4.58 Hz, 1H), 8.27 (d, J=8.54 Hz, 1H), 9.59 (s, 1H), 12.03 (s, 1H).

Example 81

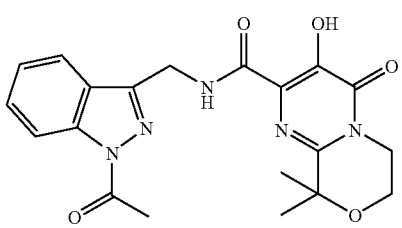

N-((1-Acetyl-1H-indazol-3-yl)methyl)-3-hydroxy-9,9-dimethyl-4-oxo-4,6,7,9-tetrahydropyrimido[2,1-c][1,4]oxazine-2-carboxamide.

Example 82

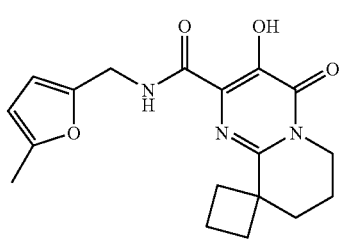

3'-Hydroxy-N-((5-methyl-2-furyl)methyl)-4'-oxo-7',8'-dihydro-4'H,6'H-spiro[cyclobutane-1,9'-pyrido[1,2-a]pyrimidine]-2'-carboxamide. Yield: 43%. $^1$H NMR (500 MHz, CDCl$_3$) δ: 11.81 (1H, s), 7.96 (1H, br t), 6.19 (1H, d, J=3.1 Hz), 5.93 (1H, d, J=3.1 Hz), 4.58 (2H, d, J=5.8 Hz), 3.95 (2H, t, J=6.4 Hz), 2.66-2.60 (2H, m), 2.28 (3H, s), 2.10-1.90 (8H, m). HRMS (M+H) calcd for C$_{18}$H$_{22}$N$_3$O$_4$: 344.1610; found: 344.1598. Anal calcd for C$_{18}$H$_{21}$N$_3$O$_4$: C, 62.96; H, 6.16; N, 12.23; found: C, 62.85; H, 5.98; N, 12.15.

Example 83

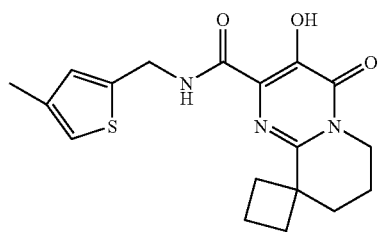

3'-Hydroxy-N-((4-methyl-2-thienyl)methyl)-4'-oxo-7',8'-dihydro-4'H,6'H-spiro[cyclobutane-1,9'-pyrido[1,2-a]pyrimidine]-2'-carboxamide. Yield: 74%. $^1$H NMR (500 MHz, CDCl$_3$) δ: 11.79 (1H, s), 8.01 (1H, t, J=4.6 Hz), 6.87 (1H, s), 6.83 (1H, s), 4.76 (2H, d, J=6.1 Hz), 3.96 (2H, t, J=6.4 Hz), 2.64-2.58 (2H, m), 2.24 (3H, s), 2.09-1.90 (8H, m). HRMS (M+H) calcd for C$_{18}$H$_{22}$N$_3$O$_3$S: 360.1382; found: 360.1393. Anal calcd for C$_{18}$H$_{21}$N$_3$O$_3$S: C, 60.14; H, 5.88; N, 11.69; found: C, 59.94; H, 5.85; N, 11.48.

Example 84

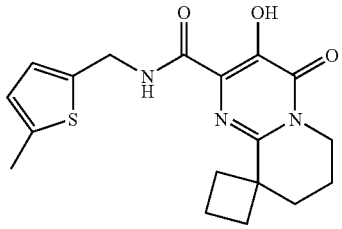

3'Hhydroxy-N-((5-methyl-2-thienyl)methyl)-4'-oxo-7',8'-dihydro-4'H,6'H-spiro[cyclobutane-1,9'-pyrido[1,2-a]pyrimidine]-2'-carboxamide. Yield: 52%. $^1$H NMR (500 MHz, CDCl$_3$) δ: 11.81 (1H, s), 7.98 (1H, br t), 6.84 (1H, d, J=3.4 Hz), 6.62 (1H, d, J=3.4 Hz), 4.73 (2H, d, J=6.1 Hz), 3.95 (2H, t, J=6.4 Hz), 2.64-2.58 (2H, m), 2.46 (3H, s), 2.08-1.90 (8H, m). HRMS (M+H) calcd for C$_{18}$H$_{22}$N$_3$O$_3$S: 360.1382; found:

360.1377. Anal calcd for $C_{18}H_{21}N_3O_3S$: C, 60.14; H, 5.88; N, 11.69; found: C, 59.96; H, 5.73; N, 11.55.

Example 85

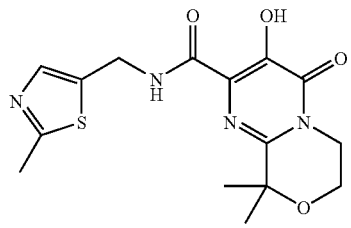

3-Hydroxy-9,9-dimethyl-N-((2-methylthiazol-5-yl)methyl)-4-oxo-4,6,7,9-tetrahydropyrimido[2,1-c][1,4]oxazine-2-carboxamide. A solution of 3-(benzyloxy)-9,9-dimethyl-N-((2-methylthiazol-5-yl)methyl)-4-oxo-4,6,7,9-tetrahydropyrimido[2,1-c][1,4]oxazine-2-carboxamide (0.210 g, 0.477 mmol) in a mixture of ethyl acetate (200 ml) and ethanol (50 ml) at 25° C. was hydrogenated over 10% palladium on activated carbon (0.25 g) and under one atmosphere of hydrogen for two hours to give 0.154 g (92% yield) of the title compound as white crystals; mp 245° C. (ethanol). 1HNMR 400 MHz (CDCl$_3$) δ (ppm): 1.60 (6H, s, 2×CH$_3$), 2.71 (3H, s, CH$_3$), 4.04 (4H, s, 2×CH$_2$), 4.76 (2H, d, J=6.1 Hz, NCH$_2$), 7.57 (1H, s, CH), 7.82 (1H, broad t, NH), 11.83 (1H, s, OH). Anal. Calcd for $C_{15}H_{18}N_4O_4S$: C 51.41; H, 5.17; N, 15.99; Found: C, 51.47; H, 5.29; N, 15.76.

Example 86

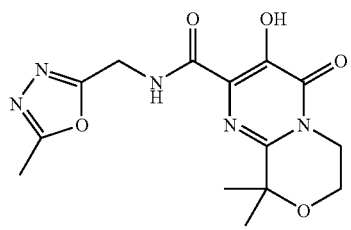

3-Hydroxy-9,9-dimethyl-N-((5-methyl-1,3,4-oxadiazol-2-yl)methyl)-4-oxo-4,6,7,9-tetrahydropyrimido[2,1-c][1,4]oxazine-2-carboxamide. White crystals (87% yield). $^1$HNMR 400 MHz (CDCl$_3$) δ (ppm): 1.63 (6H, s, 2×CH$_3$), 2.58 (3H, s, CH$_3$), 4.05 (4H, s, 2×CH$_2$), 4.84 (2H, d, J=6.1 Hz, NCH$_2$), 8.06 (1H, broad t, NH), 11.59 (1H, s, OH). HRMS (ESI$^+$) calculated for $C_{14}H_{18}N_5O_5$ [M+H$^-$]: 336.1308; found: 336.1294.

Example 87

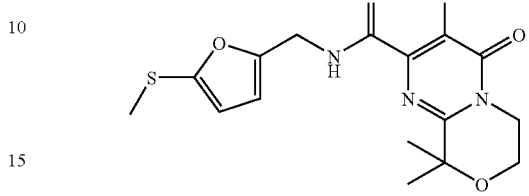

3-Hydroxy-9,9-dimethyl-N-((5-(methylthio)furan-2-yl)methyl)-4-oxo-4,6,7,9-tetrahydropyrimido[2,1-c][1,4]oxazine-2-carboxamide. $^1$H NMR (400 MHz, MeOD): 6.42 (1H, d, J=3.1 Hz), 6.31 (1H, d, J=3.2 Hz), 4.56 (2H, s), 4.03-4.09 (2 H, m), 3.99-3.97 (2H, m), 2.35 (3H, s), 1.61 (6H, s). LCMS ($^+$ESI, M+H$^+$) m/z 366.

Example 88

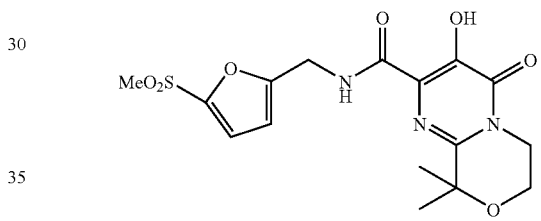

3-Hydroxy-9,9-dimethyl-N-((5-(methylsulfonyl)furan-2-yl)methyl)-4-oxo-4,6,7,9-tetrahydropyrimido[2,1-c][1,4]oxazine-2-carboxamide. $^1$H NMR (400 MHz, MeOD): 7.17 (1H, br s), 6.55 (1H, br s), 4.68 (2H, s), 4.06 (2H, m), 3.98 (2 H, m), 3.20 (3H, s), 1.64 (6H, s). LCMS ($^+$ESI, M+H$^+$) m/z 398.

Example 89

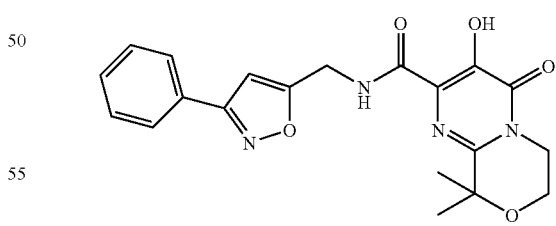

3-Hydroxy-9,9-dimethyl-4-oxo-N-((3-phenyl-5-isoxazolyl)methyl)-4,6,7,9-tetrahydropyrimido[2,1-c][1,4]oxazine-2-carboxamide. $^1$H NMR (500 MHz, DMSO-D$_6$) δ ppm 1.58 (s, 6H), 3.85 (t, J=5.04 Hz, 2H), 3.98 (t, J=5.04 Hz, 2H), 4.69 (d, J=6.10 Hz, 2H), 6.96 (s, 1H), 7.50-7.51 (overlapping m, 3H), 7.84-7.90 (m, 2 H), 9.53 (t, J=6.26 Hz, 1H), 11.97 (s, 1H). $^{13}$C NMR (125 MHz, DMSO-D$_6$) δ 27.52, 34.82, 42.76, 57.36, 75.35, 100.37, 125.22, 126.52, 128.36, 129.00, 130.14, 145.37, 151.74, 156.95, 161.86, 168.58,

Example 90

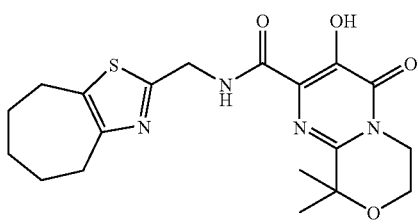

3-Hydroxy-9,9-dimethyl-4-oxo-N-(5,6,7,8-tetrahydro-4H-cyclohepta[d][1,3]thiazol-2-ylmethyl)-4,6,7,9-tetrahydropyrimido[2,1-c][1,4]oxazine-2-carboxamide. $^1$H NMR (500 MHz, DMSO-D$_6$) δ ppm 1.56-1.65 (m, 8H), 1.76-1.82 (m, 2H), 2.72-2.78 (m, 2H), 2.81-2.86 (m, 2H), 3.83 (t, J=5.04 Hz, 2H), 3.98 (t, J=5.04 Hz, 2H), 4.62 (d, J=6.41 Hz, 2H), 9.61 (t, J=6.41 Hz, 1H), 11.98 (s, 1H). $^{13}$C NMR (125 MHz, DMSO-D$_6$) δ 25.45, 26.14, 27.48, 30.84, 31.12, 40.19, 42.75, 57.35, 75.34, 125.14, 132.53, 145.39, 151.77, 154.02, 156.92, 161.03, 168.39. Anal. Calcd. For: C$_{19}$H$_{24}$N$_4$O$_4$S: C, 56.41; H, 5.98; N, 13.85. Found: C, 56.39; H, 5.82; N, 13.61.

Example 91

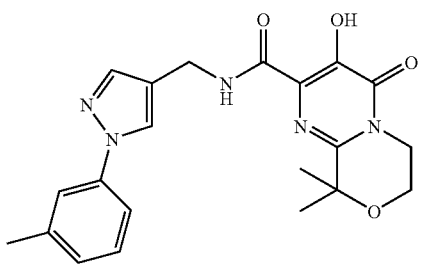

3-Hydroxy-9,9-dimethyl-N-((1-(3-methylphenyl)-1H-pyrazol-4-yl)methyl)-4-oxo-4,6,7,9-tetrahydropyrimido[2,1-c][1,4]oxazine-2-carboxamide. $^1$H NMR (500 MHz, DMSO-D$_6$) δ ppm 1.56 (s, 6H), 2.37 (s, 3H), 3.83 (t, J=5.04 Hz, 2H), 3.97 (t, J=5.04 Hz, 2H), 4.42 (d, J=6.10 Hz, 2H), 7.10 (d, J=7.63 Hz, 1H), 7.35 (t, J=7.93 Hz, 1H), 7.59 (d, J=7.93 Hz, 1H), 7.64 (s, 1H), 7.69 (s, 1H), 8.37 (s, 1 H), 9.31 (s, 1H), 12.34 (s, 1H). $^{13}$C NMR (125 MHz, DMSO-D$_6$) δ 20.95, 27.53, 33.00, 42.71, 57.35, 75.32, 115.25, 118.63, 120.55, 125.46, 126.29, 126.69, 129.23, 139.00, 139.49, 140.41, 145.36, 151.55, 156.97, 168.19. Anal calcd for C$_{21}$H$_{23}$N$_5$O$_4$+0.5H$_2$O: C, 60.27; H, 5.78; N, 16.74. Found: C, 60.13; H, 5.39; N, 16.86.

Example 92

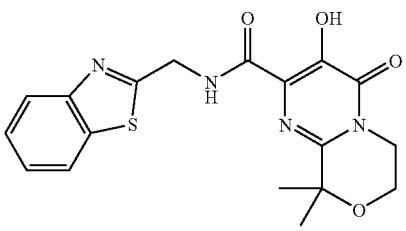

N-(1,3-Benzothiazol-2-ylmethyl)-3-hydroxy-9,9-dimethyl-4-oxo-4,6,7,9-tetrahydropyrimido[2,1-c][1,4]oxazine-2-carboxamide. $^1$H NMR (500 MHz, DMSO-D$_6$) δ ppm 1.59 (s, 6H), 3.85 (t, J=5.04 Hz, 2H), 3.99 (t, J=5.19 Hz, 2H), 4.92 (d, J=6.41 Hz, 2H), 7.43 (t, J=7.48 Hz, 1H), 7.48-7.54 (m, 1H), 7.98 (d, J=7.93 Hz, 1 H), 8.07 (d, J=7.93 Hz, 1H), 9.78 (t, J=6.26 Hz, 1H), 11.88 (s, 1H). $^{13}$C NMR (125 MHz, DMSO-D$_6$) δ 27.51, 41.25, 42.77, 57.37, 75.36, 122.24, 122.37, 125.07, 126.14, 134.52, 145.41, 151.87, 152.44, 156.94, 168.71, 169.48. Anal calcd for C$_{18}$H$_{18}$N$_4$O$_4$S: C, 55.94; H, 4.69; H, 14.49. Found: C, 56.18; H, 4.61; N, 14.48.

Example 93

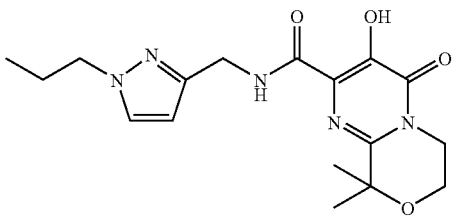

3-Hydroxy-9,9-dimethyl-4-oxo-N-((1-propyl-1H-pyrazol-3-yl)methyl)-4,6,7,9-tetrahydropyrimido[2,1-c][1,4]oxazine-2-carboxamide. $^1$H NMR (500 MHz, DMSO-D$_6$) δ ppm 0.82 (t, J=7.32 Hz, 3H), 1.55 (s, 6H), 1.72-1.80 (m, 2H), 3.83 (t, J=5.04 Hz, 2H), 3.95-4.03 (m, 4H), 4.43 (d, J=6.10 Hz, 2H), 6.13 (d, J=2.14 Hz, 1H), 7.63 (d, J=1.83 Hz, 1H), 9.29 (s, 1H). $^{13}$C NMR (125 MHz, DMSO-D$_6$) δ 10.88, 23.12, 27.46, 36.50, 42.71, 52.60, 57.36, 75.31, 103.47, 125.39, 130.71, 145.36, 148.24, 151.56, 156.98, 168.06. Anal calcd for C$_{17}$H$_{23}$N$_5$O$_4$+0.25 H$_2$O: C, 55.80; H, 6.47; N, 19.14. Found: C, 55.91; H, 6.75; N, 18.76.

We claim:

1. A compound of Formula I

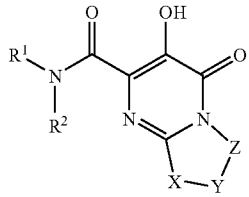

where:
R¹ is (Ar¹)alkyl;
R² is (Ar¹)alkyl, hydrogen, alkyl, hydroxy, or alkoxy;
R³ is hydrogen or alkyl;
R⁴ is alkyl or cycloalkyl;
R⁵ is hydrogen or alkyl;
R⁶ is hydrogen or alkyl;
Ar¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, indazolyl, benzoisoxazolyl, benzoisothiazolyl, benzimidazolyl, benzoxazolyl, benzothiazolyl,

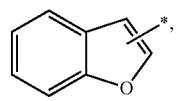 , 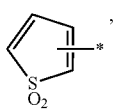 ,

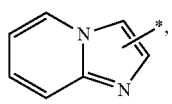 , 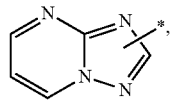 ,

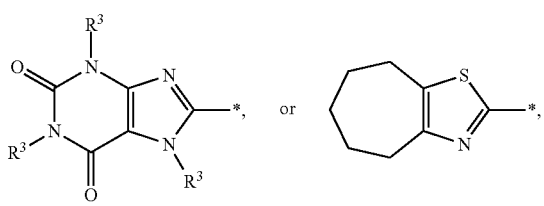

and is substituted with 0-3 substituents selected from the group consisting of oxo, amino, cyano, halo, alkyl, haloalkyl, hydroxy, alkoxy, haloalkoxy, COR³, CO₂R³, CON(R³)(R³), (COR³)alkyl, (CO₂R³)alkyl, (CON(R³)(R³))alkyl, alkylthio, (alkyl)SO, SO₂R⁴, Ar² and (Ar²)alkyl;
  Ar² is phenyl substituted with 0-2 substituents selected from the group consisting of cyano, halo, alkyl, haloalkyl, alkoxy, and haloalkoxy; and
X—Y—Z is C(R⁵)(R⁶)OCH₂CH₂;
or a pharmaceutically acceptable salt thereof.

2. A compound of claim 1 according to the following structures:

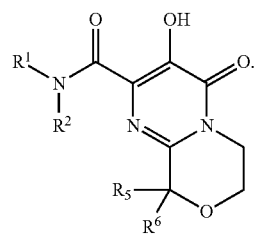

3. A compound of claim 1 where R¹ is (Ar¹)methyl.
4. A compound of claim 1 where R² is hydrogen.
5. A compound of claim 1 selected from the group consisting of
  Pyrimido[2,1-c][1,4]oxazine-2-carboxamide, N-[(1,5-dimethyl-1H-pyrazol-3-yl)methyl]-4,6,7,9-tetrahydro-3-hydroxy-9,9-dimethyl-4-oxo-;
  Pyrimido[2,1-c][1,4]oxazine-2-carboxamide, 4,6,7,9-tetrahydro-3-hydroxy-9,9-dimethyl-4-oxo-N-[(2-phenyl-4-thiazolyl)methyl]-;
  Pyrimido[2,1-c][1,4]oxazine-2-carboxamide, N-[[2-(4-chlorophenyl)-4-thiazolyl]methyl]-4,6,7,9-tetrahydro-3-hydroxy-9,9-dimethyl-4-oxo-;
  Pyrimido[2,1-c][1,4]oxazine-2-carboxamide, 4,6,7,9-tetrahydro-3-hydroxy-9,9-dimethyl-4-oxo-N-(2-thiazolylmethyl)-;
  Pyrimido[2,1-c][1,4]oxazine-2-carboxamide, 4,6,7,9-tetrahydro-3-hydroxy-9,9-dimethyl-4-oxo-N-[(1-phenyl-1H-pyrazol-4-yl)methyl]-;
  Pyrimido[2,1-c][1,4]oxazine-2-carboxamide, 4,6,7,9-tetrahydro-3-hydroxy-9,9-dimethyl-N-[(2-methyl-4-thiazolyl)methyl]-4-oxo-;
  Pyrimido[2,1-c][1,4]oxazine-2-carboxamide, N-[(1,3-dimethyl-1H-pyrazol-5-yl)methyl]-4,6,7,9-tetrahydro-3-hydroxy-9,9-dimethyl-4-oxo-;
  Pyrimido[2,1-c][1,4]oxazine-2-carboxamide, N-[(1,5-dimethyl-1H-pyrazol-2-yl)methyl]-4,6,7,9-tetrahydro-3-hydroxy-9,9-dimethyl-4-oxo-;
  Pyrimido[2,1-c][1,4]oxazine-2-carboxamide, N-[[1-(1,1-dimethylethyl)-5-methyl-1H-pyrazol-3-yl]methyl]-4,6,7,9-tetrahydro-3-hydroxy-9,9-dimethyl-4-oxo-;
  Pyrimido[2,1-c][1,4]oxazine-2-carboxamide, 4,6,7,9-tetrahydro-3-hydroxy-9,9-dimethyl-N-[[3-[(methylamino)carbonyl]-2-furanyl]methyl]-4-oxo-;
  Pyrimido[2,1-c][1,4]oxazine-2-carboxamide, 4,6,7,9-tetrahydro-3-hydroxy-9,9-dimethyl-N-[(1-methyl-1H-indazol-3-yl)methyl]-4-oxo-;
  Pyrimido[2,1-c][1,4]oxazine-2-carboxamide, 4,6,7,9-tetrahydro-3-hydroxy-N-(imidazol[1,2-a]pyridin-2-ylmethyl)-9,9-dimethyl-4-oxo-; 3-Hydroxy-9,9-dimethyl-N-[[(5-(methylcarbamoyl)-2-furyl)methyl)-4-oxo-4,6,7,9-tetrahydropyrimido[2,1-c][1,4]oxazine-2-carboxamide;
  Pyrimido[2,1-c][1,4]oxazine-2-carboxamide, N-[[1-(difluoromethyl)-5-methyl-1H-pyrazol-3-yl]methyl]-4,6,7,9-tetrahydro-3-hydroxy-9,9-dimethyl-4-oxo-;
  Pyrimido[2,1-e][1,4]oxazine-2-carboxamide, 4,6,7,9-tetrahydro-3-hydroxy-9,9-dimethyl-N-[[5-methyl-1-(1-methylethyl)-1H-pyrazol-3-yl]methyl]-4-oxo-;
  Pyrimido[2,1-c][1,4]oxazine-2-carboxamide, N-[[1-(2-fluoroethyl)-5-methyl-1H-pyrazol-3-yl]methyl]-4,6,7,9-tetrahydro-3-hydroxy-9,9-dimethyl-4-oxo-;

Pyrimido[2,1-e][1,4]oxazine-2-carboxamide, N-[(5,7-dimethyl[1,2,4]triazolo[1,5-a]pyrimidin-2-yl)methyl]-4,6,7,9-tetrahydro-3-hydroxy-9,9-dimethyl-4-oxo-;

Pyrimido[2,1-c][1,4]oxazine-2-carboxamide, N-(1H-benzimidazol-2-ylmethyl)-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-N-[(4-methyl-5-thiazolyl)methyl]-4-oxo-;

Pyrimido[2,1-c][1,4]oxazine-2-carboxamide, N-[(2,4-dimethyl-5-thiazolyl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-N-[(1 methyl-1H-1,2,3-triazol-4-yl)methyl]-4-oxo-;

Pyrimido[2,1-c][1,4]oxazine-2-carboxamide, 4,6,7,9-tetrahydro-3-hydroxy-9,9-dimethyl-N,N-bis[(1-methyl-1H-1,2,3-triazol-4-yl)methyl]-4-oxo-;

Pyrimido[2,1-c][,4]oxazine-2-carboxamide, 4,6,7,9-tetrahydro-3-hydroxy-9,9-dimethyl-4-oxo-N-[[5-(phenylmethyl)-2-furanyl]methyl];

Pyrimido[2,1-c][1,4]oxazine-2-carboxamide, 4,6,7,9-tetrahydro-3-hydroxy-9,9-dimethyl-4-oxo-N-(2-thienylmethyl)-;

Pyrimido[2,1-c][1,4]oxazine-2-carboxamide, 4,6,7,9-tetrahydro-3-hydroxy-9,9-dimethyl-N-[(5-methyl-2-thienyl)methyl]-4-oxo-;

Pyrimido[2,1-c][1,4]oxazine-2-carboxamide, 4,6,7,9-tetrahydro-3-hydroxy-9,9-dimethyl-N-[(4-methyl-2-thienyl)methyl]-4-oxo-;

N-((4,5-dimethyl-2-thienyl)methyl)-3-hydroxy-9,9-dimethyl-4-oxo-4,6,7,9-tetrahydropyrimido[2,1-c][1,4]oxazine-2-carboxamide;

Pyrimido[2,1-c][1,4]oxazine-2-carboxamide, 4,6,7,9-tetrahydro-3-hydroxy-9,9-dimethyl-N-[(5-methyl-3-thienyl)methyl]-4-oxo-;

Pyrimido[2,1-c][1,4]oxazine-2-carboxamide, N-[(3-bromo-5-methyl-2-thienyl)methyl]-4,6,7,9-tetrahydro-3-hydroxy-9,9-dimethyl-4-oxo-;

Pyrimido[2,1-c][1,4]oxazine-2-carboxamide, N-[(3-cyano-5-methyl-2-thienyl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-N-[(5-methyl-1,1-dioxido-2-thienyl)methyl]-4-oxo-;

Pyrimido[2,1-c][1,4]oxazine-2-carboxamide, 4,6,7,9-tetrahydro-3-hydroxy-9,9-dimethyl-4-oxo-N-(3-thienylmethyl)-;

Pyrimido[2,1-c][1,4]oxazine-2-carboxamide, 4,6,7,9-tetrahydro-3-hydroxy-9,9-dimethyl-N-[(5-methyl-2-furanyl)methyl]-4-oxo-;

Pyrimido[2,1-c][1,4]oxazine-2-carboxamide, N-(2-furanylmethyl)-4,6,7,9-tetrahydro-3-hydroxy-9,9-dimethyl-4-oxo-, Pyrimido[2,1-c][1,4]oxazine-2-carboxamide, 4,6,7,9-tetrahydro-3-hydroxy-9,9-dimethyl-4-oxo-N-[(1,3,5-trimethyl-1H-pyrazol-4-yl)methyl]-;

Pyrimido[2,1-c][1,4]oxazine-2-carboxamide, N-[(2-bromo-3-thienyl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-N-[[5-methyl-2-(trifluoromethyl)-3-furanyl]methyl]-4-oxo-;

Pyrimido[2,1-c][1,4]oxazine-2-carboxamide, 4,6,7,9-tetrahydro-3-hydroxy-9,9-dimethyl-N-[(5-methyl-3-phenyl-4-isoxazolyl)methyl]-4-oxo-;

Pyrimido[2,1-c][1,4]oxazine-2-carboxamide, N-[(2,5-dimethyl-3-furanyl)methyl]-4,6,7,9-tetrahydro-3-hydroxy-9,9-dimethyl-4-oxo-;

Pyrimido[2,1-c][1,4]oxazine-2-carboxamide, N-[[3-(4-chlorophenyl)-5-isoxazolyl]methyl]-4,6,7,9-tetrahydro-3-hydroxy-9,9-dimethyl-4-oxo-;

Pyrimido[2,1-c][1,4]oxazine-2-carboxamide, N-[(1-ethyl-3-methyl-1H-pyrazol-5-yl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-N-[(1-methyl-1H-pyrazol-2-yl)methyl]-4-oxo-;

Pyrimido[2,1-c][1,4]oxazine-2-carboxamide, 4,6,7,9-tetrahydro-3-hydroxy-N-[[3-(4-methoxyphenyl)-5-isoxazolyl]methyl]-9,9-dimethyl-4-oxo-;

Pyrimido[2,1-c][1,4]oxazine-2-carboxamide, 4,6,7,9-tetrahydro-3-hydroxy-9,9-dimethyl-N-[(5-methyl-2-phenyl-2H-1,2,3-triazol-4-yl)methyl]-4-oxo-;

Pyrimido[2,1-c][1,4]oxazine-2-carboxamide, N-[(5,6-dichloro-1H-benzimidazol-2-yl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-4-oxo-N-[2-(2-thienyl)ethyl]-;

Pyrimido[2,1-c][1,4]oxazine-2-carboxamide, N-[(4-chloro-3-methyl-5-isoxazolyl)methyl]-4,6,7,9-tetrahydro-3-hydroxy-9,9-dimethyl-4-oxo-;

2-Thiopheneacetic acid, 5-[[[(4,6,7,9-tetrahydro-3-hydroxy-9,9-dimethyl-4-oxopyrimido[2,1-c][1,4]oxazin-2-yl)carbonyl]amino]methyl]-;

Pyrimido[2,1-c][1,4]oxazine-2-carboxamide, N-(1,2-benzisoxazol-3-ylmethyl)-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-4-oxo-N-[(2,3,6,7-tetrahydro-1,3,7-trimethyl-2,6-dioxo-1H-purin-8-yl)methyl]-;

Pyrimido[2,1-c][1,4]oxazine-2-carboxamide, N-[(1,3-dimethyl-1H-pyrazol-4-yl)methyl]-4,6,7,9-tetrahydro-3-hydroxy-9,9-dimethyl-4-oxo-;

Pyrimido[2,1-c][1,4]oxazine-2-carboxamide, N-[(1-ethyl-3-methyl-H-pyrazol-4-yl)methyl]-4,6,7,9-tetrahydro-3-hydroxy-9,9-dimethyl-4-oxo-;

Pyrimido[2,1-c][1,4]oxazine-2-carboxamide, N-[(1-ethyl-5-methyl-1H-pyrazol-4-yl)methyl]-4,6,7,9-tetrahydro-3-hydroxy-9,9-dimethyl-4-oxo-;

Pyrimido[2,1-c][1,4]oxazine-2-carboxamide, N-[(1-ethyl-1H-pyrazol-4-yl)methyl]-4,6,7,9-tetrahydro-3-hydroxy-9,9-dimethyl-4-oxo-;

Pyrimido[2,1-c][1,4]oxazine-2-carboxamide, N-[(1,3-diphenyl-1H-pyrazol-4-yl)methyl]-4,6,7,9-tetrahydro-3-hydroxy-9,9-dimethyl-4-oxo-;

Pyrimido[2,1-c][1,4]oxazine-2-carboxamide, N-[(1-ethyl-1H-pyrazol-3-yl)methyl]-4,6,7,9-tetrahydro-3-hydroxy-9,9-dimethyl-4-oxo-;

Pyrimido[2,1-c][1,4]oxazine-2-carboxamide, N-[(1-ethyl-1H-pyrazol-5-yl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-4-oxo-N-(1H-pyrazol-3-ylmethyl)-;

Pyrimido[2,1-c][1,4]oxazine-2-carboxamide, N-[(4-chloro-1-ethyl-1H-pyrazol-3-yl)methyl]-4,6,7,9-tetrahydro-3-hydroxy-9,9-dimethyl-4-oxo-;

Pyrimido[2,1-c][1,4]oxazine-2-carboxamide, N-[(4-chloro-1-ethyl-1H-pyrazol-5-yl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-N-[(1-methyl-1H-pyrazol-3-yl)methyl]-4-oxo-;

Pyrimido[2,1-c][1,4]oxazine-2-carboxamide, N-[(4-bromo-1-ethyl-1H-pyrazol-5-yl)methyl]-4,6,7,9-tetrahydro-3-hydroxy-9,9-dimethyl-4-oxo-;

Pyrimido[2,1-c][1,4]oxazine-2-carboxamide, 4,6,7,9-tetrahydro-3-hydroxy-9,9-dimethyl-N-[(4-methyl-2-phenyl-5-thiazolyl)methyl]-4-oxo-;

3-Furancarboxylic acid, 5-[[[(4,6,7,9-tetrahydro-3-hydroxy-9,9-dimethyl-4-oxopyrimido[2,1c][1,4]oxazin-2-yl)carbonyl]amino]methyl]-;

3-Hydroxy-9,9-dimethyl-N-((1-(methylsulfonyl)-1H-indazol-3-yl)methyl)-4-oxo-4,6,7,9-tetrahydropyrimido[2,1-c][1,4]oxazine-2-carboxamide;

Methyl 3-((((3-hydroxy-9,9-dimethyl-4-oxo-4,6,7,9-tetrahydroprimido[2,1-c][1,4]oxazin-2-yl)carbonyl)amino)methyl)-1H-indazole-1-carboxylate;

3-Hydroxy-9,9-dimethyl-N-((1-(methylcarbamoyl)-1H-indazol-3-yl)methyl)-4-oxo-4,6,7,9-tetrahydropyrimido[2,1-c][1,4]oxazine-2-carboxamide;

N-((1-Acetyl-1H-indazol-3-yl)methyl)-3-hydroxy-9,9-dimethyl-4-oxo-4,6,7,9-tetrahydropyrimido[2,1-c][1,4]oxazine-2-carboxamide;

3-Hydroxy-9,9-dimethyl-N-((2-methylthiazol-5-yl)methyl)-4-oxo-4,6,7,9-tetrahydropyrimido[2,1-c][1,4]oxazine-2-carboxamide;

3-Hydroxy-9,9-dimethyl-N-((5-methyl-1,3,4-oxadiazol-2-yl)methyl)-4-oxo-4,6,7,9-tetrahydropyrimido[2,1-c][1,4]oxazine-2-carboxamide;

3-Hydroxy-9,9-dimethyl-N-((5-(methylthio)furan-2-yl)methyl)-4-oxo-4,6,7,9-tetrahydropyrimido[2,1-c][1,4]oxazine-2-carboxamide;

3-Hydroxy-9,9-dimethyl-N-((5-(methylsulfonyl)furan-2-yl)methyl)-4-oxo-4,6,7,9-tetrahydropyrimido[2,1-c][1,4]oxazine-2-carboxamide;

3-Hydroxy-9,9-dimethyl-4-oxo-N-((3-phenyl-5-isoxazolyl)methyl)-4,6,7,9-tetrahydropyrimido[2,1-c][1,4]oxazine-2-carboxamide;

3-Hydroxy-9,9-dimethyl-4-oxo-N-(5,6,7,8-tetrahydro-4H-cyclohepta[d][1,3]thiazol-2-ylmethyl)-4,6,7,9-tetrahydropyrimido[2,1-c][1,4]oxazine-2-carboxamide;

3-Hydroxy-9,9-dimethyl-N-((1-(3-methylphenyl)-1H-pyrazol-4-yl)methyl)-4-oxo-4,6,7,9-tetrahydropyrimido[2,1-c][1,4]oxazine-2-carboxamide;

N-(1,3-Benzothiazol-2-ylmethyl)-3-hydroxy-9,9-dimethyl-4-oxo-4,6,7,9-tetrahydropyrimido[2,1-c][1,4]oxazine-2-carboxamide; and 3-Hydroxy-9,9-dimethyl-4-oxo-N-((1-propyl-1H-pyrazol-3-yl)methyl)-4,6,7,9-tetrahydropyrimido[2,1-c][1,4]oxazine-2-carboxamide;

or a pharmaceutically acceptable salt thereof.

6. A composition comprising a therapeutic amount of a compound of claim 1 and a pharmaceutically acceptable carrier.

7. A method for treating HIV infection comprising administering a therapeutically effective amount of a compound of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO.       : 7,893,055 B2
APPLICATION NO.  : 11/768458
DATED            : February 22, 2011
INVENTOR(S)      : Michael A. Walker et al.

It is certified that error appears in the above-identified patent and that said Letters Patent is hereby corrected as shown below:

Claim 5:

Column 114, lines 54 and 55, change "ylmethyl)" to -- yl-methyl) --.

Column 114, lines 55 to 58, after "-4-oxo;" move "3-Hydroxy-9,9-dimethyl-N-[[(5-(methylcarbamoyl)-2-furyl)methyl)-4-oxo-4,6,7,9-tetrahydropyrimido[2,1-c][1,4]oxazine-2-carboxamide;" to next line as a separate paragraph.

Column 115, line 1, change "[2,1-e]" to -- [2,1-c] --.

Column 115, line 5, change "-2-ylmethyl)" to -- -2-yl-methyl) --.

Column 115, line 14, change "(1 methyl" to -- (1-methyl --.

Column 115, line 19, change "[,4]" to -- [1,4] --.

Column 116, line 32, change "-3-ylmethyl)" to -- -3-yl-methyl) --.

Column 116, line 61, change "-3-ylmethyl)" to -- -3-yl-methyl) --.

Column 117, line 11, change "[2,1c]" to -- [2,1-c] --.

Column 118, line 11, change "-2-ylmethyl)" to -- -2-yl-methyl) --.

Column 118, line 16, change "-2-ylmethyl)" to -- -2-yl-methyl) --.

Signed and Sealed this
Sixth Day of December, 2011

David J. Kappos
*Director of the United States Patent and Trademark Office*